US011661602B2

(12) United States Patent
Van Der Veer et al.

(10) Patent No.: US 11,661,602 B2
(45) Date of Patent: May 30, 2023

(54) INHIBITION OF POLYOMAVIRUS REPLICATION

(71) Applicant: ACADEMISCH ZIEKENHUIS LEIDEN H.O.D.N. LUMC, Leiden (NL)

(72) Inventors: Eric Peter Van Der Veer, The Hague (NL); Anton Jan Van Zonneveld, Soest (NL); Jurriën Prins, The Hague (NL)

(73) Assignee: ACADEMISCH ZIEKENHUIS LEIDEN H.O.D.N. LUMC, Leiden (NL)

( * ) Notice: Subject to any disclaimer, the term of this patent is extended or adjusted under 35 U.S.C. 154(b) by 0 days.

(21) Appl. No.: 16/977,779

(22) PCT Filed: Mar. 1, 2019

(86) PCT No.: PCT/NL2019/050131
§ 371 (c)(1),
(2) Date: Sep. 2, 2020

(87) PCT Pub. No.: WO2019/168402
PCT Pub. Date: Sep. 6, 2019

(65) Prior Publication Data
US 2021/0010004 A1    Jan. 14, 2021

(30) Foreign Application Priority Data

Mar. 2, 2018  (EP) ..................................... 18159797

(51) Int. Cl.
*C12N 15/11*      (2006.01)
*C12N 15/113*     (2010.01)
*A61K 31/7125*    (2006.01)

(52) U.S. Cl.
CPC ...... *C12N 15/1131* (2013.01); *A61K 31/7125* (2013.01); *C12N 2310/11* (2013.01); *C12N 2310/315* (2013.01); *C12N 2310/321* (2013.01); *C12N 2310/346* (2013.01); *C12N 2320/33* (2013.01)

(58) Field of Classification Search
CPC ............ C12N 15/1131; C12N 2310/11; C12N 2310/315; C12N 2310/321; C12N 2310/346; C12N 2320/33; A61K 31/7125
See application file for complete search history.

(56) References Cited

U.S. PATENT DOCUMENTS

2005/0100885 A1 * 5/2005 Crooke .............. C12N 15/1137
                                                    435/5
2009/0062225 A1 * 3/2009 Tan ........................ A61P 31/12
                                                    514/44 R

FOREIGN PATENT DOCUMENTS

| WO | WO-2005112636 A2 * | 12/2005 | ......... C12N 15/1131 |
| WO | 2009100351 A2 | 8/2009 | |
| WO | 2012143427 A1 | 10/2012 | |
| WO | 2013119979 A1 | 8/2013 | |
| WO | 2015042466 A2 | 3/2015 | |
| WO | WO-2017100431 A2 * | 6/2017 | ........... A61K 38/465 |

OTHER PUBLICATIONS

Vickers et al, Efficient reduction of target RNAs by small interfering RNA and RNase H-dependent antisense agents, JBC, 2003, 278, 9: 7108-7118 (Year: 2003).*
Altschul et al., Basic Local Alignment Search Tool, Journal of Molecular Biology, 1990, pp. 403-410, vol. 215, Academic Press Limited.
Database Geneseq [Online], BK virus DNA amplifying PCR primer, Seq ID No. 270., Nov. 26, 2009, 1 page. Retrieved from EBI accession No. GSN:AXR30570.
Database Geneseq [Online], BK virus DNA amplifying PCR primer, Seq ID No. 271., Nov. 26, 2009, 1 page. Retrieved from EBI accession No. GSN:AXR30571.
Database Geneseq [Online], BK virus DNA amplifying PCR primer, Seq ID No. 329., Nov. 26, 2009, 1 page. Retrieved from EBI accession No. GSN:AXR30629.
Database Geneseq [Online], JC polyomavirus targeted siRNA sequence, Seq ID 452., Sep. 30, 2010, 2 pages. Retrieved from EBI accession No. GSN:AXS48128.
Database Geneseq [Online], JC polyomavirus targeted siRNA sequence, Seq ID 460., Sep. 30, 2010, 2 pages. Retrieved from EBI accession No. GSN:AXS48136.
Prakash, Thazha P., An Overview of Sugar-Modified Oligonucleotides for Antisense Therapeutics, Chemistry & Biodiversity, 2011, pp. 1616-1641, vol. 8.
Database Geneseq [Online], WU Polyomavirus dna sequencing primer (AG0035), Seq ID 62., Sep. 15, 2011, 1 page. Retrieved from EBI accession No. GSN:AZL48098.
Database Geneseq [Online], BK polyomavirus target gene-specific antisense oligomer, Seq: 74, Dec. 20, 2012, 1 page. Retrieved from EBI accession No. GSN:BAE63451.
Hug et al., Survey and Summary Mechanism and regulation of the nonsense-mediated decay pathway, Nucleic Acids Research, 2016, pp. 1483-1495. vol. 44, Issue 4, Oxford University Press.
Gard et al., A delicate balance between rejection and BK polyomavirus associated nephropathy; A retrospective cohort study in renal transplant recipients, PLOS ONE, Jun. 13, 2017, 17 pages.
Wunderink et. al., Pretransplantation Donor-Recipient Pair Seroreactivity Against BK Polyomavirus Predicts Viremia and Nephropathy After Kidney Transplantation, American Journal of Transplantation, 2017, pp. 161-172, vol. 17, Wiley Periodicals Inc.

(Continued)

*Primary Examiner* — Ekaterina Poliakova-Georgantas
(74) *Attorney, Agent, or Firm* — Lathrop GPM LLP; James H. Velema, Esq.; Michael Spellberg

(57) ABSTRACT

The invention relates to antisense molecules and methods for modulating splicing of polyomavirus T antigen premRNA. In one aspect the invention relates to an antisense oligonucleotide 12 to 30, preferably 17, 18, 19 or 20 to 30 nucleobases in length which comprises a sequence that is the reverse complement of a contiguous stretch of at least 12 nucleobases of a polyomavirus T-antigen pre-mRNA and which antisense oligonucleotide can modulate splicing of said T-antigen pre-mRNA in a cell.

10 Claims, 57 Drawing Sheets
Specification includes a Sequence Listing.

(56) References Cited

OTHER PUBLICATIONS

Database Geneseq [Online], Cpf1/gRNA targeting JCV large T antigen target DNA cm181, Seq ID: 194, Aug. 10, 2017, 2 pages. Retrieved from EBI accession No. GSN:BDZ64476.

Database Geneseq [Online], Cpf1/gRNA targeting JCV large T antigen target DNA cm182, Seq ID:195., Aug. 10, 2017, 2 pages. Retrieved from EBI accession No. GSN:BDZ64477.

Database Geneseq [Online], BK virus genomic DNA specific forward real-time PCR primer Seq; 6, Jun. 14, 2018, 1 page. Retrieved from EBI accession No. GSN:BFF97332.

De Vlaminck et al., Temporal Response of the Human Virome to Immunosuppression and Antiviral Therapy, Cell, Nov. 21, 2013, pp. 1178-1187, vol. 155, Elsevier Inc.

Hasegawa et al., Association of DNA Amplification With Progress of BK Polymavirus Infection and Nephropathy in Renal Transplant Recipients, Transplantation Proceedings, 2014, pp. 556-559, vol. 46, Elsevier Inc., New York, NY.

Helle et al., Biology of the BKPyV: An Update, Viruses, 2017, pp. 1-18, vol. 9, Issue 327.

Nickeleit et al., The Banff Working Group Classification of Definitive Polyomavirus Nephropathy: Morphologic Definitions and Clinical Correlations, Journal of American Society of Nephrology, 2018, pp. 680-693, vol. 29.

Parajuli et al., Which is more nephrotoxic for kidney transplants: BK nephropathy or rejection?, Clinical Transplantation, 2018, pp. 1-7, vol. 32, Issue e13216, John Wiley & Sons Ltd.

Reploeg et al., BK Virus: A Clinical Review, Clinical Infectious Diseases, Jul. 15, 2001, pp. 191-202, vol. 33.

Sanzani et al., Therapeutic potential of antisense oligonucleotides as modulators of alternative splicing, The Journal of Clinical Investigation, Aug. 2003, pp. 481-486, vol. 112, Issue 4.

Westermann et al., Inhibition of expression of SV40 virus large T-antigen by antisense oligodeoxyribonucleotides, Biomedica Biochimica Acta, 1989, pp. 85-93, vol. 38, No. 1, Akademie Verlag, Berlin, Germany.

Wunderink et al., Stability of BK polymavirus IgG seroreactivity and its correlation with preceding viremia, Journal of Clinical Virology, 2017, pp. 46-51, vol. 90, Elsevier B.V.

Zhang et al., PowerBLAST: A New Network BLAST Application for Interactive or Automated Sequence Analysis and Annotation, Genome Research, 1997, pp. 649-656, Cold Spring Harbor Laboratory Press.

Zheng, Zhi-Ming, Viral Oncogenes, Noncoding RNAs, and RNA Splicing in Human Tumor Viruses, International Journal of Biological Sciences, 2010, pp. 730-755, vol. 6, Issue 7, Ivy Spring International Publisher.

Zhong et al., Distribution patterns of BK polyomavirus (BKV) subtypes and subgroups in American, European and Asian populations suggest co-migration of BKV and the human race, Journal of General Virology, 2009, pp. 144-152, vol. 90, SGM, Great Britain.

PCT International Preliminary Report on Patentability, International Application No. PCT/NL2019/050131, dated Sep. 8, 2020, 10 pages, The International Bureau of WIPO.

PCT International Search Report and Written Opinion, International Application No. PCT/NL2019/050131, dated Jul. 19, 2019, 20 pages, European Patent Office.

Extended European Search Report, Application No. 18159797.2, dated Aug. 6, 2018, 14 pages, European Patent Office.

* cited by examiner

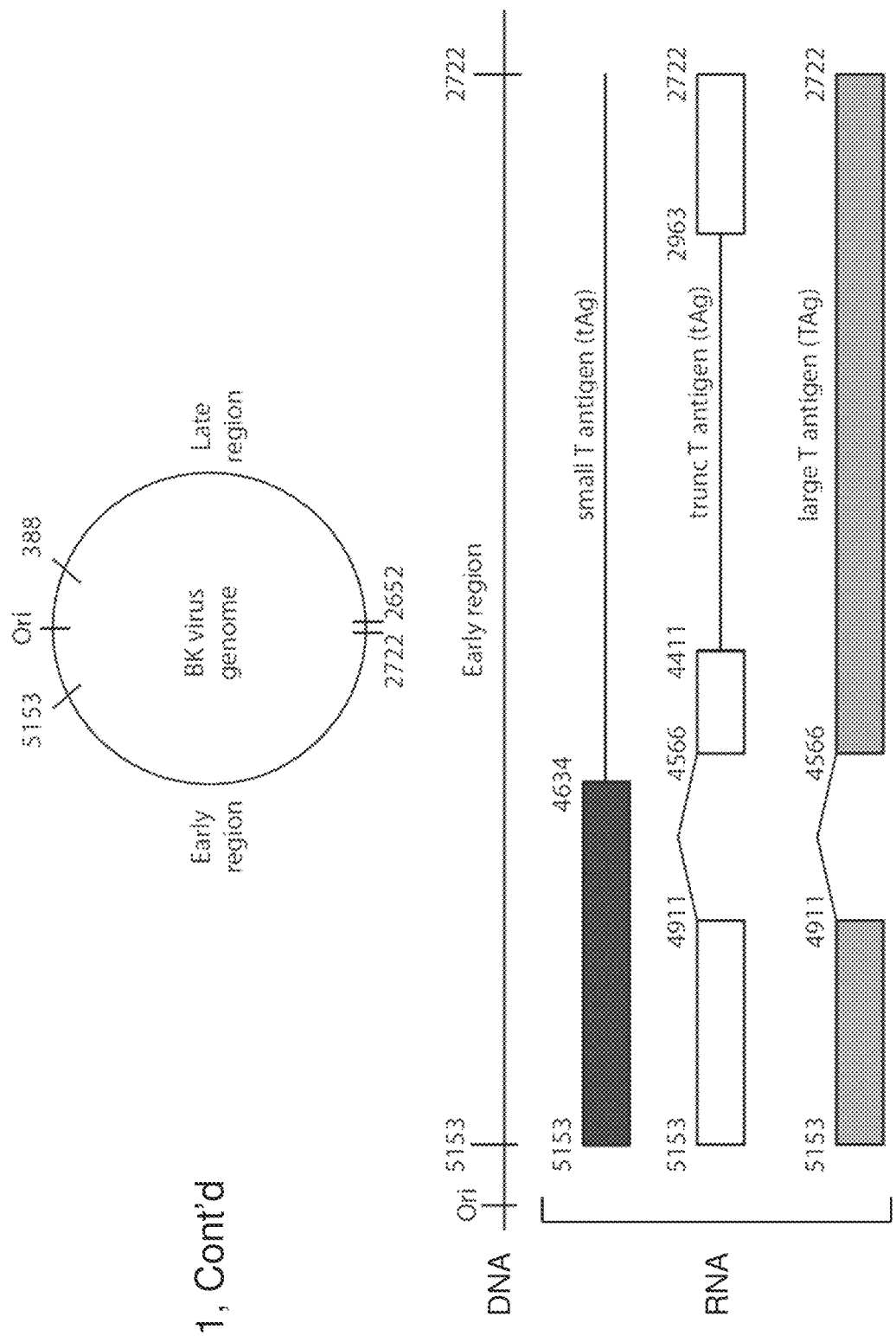
Fig. 1, Cont'd

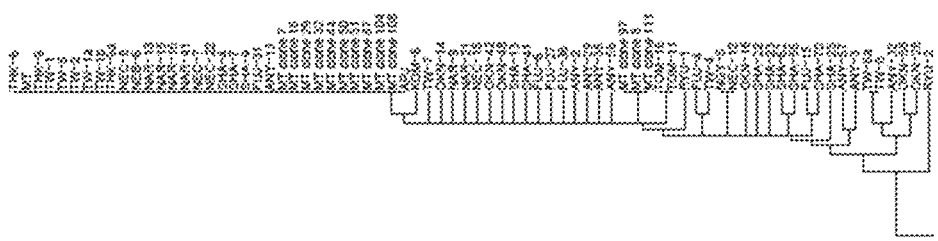
Fig. 2 (1)

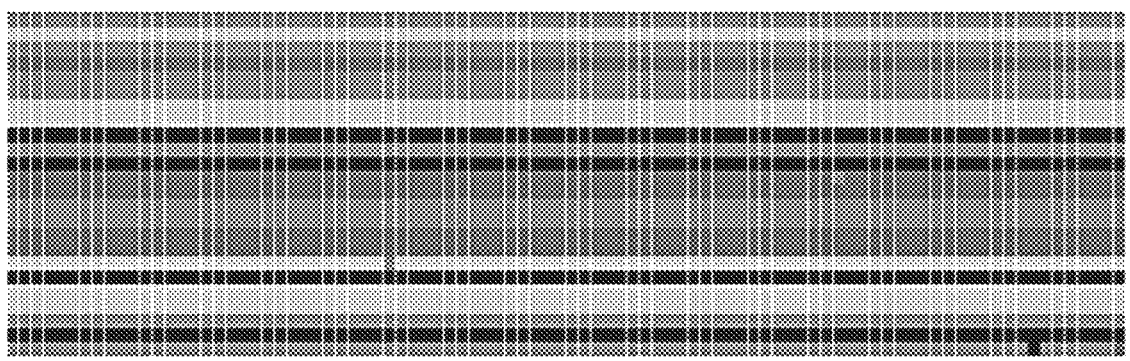
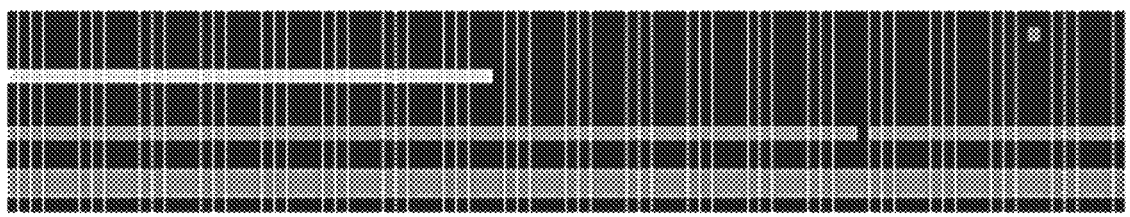
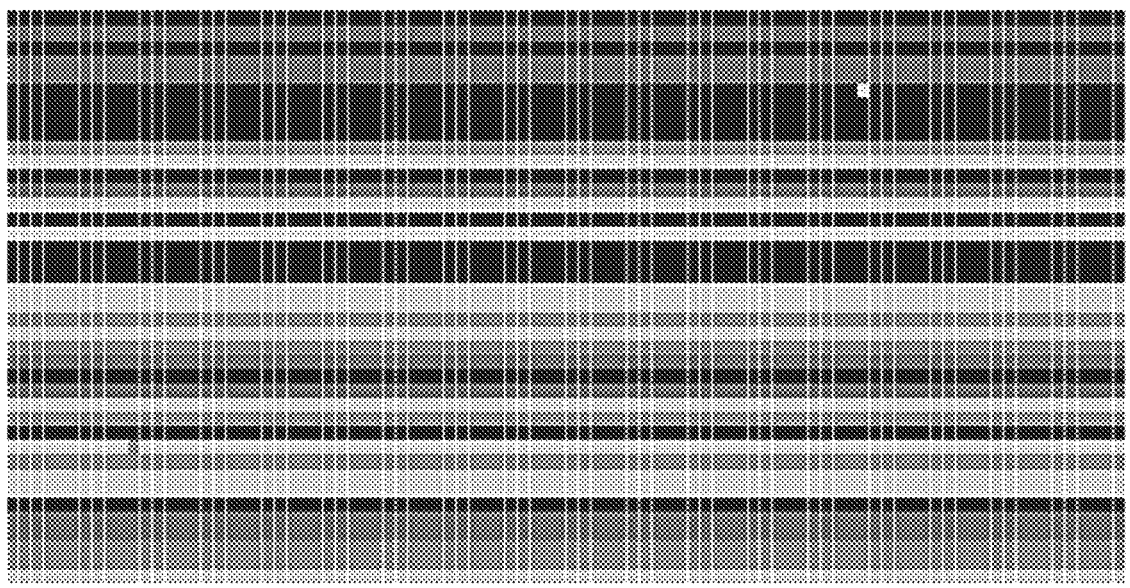
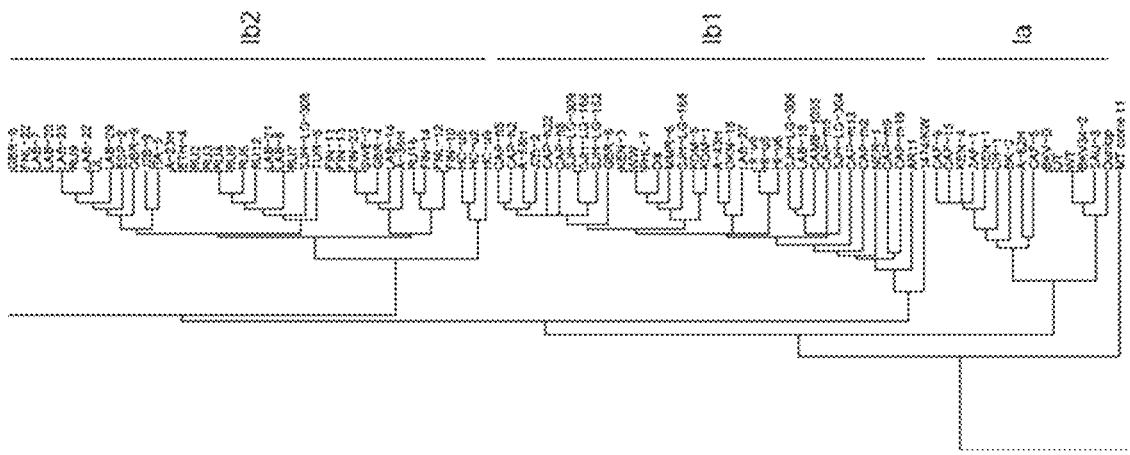
Fig. 2 (2)

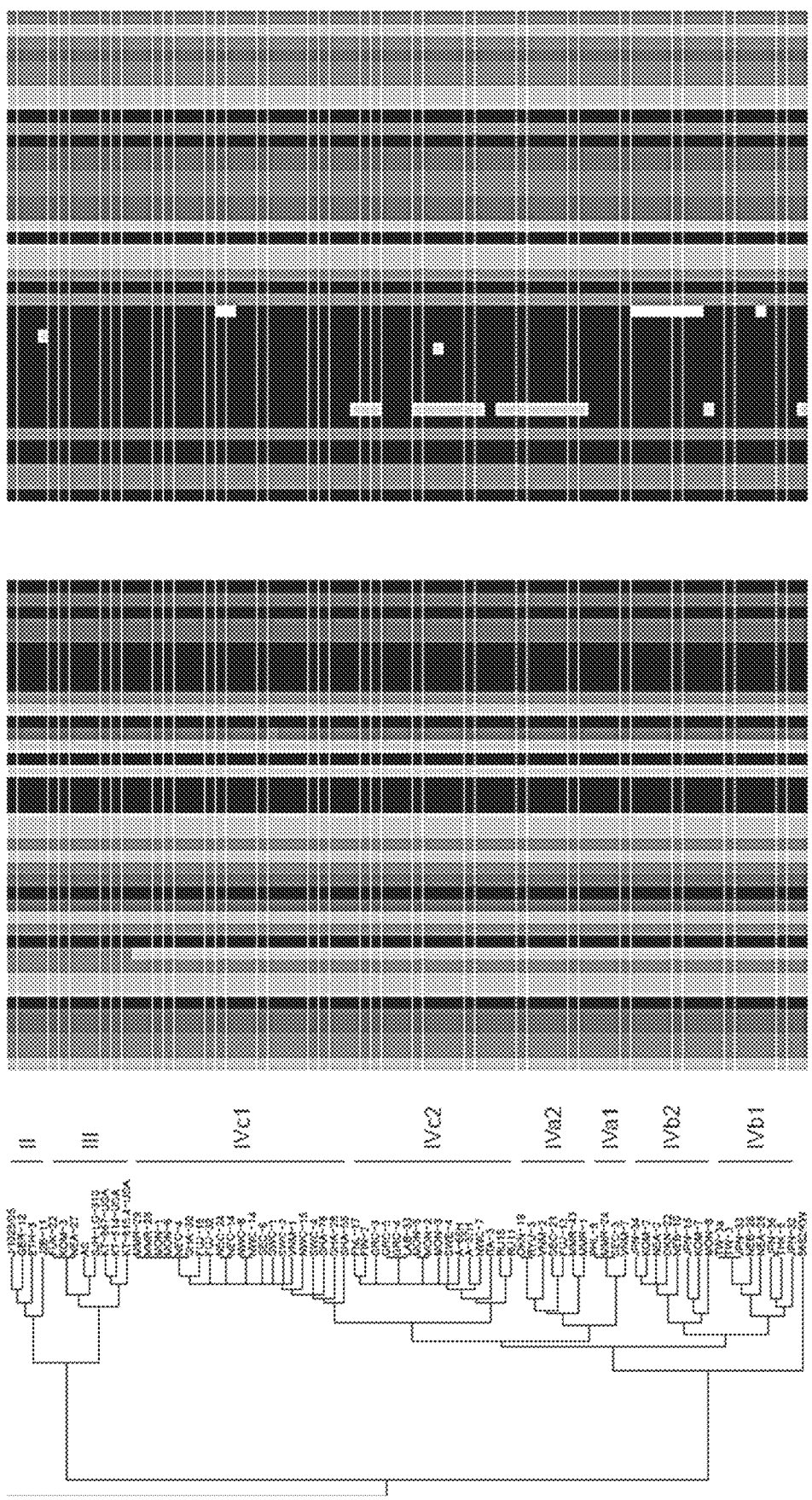
Fig. 2 (3)

| Name | Sequence | Target splice site in TAg | SEQ ID NO |
|---|---|---|---|
| Scrambled | G*C*A*C*C*U*C*G*U*C*G*U*C*C*U*A*G*A*A*U | Non-targeting | 36 |
| AON #1 | A*C*C*U*C*U*G*A*G*C*U*A*C*U*C*C*A*G*G*U | Donor (exon 1) | 1 |
| AON #2 | A*C*A*A*C*C*U*G*A*G*C*U*A*C*U*C*C | Donor (exon 1) | 2 |
| AON #3 | C*A*G*C*A*C*A*A*A*C*C*U*G*A*G*C*U*A | Donor (exon 1) | 3 |
| AON #4 | U*C*A*U*G*U*U*G*G*C*A*C*C*U*A*G*A | Acceptor (exon 2) | 4 |
| AON #5 | U*G*U*U*C*C*A*U*A*G*G*U*U*G*G*C*A*C*C*U | Acceptor (exon 2) | 5 |

SEQ ID NO: 54  GAACCTGGAGTAGCTCAGAGGTTTGTGCTGATTTCCTCT  TAATTATTTTTTT  GTAGGTCCAACCTATGGAACAGA  SEQ ID NO: 53

Exon 1 — Intron — Exon 2

Fig. 3

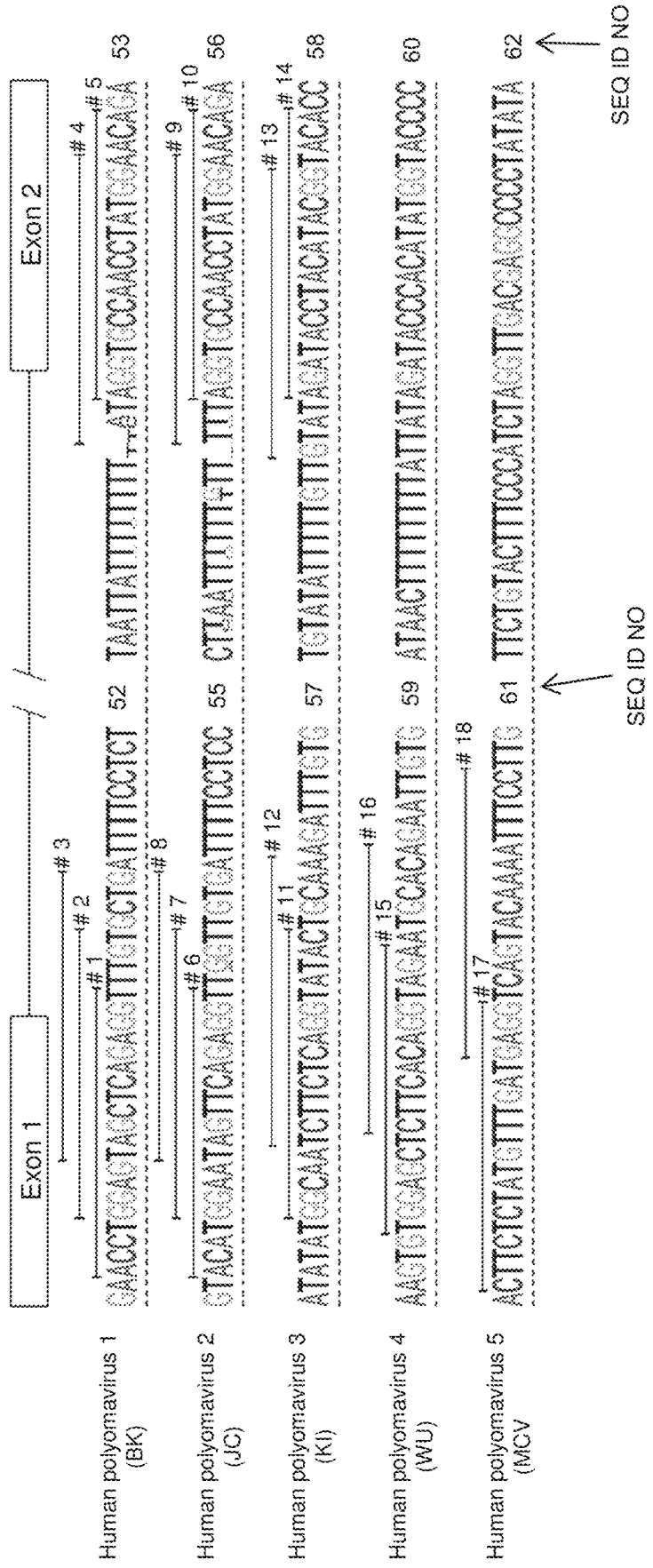
Fig. 9 (1)

| Name | Sequence | SEQ ID NO |
|---|---|---|
| AON #1 | ACCUCUGAGCUACUCCAGGU | 1 |
| AON #2 | ACAAACCUCUGAGCUACUCC | 2 |
| AON #3 | CAGCACAAACCUCUGAGCUA | 3 |
| AON #4 | UCCAUAGGUUGGCACCUAGA | 4 |
| AON #5 | UGUUCCAUAGGUUGGCACCU | 5 |
| AON #6 | ACCUCUGAACUAUUCCAUGU | 6 |
| AON #7 | ACCAACCUCUGAACUAUUCC | 7 |
| AON #8 | CACAACCAACCUCUGAACUA | 8 |
| AON #9 | UCCAUAGGUUGGCACCUAAA | 9 |
| AON #10 | UGUUCCAUAGGUUGGCACCU | 10 |
| AON #11 | GUAUACCUGAGAAGAUUGCC | 11 |
| AON #12 | UCUUUGCAGUAUACCUGAGA | 12 |
| AON #13 | UGUACCGUAUGUAGGUAUCU | 13 |
| AON #14 | CCGUAUGUAGGUAUCUAUAC | 14 |
| AON #15 | UCUACCUGUGAAGAGCUCCA | 15 |
| AON #16 | UGUGCAUUCUACCUGUGAAG | 16 |
| AON #17 | CCUCAUCAAACAUAGAGAAG | 17 |
| AON #18 | GGAAAUUUUGUACUGACCUC | 18 |

Fig. 9 (2)

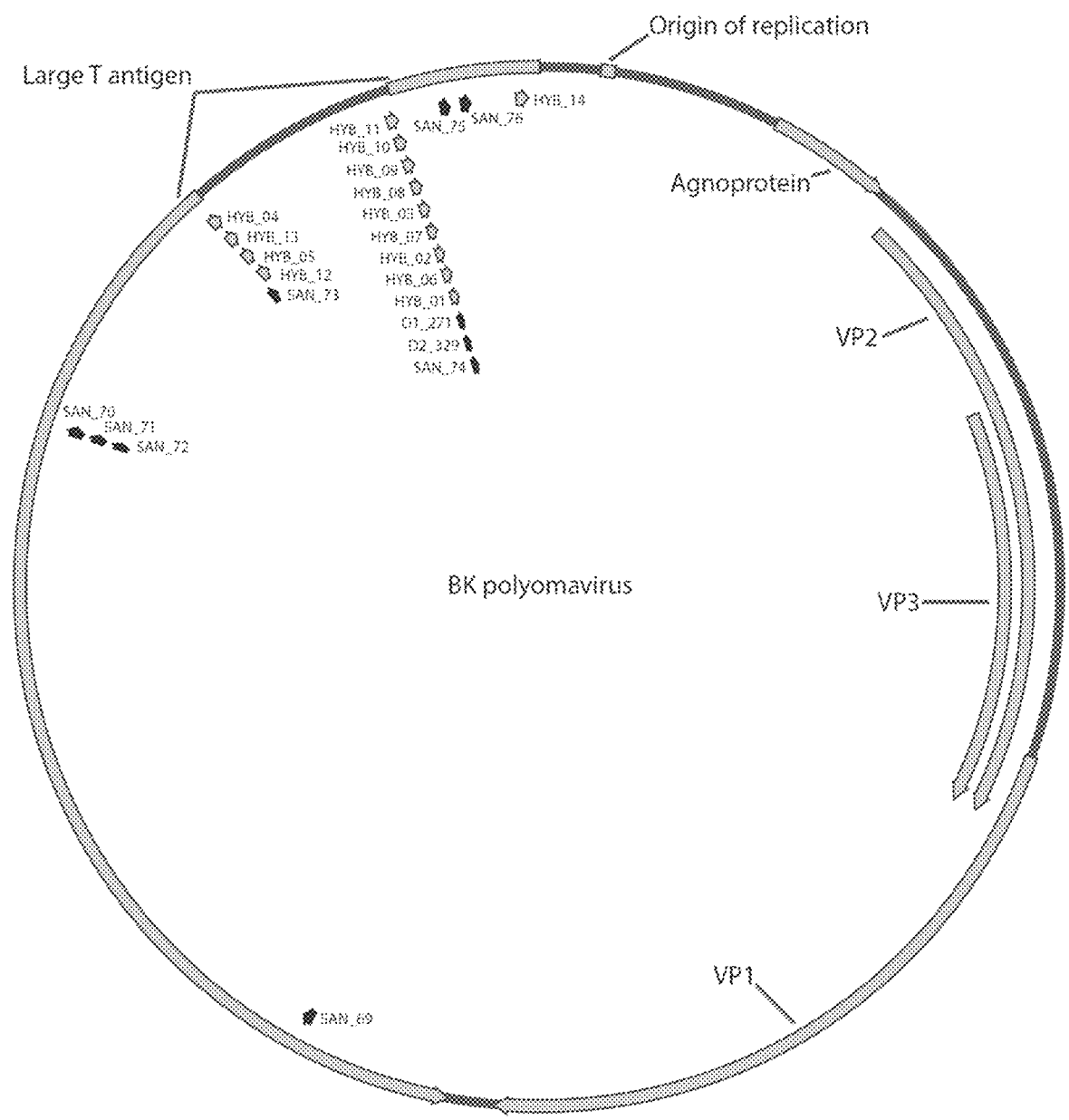
Fig. 10 (1)

| AON | Location | Sequence | SEQ ID NO |
|---|---|---|---|
| HYB_01 | 4909..4928 | ACCUCUGAGCUACUCCAGGU | 1 |
| HYB_02 | 4905..4924 | ACAAACCUCUGAGCUACUCC | 2 |
| HYB_03 | 4901..4920 | CAGCACAAACCUCUGAGCUA | 3 |
| HYB_04 | 4549..4568 | UGUUCCAUAGGUUGGCACCU | 5 |
| HYB_05 | 4552..4571 | UCCAUAGGUUGGCACCUAUA | 81 |
| HYB_06 | 4907..4926 | AAACCUCUGAGCUACUCCAG | 20 |
| HYB_07 | 4903..4922 | GCACAAACCUCUGAGCUACU | 21 |
| HYB_08 | 4899..4918 | AUCAGCACAAACCUCUGAGC | 22 |
| HYB_09 | 4897..4916 | AAAUCAGCACAAACCUCUGA | 23 |
| HYB_10 | 4895..4914 | GAAAUCAGCACAAACCUCU | 24 |
| HYB_11 | 4893..4912 | AGGAAAUCAGCACAAACCU | 25 |
| HYB_12 | 4554..4573 | CAUAGGUUGGCACCUAUAAA | 26 |
| HYB_13 | 4551..4570 | UUCCAUAGGUUGGCACCUAU | 27 |
| HYB_14 | 5114..5133 | UGAGCUCCAUGGAUUCUUCC | 28 |

Fig. 10 (2)

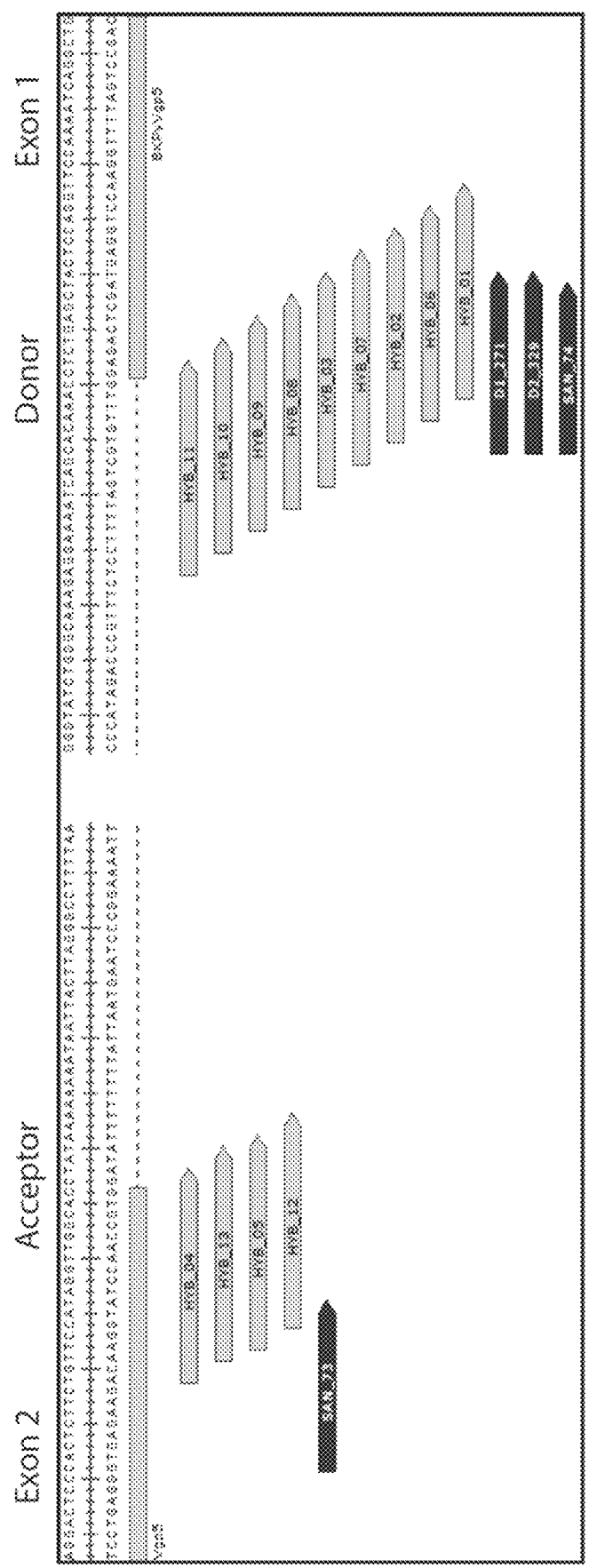
Fig. 10 (3)

```
┌ ANY-2
│ MT-29
│ MT
│ TW-1b
├ KOM-6
├ ANY-38
│ NAR-16
│ MT-18
│   ┌ NOY-5
│  ─┤
│   └ NEC-12
│ MT-7
│ ANY-13
│ APJ
├ OKN-42
│ THK-9
├ NAR-21
│ SHA-7
│ MT-87
├ NAR-9
│ NEB-6
├ SHA-13
│ NAR-13
│ SHA-4
│ MT-32
├─ SHA-23
│ NEC-7
│ MT-44
├ OKN-14
│ TW-1a
├ FUJ-6
│ TW-2
│ NAR-41
├ NEC-15
│ NEC-8
│  ┌ FUJ-4
│  │ TW-4
├ FUJ-36
│   ┌ ANY-57
│  ─┤
│   └ ANY-3
│ MT-51
│ TW-5
├ ANY-29
│ NAR-15
│ FUJ-31
│  ┌ MT-111
│  │ MT-11
│  │ MT-97
│  └ MT-8
│ NEC-22
│ SHA-9
│ MT-50
│ THK-6
```

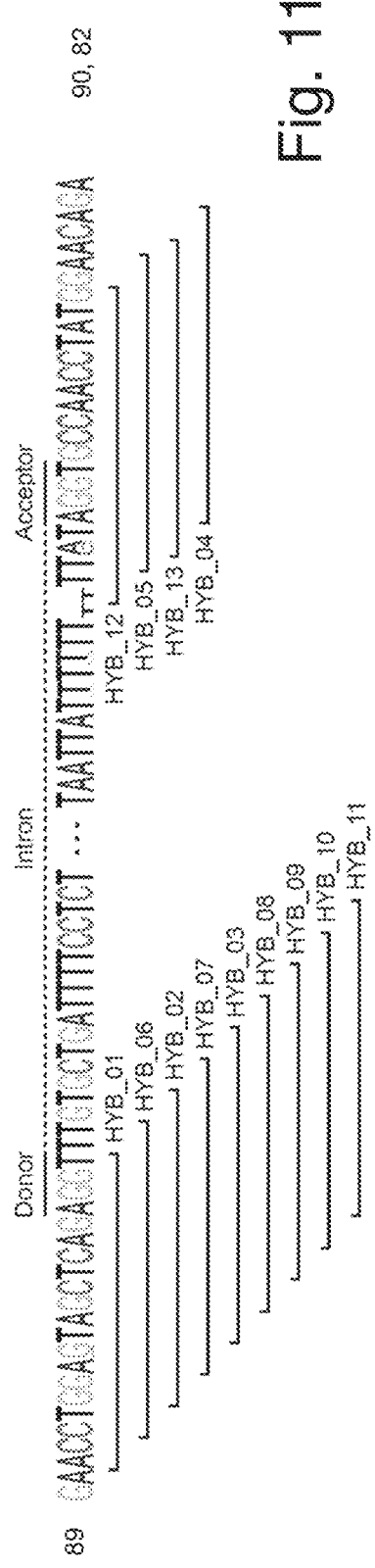
Fig. 11 (2)

| AON | Location | Sequence | SEQ ID NO |
|---|---|---|---|
| HYB_01 | 4909..4928 | ACCUCUGAGCUACUCCAGGU | 1 |
| HYB_02 | 4905..4924 | ACAAACCUCUGAGCUACUCC | 2 |
| HYB_03 | 4901..4920 | CAGCACAAACCUCUGAGCUA | 3 |
| HYB_04 | 4549..4568 | UGUUCCAUAGGUUGGCACCU | 5 |
| HYB_05 | 4552..4571 | UCCAUAGGUUGGCACCUAUA | 81 |
| HYB_06 | 4907..4926 | AAACCUCUGAGCUACUCCAG | 20 |
| HYB_07 | 4903..4922 | GCACAAACCUCUGAGCUACU | 21 |
| HYB_08 | 4899..4918 | AUCAGCACAAACCUCUGAGC | 22 |
| HYB_09 | 4897..4916 | AAAUCAGCACAAACCUCUGA | 23 |
| HYB_10 | 4895..4914 | GAAAAUCAGCACAAACCUCU | 24 |
| HYB_11 | 4893..4912 | AGGAAAAUCAGCACAAACCU | 25 |
| HYB_12 | 4551..4570 | CAUAGGUUGGCACCUAUAAA | 26 |
| HYB_13 | 4451..4570 | UUCCAUAGGUUGGCACCUAU | 27 |

Fig. 11 (3)

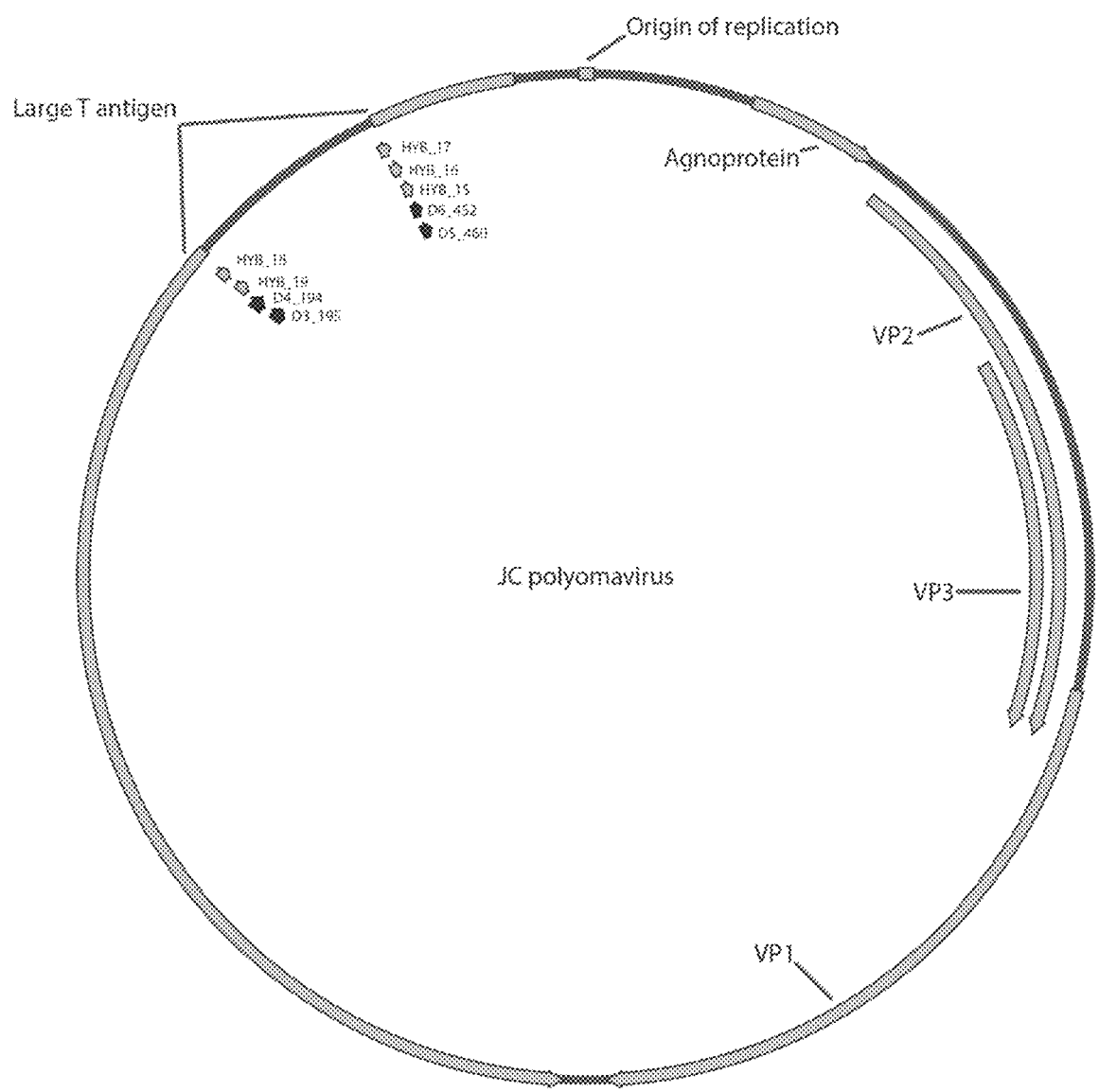
| AON | Location | Sequence | SEQ ID NO |
|---|---|---|---|
| HYB_15 | 4769..4788 | ACCUCUGAACUAUUCCAUGU | 6 |
| HYB_16 | 4765..4784 | ACCAACCUCUGAACUAUUCC | 7 |
| HYB_17 | 4761..4780 | CACAACCAACCUCUGAACUA | 8 |
| HYB_18 | 4409..4428 | UGUUCCAUAGGUUGGCACCU | 10 |
| HYB_19 | 4412..4431 | UCCAUAGGUUGGCACCUAAA | 9 |
Fig. 37 (1)

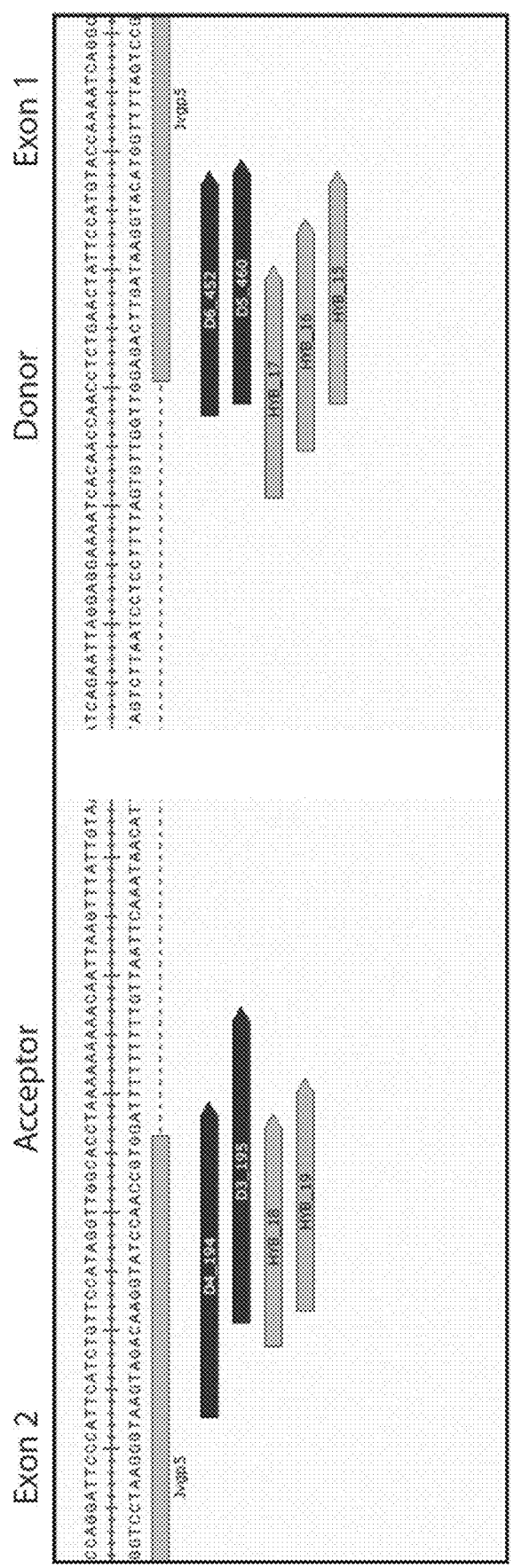
Fig. 37 (2)

INHIBITION OF POLYOMAVIRUS REPLICATION

RELATED APPLICATIONS

This application is a 35 U.S.C. § 371 filing of International Patent Application No. PCT/NL2019/050131, filed Mar. 1, 2019, which claims priority to European Patent Application No. 18159797.2, filed Mar. 2, 2018, the entire disclosures of which are hereby incorporated herein by reference.

SUBMISSION OF SEQUENCE LISTING

The contents of the electronic submission of the text file Sequence Listing, which is titled 715565_LUMC9-001US_ST.txt, which was created on Apr. 19, 2022 and is 18.3 KB in size, is incorporated herein by reference in its entirety.

The invention relates to molecules that specifically bind to polyomavirus RNA. In some embodiments molecules comprise antisense oligonucleotides that recognize pre-mRNA with a coding region of a T antigen of a polyomavirus. Examples of polyomaviruses are the human polyomaviruses such as JC virus (JCV), BK virus (BKV) or Merkel cell virus (MCV).

Polyomaviruses are small non-enveloped double-stranded DNA viruses whose natural hosts are normally mammals and birds. Infections in adults are mostly asymptomatic but can become pathological when the immune system is compromised. Non-limiting examples of human polyomaviruses are BK virus, JC virus and Merkel cell virus.

JCV and BKV are both opportunistic pathogens which infect the human population during early childhood (Leploeg, M. D. et. al., Clinical Infectious Diseases, 2001). The sero-prevalence in adults is high. Both viruses are thought to remain latent in kidney cells of the host (Wunderink, H. F. et. al., American Journal of Transplantation, 2017). Reactivation can occur, for instance, in immunosuppressed individuals (Wunderink, H. F. et. al., American Journal of Transplantation, 2017; Parajuli, S. et. al., Clinical Transplantation, 2018; Gard, L. et. al., PLoS One, 2017).

Polyomaviruses share a common genome structure. They have genes that are expressed both early and late in the infection cycle. Both early and late genes produce RNAs from which through differential splicing, various proteins can be stranslated. As shown in FIG. 1, the late RNAs typically encode the three capsid proteins whereas the early genes code for the small and large T-antigens and often one or more other alternatively spliced coding regions (Helle, F. et. al., Viruses, 2017).

WO2015/042466 describes an antisense oligonucleotide-based approach to inhibit JC virus replication and multiplication. The antisense oligonucleotides disclosed therein can be either oligodeoxyribonucleotides (ODNs) or be chimeric oligonucleotides that have an ODN interior flanked by one or more nucleotides with a nuclease resistant backbone. The latter render an RNA:oligonucleotide hybrid sensitive to the action of RNaseH. The deoxyribonucleotides interior has at least 4 deoxyribonucleotides and is flanked by nuclease resistant regions that have 2'-sugar-modified nucleotides. The antisense oligonucleotides are directed towards specific sequences that are present in JC virus mRNA.

In some embodiments, the present invention provides antisense oligonucleotides that can modulate splicing of a polyomavirus T-antigen pre-mRNA. Antisense oligonucleotides may have a sequence that is complementary to a splice donor site and/or a splice acceptor site in said pre-mRNA. Antisense oligonucleotides may have a sequence that is complementary to one or more exon-adjacent intron nucleobases (see FIG. 2). In some embodiments the antisense oligonucleotide renders a duplex of the antisense oligonucleotide with its polyomavirus T-antigen pre-mRNA target resistant to the action of RNaseH.

SUMMARY OF THE INVENTION

The invention provides an antisense oligonucleotide 12 to 30, preferably 17, 18, 19 or 20 to 30 nucleobases in length which comprises a sequence that is the reverse complement of a contiguous stretch of at least 12 nucleobases of a polyomavirus large T-antigen pre-mRNA and which antisense oligonucleotide can modulate splicing of said large T-antigen pre-mRNA in a cell (see FIG. 1).

Splice modulating antisense oligonucleotides of the present invention typically require a contiguous stretch of at least 17, preferably at least 18, more preferably at least 19 and more preferably at least 20 nucleobases complementary to the polyomavirus large T-antigen pre-mRNA.

The invention also provides an antisense oligonucleotide 12 to 30, preferably 17, 18, 19 or 20 to 30 nucleobases in length which comprises a sequence that is the reverse complement of a contiguous stretch of at least 12 nucleobases of a polyomavirus large T-antigen pre-mRNA, which stretch comprises a splice donor, a splice acceptor sequence or a combination thereof in said pre-mRNA. The splice donor or acceptor sequence is preferably a polyomavirus large T antigen splice acceptor or a polyomavirus large T antigen splice donor sequence.

Further provided is an antisense oligonucleotide 12 to 30, preferably 17, 18, 19 or 20 to 30 nucleobases in length, that is at least 80% complementary to nucleotides 4537-4596 or 4881-4940 taken from NC_001538 and at least comprising complementarity to the splice donor or splice acceptor sequence in the respective regions.

Also provided is an antisense oligonucleotide of 12 to 30, preferably 17, 18, 19 or 20 to 30 nucleobases in length that is preferably at least 80% complementary to nucleotides in the region 4397-4456 or the region 4741-4800 taken from NC_001699 and at least comprising complementarity to the splice donor or splice acceptor sequence in the respective regions.

Also provided is an antisense oligonucleotide of 12 to 30, preferably 17, 18, 19 or 20 to 30 nucleobases in length that is preferably at least 80% complementary to nucleotides in the region 4299-4358 or the region 4686-4745 taken from NC_009238 and at least comprising complementarity to the splice donor or splice acceptor sequence in the respective regions.

Also provided is an antisense oligonucleotide of 12 to 30, preferably 17, 18, 19 or 20 to 30 nucleobases in length that is preferably at least 80% complementary to nucleotides in the region 4477-4536 or the region 4876-4935 taken from NC_009539 and at least comprising complementarity to the splice donor or splice acceptor sequence in the respective regions.

Also provided is an antisense oligonucleotide of 12 to 30, preferably 17, 18, 19 or 20 to 30 nucleobases in length that is preferably at least 80% complementary to nucleotides in the region 4693-4752 or the region 5124-5183 taken from NC_010277 and at least comprising complementarity to the splice donor or splice acceptor sequence in the respective regions.

Also provided is an antisense oligonucleotide of 12 to 30, preferably 17, 18, 19 or 20 to 30 nucleobases in length that is preferably at least 80% complementary to nucleotides in the region 4264-4323 or the region 4654-4713 taken from NC_014406 and at least comprising complementarity to the splice donor or splice acceptor sequence in the respective regions.

Also provided is an antisense oligonucleotide of 12 to 30, preferably 17, 18, 19 or 20 to 30 nucleobases in length that is preferably at least 80% complementary to nucleotides in the region 4272-4331 or the region 4677-4736 taken from NC_014407 and at least comprising complementarity to the splice donor or splice acceptor sequence in the respective regions.

Also provided is an antisense oligonucleotide of 12 to 30, preferably 17, 18, 19 or 20 to 30 nucleobases in length that is preferably at least 80% complementary to nucleotides in the region 4352-4411 or the region 4765-4824 taken from NC_014361 and at least comprising complementarity to the splice donor or splice acceptor sequence in the respective regions.

Also provided is an antisense oligonucleotide of 12 to 30, preferably 17, 18, 19 or 20 to 30 nucleobases in length that is preferably at least 80% complementary to nucleotides in the region 4408-4467 or the region 4760-4819 taken from NC_015150 and at least comprising complementarity to the splice donor or splice acceptor sequence in the respective regions.

Also provided is an antisense oligonucleotide of 12 to 30, preferably 17, 18, 19 or 20 to 30 nucleobases in length that is preferably at least 80% complementary to nucleotides in the region 4303-4362 or the region 4658-4717 taken from NC_018102 and at least comprising complementarity to the splice donor or splice acceptor sequence in the respective regions.

Also provided is an antisense oligonucleotide of 12 to 30, preferably 17, 18, 19 or 20 to 30 nucleobases in length that is preferably at least 80% complementary to nucleotides in the region 4159-4218 or the region 4504-4563 taken from NC_020106 and at least comprising complementarity to the splice donor or splice acceptor sequence in the respective regions.

Also provided is an antisense oligonucleotide of 12 to 30, preferably 17, 18, 19 or 20 to 30 nucleobases in length that is preferably at least 80% complementary to nucleotides in the region 4392-4451 or the region 4791-4850 taken from NC_020890 and at least comprising complementarity to the splice donor or splice acceptor sequence in the respective regions.

Also provided is an antisense oligonucleotide of 12 to 30, preferably 17, 18, 19 or 20 to 30 nucleobases in length that is preferably at least 80% complementary to nucleotides in the region 4471-4530 or the region 4859-4918 taken from NC_024118 and at least comprising complementarity to the splice donor or splice acceptor sequence in the respective regions.

An antisense oligonucleotide as described herein preferably comprises at least 12 contiguous nucleobases of SEQ ID NO: 1; SEQ ID NO: 2; SEQ ID NO: 3; SEQ ID NO: 4; SEQ ID NO: 5; SEQ ID NO: 6; SEQ ID NO: 7; SEQ ID NO: 8; SEQ ID NO: 9; SEQ ID NO: 10; SEQ ID NO: 11; SEQ ID NO: 12; SEQ ID NO: 13; SEQ ID NO: 14; SEQ ID NO: 15; SEQ ID NO: 16; SEQ ID NO: 17; SEQ ID NO: 18; SEQ ID NO: 20; SEQ ID NO: 21; SEQ ID NO: 22; SEQ ID NO: 23; SEQ ID NO: 24; SEQ ID NO: 25; SEQ ID NO: 26 or SEQ ID NO: 27, wherein the at least twelve nucleotides preferably comprise the reverse complement of the splice donor site, splice acceptor site or combination thereof of the target pre-mRNA, i.e. the splice donor/acceptor of the large T-antigen pre-mRNA of the respective polyomavirus. In a preferred embodiment the antisense oligonucleotide as described herein comprises at least 17, preferably at least 18, preferably at least 19 and more preferably at least 20 contiguous nucleobases of SEQ ID NO: 1; SEQ ID NO: 2; SEQ ID NO: 3; SEQ ID NO: 4; SEQ ID NO: 5; SEQ ID NO: 6; SEQ ID NO: 7; SEQ ID NO: 8; SEQ ID NO: 9; SEQ ID NO: 10; SEQ ID NO: 11; SEQ ID NO: 12; SEQ ID NO: 13; SEQ ID NO: 14; SEQ ID NO: 15; SEQ ID NO: 16; SEQ ID NO: 17; SEQ ID NO: 18; SEQ ID NO: 20; SEQ ID NO: 21; SEQ ID NO: 22; SEQ ID NO: 23; SEQ ID NO: 24; SEQ ID NO: 25; SEQ ID NO: 26 or SEQ ID NO: 27; preferably SEQ ID NO: 1; SEQ ID NO: 2; SEQ ID NO: 3; SEQ ID NO: 4; SEQ ID NO: 6; SEQ ID NO: 7; SEQ ID NO: 8; SEQ ID NO: 9; SEQ ID NO: 10; SEQ ID NO: 20; SEQ ID NO: 21; SEQ ID NO: 22; SEQ ID NO: 23; SEQ ID NO: 24 or SEQ ID NO: 25; preferably SEQ ID NO: 1; SEQ ID NO: 2; SEQ ID NO: 3; SEQ ID NO: 4; SEQ ID NO: 20; SEQ ID NO: 21; SEQ ID NO: 22; SEQ ID NO: 23; SEQ ID NO: 24 or SEQ ID NO: 25, wherein the nucleotides preferably comprise the reverse complement of the splice donor site, splice acceptor site or combination thereof of the target pre-mRNA, i.e. the splice donor/acceptor of the large T-antigen pre-mRNA of the respective polyomavirus. An antisense oligonucleotide may have one mismatch with the indicated sequence, the mismatch is not at the start or the end of the contiguous stretch as an AON with a contiguous stretch of 17 nucleotides, for instance, with a mismatch at position one or 17 would actually have a contiguous stretch of 16 nucleotides.

Also provided is a method of inhibiting polyomavirus replication in a cell, the method comprising providing a cell that is infected with said polyomavirus with an antisense oligonucleotide of the invention that is specific for the polyomavirus.

The invention further provides a method of preparing a graft for transplantation, the method characterized in that donor cells, preferably donor kidney cells are provided with an antisense oligonucleotide of the invention that is specific for the polyomavirus.

Also provided is a method of treatment of a polyomavirus infection in a subject, the method comprising administering an antisense oligonucleotide of the invention that is specific for the polyomavirus, to the individual in need thereof.

Further provided is a method of administering an antisense oligonucleotide to an individual, for hybridization to a complementary RNA sequence in a cell of said individual, the method characterized in that the antisense oligonucleotide is a chimeric antisense oligonucleotide comprising a first and a second region, and wherein said first region comprises one or more deoxyribonucleotides and said second region comprises at least one 2'-O-(2-methoxy-ethyl) nucleotide (see FIG. 7).

Further provided is a method of inhibiting replication of a polyomavirus in a cell, the method comprising providing said cell with an antisense oligonucleotide 12 to 30 nucleotides in length which comprises a sequence that is the reverse complement of a contiguous stretch of at least 12 nucleobases of a polyomavirus large T-antigen pre-mRNA and which antisense oligonucleotide can modulate the splicing of said large T-antigen pre-mRNA. Said antisense oligonucleotide is preferably an antisense oligonucleotide as described herein, preferably an antisense oligonucleotide of SEQ ID NO: 1-25 as described or modified herein.

DETAILED DESCRIPTION OF THE INVENTION

The term "antisense oligonucleotide' refers to an oligomer or polymer of ribonucleic acid (RNA) or deoxyribonucleic acid (DNA), or mimetics, chimeras, analogs and homologs thereof. This term includes antisense oligonucleotides composed of naturally occurring nucleobases, sugars, and covalent internucleoside (backbone) linkages as well as antisense oligonucleotides having non-naturally occurring portions which function similarly. Such modified or substituted antisense oligonucleotides are often preferred over native forms because of desirable properties such as, for example, enhanced cellular uptake, enhanced affinity for a target nucleic acid, and increased stability in the presence of nucleases (see FIG. 7).

An antisense oligonucleotide as described herein is preferably a single-stranded antisense oligonucleotide.

Antisense oligonucleotides of the present invention also include modified antisense oligonucleotides in which a different base is present at one or more of the nucleotide positions in the antisense oligonucleotide. For example, if the first nucleotide is an adenosine, modified antisense oligonucleotides may be produced that contain thymidine, guanosine or cytidine at this position. This may be done at any of the positions of the antisense oligonucleotide. These antisense oligonucleotides are then tested using the methods described herein to determine their ability to inhibit T-antigen RNA.

An antisense oligonucleotide of the present invention can hybridize to polyomavirus RNA produced upon infection of a susceptible cell. As such, the antisense oligonucleotide comprises a sequence that is the reverse complement of the sequence of (the part of) the target RNA. The antisense oligonucleotide may be introduced in the form of single-stranded, double-stranded, partially single-stranded, or circular oligomeric compound. In a preferred embodiment the antisense oligonucleotide is a single stranded antisense oligonucleotide.

The antisense oligonucleotide may be linked to one or more other chemical structures. The other structure may be a peptide or protein, a sugar, a lipid or other chemical structure. The other structure may also be one or more other nucleotides. The one or more other nucleotides may perform a function different from the antisense part. For instance, hybridization to another nucleic target sequence. The other structure may perform any of a number of one or more different functions. Non-limiting examples of such functions are stability of the antisense oligonucleotide, increase in bioavailability, increase in cell penetration, increase in nuclear delivery, targeting to specific cells and the like.

Once introduced into a system, the antisense oligonucleotides of the invention may elicit the action of one or more enzymes or structural proteins to effect modification of the target nucleic acid. It is known in the art that single-stranded antisense oligonucleotides that are "DNA-like' elicit RNase H, a cellular endonuclease which cleaves the RNA strand of an RNA:DNA duplex. Activation of RNase H, therefore, results in cleavage of the RNA target. This is one way to enhance the efficiency of antisense oligonucleotide-mediated inhibition of gene expression. In embodiments antisense oligonucleotides of the invention do not, and are not designed to, recruit the action of RNase H to the target RNA/antisense oligonucleotide hybrid. Similar roles have been postulated for other ribonucleases such as those in the RNase III and ribonuclease L family of enzymes. Antisense oligonucleotides as described herein preferably have modifications that confer nuclease resistance to the antisense oligonucleotide and the target RNA/antisense oligonucleotide hybrid. Specifically excluded from the definition of "antisense oligonucleotides" herein are ribozymes that contain internal or external "bulges" that do not hybridize to the target sequence.

An antisense oligonucleotide in accordance with the invention comprises of 12 to 30, preferably 17, 18, 19 or 20 to 30 nucleobases (i.e. of about 12 to and including 30 linked nucleosides). One of ordinary skill in the art will appreciate that the invention embodies antisense oligonucleotides of 12, 13, 14, 15, 16, 17, 18, 19, 20, 21, 22, 23, 24, 25, 26, 27, 28, 29 or 30 nucleobases in length. One having ordinary skill in the art will appreciate that this embodies antisense oligonucleotides of 15, 16, 17, 18, 19, 20, 21, 22, 23, 24, 25, 26, 27, 28, 29, or 30 nucleobases in length. One having ordinary skill in the art will appreciate that this embodies antisense oligonucleotides of 17, 18, 19, 20, 21, 22, 23, 24, 25 or 26 nucleobases in length. Often antisense oligonucleotides are 18, 19, 20, 21 or 22 nucleobases in length. Antisense oligonucleotides as described herein are preferably 17, 18, 19, 20, 21, or 22 nucleotides in length.

In one embodiment an antisense oligonucleotide comprises at least 12 contiguous nucleobases of a sequence of an oligonucleotide of which the sequence is specifically disclosed herein. Antisense oligonucleotides 12-30 nucleobases in length comprising a stretch of at least twelve (12) consecutive nucleobases selected from within the illustrative antisense oligonucleotides are considered to be suitable antisense oligonucleotides as well.

An antisense oligonucleotide comprises a sequence of nucleobases that is the reverse complement of the sequence of the target RNA. An antisense oligonucleotide as described herein comprises a stretch of at least 12 nucleobases with a sequence that is the reverse complement of the sequence of at least 12 contiguous nucleobases of the target RNA. The stretch is also referred to as the complementarity region or the hybridization region. One of ordinary skill in the art will appreciate that the invention embodies antisense oligonucleotides with a complementarity region of 12, 13, 14, 15, 16, 17, 18, 19, 20, 21, 22, 23, 24, 25, 26, 27, 28, 29 or 30 nucleobases in length. One of ordinary skill in the art will appreciate that the invention embodies antisense oligonucleotides with a complementarity region of 15, 16, 17, 18, 19, 20, 21, 22, 23, 24, 25, 26, 27, 28, 29 or 30 nucleobases in length. One of ordinary skill in the art will appreciate that the invention embodies antisense oligonucleotides with a complementarity region of 17, 18, 19, 20, 21, 22, 23, 24, 25 or 26 nucleobases in length. Often antisense oligonucleotides have a complementarity region of 18, 19, 20, 21 or 22 nucleobases in length. Antisense oligonucleotides as described herein preferably have a complementarity region of 17, 18, 19, 20, 21 or 22 nucleobases in length.

Antisense oligonucleotides preferably have a length that is commensurate to the length of the complementarity region.

The target sequence of an antisense oligonucleotide as described herein is a part of a polyomavirus T-antigen pre-mRNA. Pre-mRNA or precursor mRNA is an immature single strand of messenger ribonucleic acid (mRNA). Polyomavirus T-antigen pre-mRNA is synthesized from a polyomavirus DNA template in the cell nucleus by transcription. The pre-mRNA contains one or more introns that are spliced out during maturation of the pre-mRNA into mRNA. The splicing process removes introns from transcripts and joins exons together. Introns are typically flanked by a donor site (5' end of the intron) and an acceptor site (3' end of the intron). The splice sites are required for splicing and typically include an almost invariant sequence GU at the 5' end of the intron and a splice acceptor site at the 3' end of the intron with an almost invariant AG sequence. The GU and AG sequence and the intervening sequence are spliced out of the pre-mRNA. A characteristic of polyomavirus T-antigen pre-mRNA is that it can be alternatively spliced or not spliced leading to the generation of at least two and often 3, 4 or 5 differently spliced mRNAs (see FIG. 1). Virus propagation is dependent on the availability of the virus genome, the presence of virus proteins, the cellular machinery and particularly the delicate interplay between the various stages and components. The splicing process of virus RNAs is an important method for regulating the virus propagation process, and influences the level and likely also the timing of certain products being formed in the cells. In the present invention it was surprisingly found that directing an oligonucleotide of the invention to a splice donor or splice acceptor site for splicing of large T-antigen mRNA has a profound effect not only on the production of T-antigen mRNA, but also on the level capsid protein produced and the production of virus by the infected cell.

The target sequence of an antisense oligonucleotide as described herein comprises a splice donor site of a polyomavirus T-antigen pre-mRNA, a splice acceptor site of a polyomavirus T-antigen pre-mRNA or a combination thereof. The target sequence typically comprises a stretch of 12 contiguous nucleobases comprising a splice donor site of a polyomavirus T-antigen pre-mRNA or a splice acceptor site of a polyomavirus T-antigen pre-mRNA. The contiguous sequence preferably comprises an intron sequence in addition to the splice donor or the splice acceptor sequence. In a preferred embodiment the contiguous sequence comprises one or two intron nucleobases adjacent to the splice donor or the splice acceptor sequence. In a preferred embodiment the contiguous sequence comprises 3, 4, 5, 6, 7, 8, 9, 10, 11, 12, 13, 14, 15, 16, 17, 18, 19, 20, 21, 22, 23, 24, 25, 26, 27 or 28 intron nucleobases adjacent to the splice donor or splice acceptor sequence. In a preferred embodiment the contiguous sequence comprises 1, 2, 3, 4, 5, 6, 7, 8, 9, 10, 11, 12, 13, 14, 15, 16, 17, 18, 19, 20, 21, 22, 23, 24, 25, 26, 27, or 28 exon nucleobases adjacent to the splice donor or the splice acceptor sequence. The antisense oligonucleotide preferably comprises a sequence that is the reverse complement of a contiguous sequence of nucleobases of the target pre-mRNA. The sum of the number of intron, splice site and exon nucleobases does not exceed the total number of nucleobases in the antisense oligonucleotide.

The target sequence preferably comprises the splice donor sequence or the splice acceptor sequence that define the intron that is otherwise spliced out to produce mRNA that codes for the large T-antigen of the specific polyomavirus (see FIG. 8).

The sequence of an antisense oligonucleotide as described herein comprises complementarity to the splice donor sequence or the splice acceptor sequence that define the intron that is otherwise spliced out to produce mRNA that codes for the large T-antigen of the specific polyomavirus (see FIG. 8).

In a preferred embodiment the target sequence of a first oligonucleotide is a sequence in the 3' splice site target region indicated below for the respective viruses. In a preferred embodiment the target sequence of another oligonucleotide is a sequence in the 5' splice site target region indicated below for the respective viruses. An oligonucleotide that is directed towards a target sequence in a region indicated below comprises the complementary sequence of the splice donor or splice acceptor in the indicated sequence. If more than one AON is used in a method as described herein it is preferred that the AONs are directed towards a target sequence of the same virus.

| Abbreviation | Accession | 3' splice site target region | 5' splice site target region |
|---|---|---|---|
| BKPyV | NC_001538 | 4537-4596 | 4881-4940 |
| JCPyV | NC_001699 | 4397-4456 | 4741-4800 |
| KIPyV | NC_009238 | 4299-4358 | 4686-4745 |
| WUPyV | NC_009539 | 4477-4536 | 4876-4935 |
| MCPyV | NC_010277 | 4693-4752 | 5124-5183 |
| HPyV6 | NC_014406 | 4264-4323 | 4654-4713 |
| HPyV7 | NC_014407 | 4272-4331 | 4677-4736 |
| TSPyV | NC_014361 | 4352-4411 | 4765-4824 |
| HPyV9 | NC_015150 | 4408-4467 | 4760-4819 |
| MWPyV | NC_018102 | 4303-4362 | 4658-4717 |
| STLPyV | NC_020106 | 4159-4218 | 4504-4563 |
| HPyV12 | NC_020890 | 4392-4451 | 4791-4850 |
| NJPyV | NC_024118 | 4471-4530 | 4859-4918 |

The first column contains an abbreviation of the virus name. A prototype sequence for the virus is indicated with the accession code for the sequence in the sequence database. The third and fourth columns specifies a region in the prototype virus sequence that contains the splice donor (column 4) or splice acceptor (column 3) to which an AON as described herein can comprise a complementarity region.

An antisense oligonucleotide according to the invention may modulate the splicing of T-antigen pre-mRNA in the infected cell. Without being bound by theory it is believed that an antisense oligonucleotide as described herein inhibits usage of the splice site it is targeted to. The resultant reduced production of large T-antigen impacts the expression of the capsid proteins and thereby the production of virus (see FIGS. 4-6). Without being bound by theory it is believed that the imbalance of T-antigen specific splice products induced by the antisense oligonucleotides of the invention has a more pronounced effect on virus propagation than the reduction of T-antigen mRNA specific mRNA by RNAi-like approaches.

In the context of this invention, "hybridization" means the pairing of complementary strands of nucleic acid. In the present invention, the preferred mechanism of pairing involves hydrogen bonding, which may be Watson-Crick, Hoogsteen or reversed Hoogsteen hydrogen bonding, between complementary nucleoside or nucleotide bases (nucleobases). For example, adenine and thymine are complementary nucleobases that pair through the formation of hydrogen bonds. Hybridization can occur under varying circumstances. Hybridization of complementary strands typically improves with the length of the sequence. Specific hybridization of two strands is accomplished with a contiguous stretch of 12 or more complementary nucleobases. The sequence of an antisense oligonucleotide can be, but need not necessarily be, 100% complementary to that of its target sequence to be specifically hybridizable. Moreover, an antisense oligonucleotide may hybridize over one or more segments such that intervening or adjacent segments are not involved in the hybridization event. In one embodiment of this invention, the antisense oligonucleotide of the present invention comprises at least 70%, or at least 75%, or at least 80%, or at least 85% sequence complementarity to a target region within the target pre-mRNA. In other embodiments, the antisense oligonucleotide of the present invention comprises at least 90% sequence complementarity and even comprise at least 95% or at least 96% sequence complementarity to the target region within the target pre-mRNA. For example, an antisense compound in which 18 of 20 nucleobases of the antisense compound are complementary to a target region, and would therefore specifically hybridize, would represent 90 percent complementarity. When an antisense oligonucleotide of 18 nucleotides has a sequence that is the reverse complement of a contiguous stretch of at least 12 nucleobases of a polyomavirus large T-antigen pre-mRNA, the remaining 6 complementary nucleobases may be clustered with the 12 or not be contiguous with the 12. Percent complementarity of an antisense oligonucleotide with a region of a target pre-mRNA can be determined routinely using BLAST programs (basic local alignment search tools) and PowerBLAST programs known in the art (Altschul et al., J. Mol. Biol., 1990, 215, 403-410; Zhang and Madden, Genome Res., 1997, 7,649-656). As the number of nucleotides is always an integer, the actual percentage may be not be exactly 90% or not exactly 96%. The contiguous sequence preferably has no or only one nucleotide mismatch with the target nucleic acid sequence.

An antisense oligonucleotide of 12 to 30, preferably 17, 18, 19 or 20 to 30 nucleobases in length is preferably at least 80% complementary to nucleotides in the region 4537-4596 or the region 4881-4940 taken from NC_001538 and at least comprising complementarity to the splice donor or splice acceptor sequence in the respective regions, preferably at least 90% complementary to nucleotides 4537-4596 or 4881-4940 taken from NC_001538. The 12 to 30, preferably 17, 18, 19 or 20 to 30 nucleobases are preferably complementary to a stretch of at least 12, 13, 14, 15, 16, 17, 18, 19, 30, 21, 22, 23, 24, 25, 26, 27, 28, 29 or 30 contiguous nucleotides of the target pre-mRNA. In a preferred embodiment the oligonucleotide is 12 to 30, preferably 17, 18, 19 or 20 to 30 nucleobases in length and preferably comprises a sequence as set forth in SEQ ID NO: 1; SEQ ID NO: 2; SEQ ID NO: 3; SEQ ID NO: 4; SEQ ID NO: 5; SEQ ID NO: 20; SEQ ID NO: 21; SEQ ID NO: 22; SEQ ID NO: 23; SEQ ID NO: 24; SEQ ID NO: 25; SEQ ID NO: 26 or SEQ ID NO: 27; preferably as set forth in SEQ ID NO: 1; SEQ ID NO: 2; SEQ ID NO: 3; SEQ ID NO: 4; SEQ ID NO: 6; SEQ ID NO: 7; SEQ ID NO: 8; SEQ ID NO: 9; SEQ ID NO: 10; SEQ ID NO: 20; SEQ ID NO: 21; SEQ ID NO: 22; SEQ ID NO: 23; SEQ ID NO: 24 or SEQ ID NO: 25; preferably as set forth in SEQ ID NO: 1; SEQ ID NO: 2; SEQ ID NO: 3; SEQ ID NO: 4; SEQ ID NO: 20; SEQ ID NO: 21; SEQ ID NO: 22; SEQ ID NO: 23; SEQ ID NO: 24 or SEQ ID NO: 25.

An antisense oligonucleotide of 12 to 30, preferably 17, 18, 19 or 20 to 30 nucleobases in length is preferably at least 80% complementary to nucleotides in the region 4397-4456 or the region 4741-4800 taken from NC_001699 and at least comprising complementarity to the splice donor or splice acceptor sequence in the respective regions, preferably at least 90% complementary to nucleotides 4397-4456 or the region 4741-4800 taken from NC_001699. The 12 to 30, preferably 17, 18, 19 or 20 to 30 nucleobases are preferably complementary to a stretch of at least 12, 13, 14, 15, 16, 17, 18, 19, 30, 21, 22, 23, 24, 25, 26, 27, 28, 29 or 30 contiguous nucleotides of the target pre-mRNA.

An antisense oligonucleotide of 12 to 30, preferably 17, 18, 19 or 20 to 30 nucleobases in length is preferably at least 80% complementary to nucleotides in the region 4299-4358 or the region 4686-4745 taken from NC_009238 and at least comprising complementarity to the splice donor or splice acceptor sequence in the respective regions, preferably at least 90% complementary to nucleotides 4299-4358 or the region 4686-4745 taken from NC_009238. The 12 to 30, preferably 17, 18, 19 or 20 to 30 nucleobases are preferably complementary to a stretch of at least 12, 13, 14, 15, 16, 17, 18, 19, 30, 21, 22, 23, 24, 25, 26, 27, 28, 29 or 30 contiguous nucleotides of the target pre-mRNA.

An antisense oligonucleotide of 12 to 30, preferably 17, 18, 19 or 20 to 30 nucleobases in length is preferably at least 80% complementary to nucleotides in the region 4477-4536 or the region 4876-4935 taken from NC_009539 and at least comprising complementarity to the splice donor or splice acceptor sequence in the respective regions, preferably at least 90% complementary to nucleotides 4477-4536 or the region 4876-4935 taken from NC_009539. The 12 to 30, preferably 17, 18, 19 or 20 to 30 nucleobases are preferably complementary to a stretch of at least 12, 13, 14, 15, 16, 17, 18, 19, 30, 21, 22, 23, 24, 25, 26, 27, 28, 29 or 30 contiguous nucleotides of the target pre-mRNA.

An antisense oligonucleotide of 12 to 30, preferably 17, 18, 19 or 20 to 30 nucleobases in length is preferably at least 80% complementary to nucleotides in the region 4693-4752 or the region 5124-5183 taken from NC_010277 and at least comprising complementarity to the splice donor or splice acceptor sequence in the respective regions, preferably at least 90% complementary to nucleotides 4693-4752 or the region 5124-5183 taken from NC_010277. The 12 to 30, preferably 17, 18, 19 or 20 to 30 nucleobases are preferably complementary to a stretch of at least 12, 13, 14, 15, 16, 17, 18, 19, 30, 21, 22, 23, 24, 25, 26, 27, 28, 29 or 30 contiguous nucleotides of the target pre-mRNA.

An antisense oligonucleotide of 12 to 30, preferably 17, 18, 19 or 20 to 30 nucleobases in length is preferably at least 80% complementary to nucleotides in the region 4264-4323 or the region 4654-4713 taken from NC_014406 and at least comprising complementarity to the splice donor or splice acceptor sequence in the respective regions, preferably at least 90% complementary to nucleotides 4264-4323 or the region 4654-4713 taken from NC_014406. The 12 to 30, preferably 17, 18, 19 or 20 to 30 nucleobases are preferably complementary to a stretch of at least 12, 13, 14, 15, 16, 17, 18, 19, 30, 21, 22, 23, 24, 25, 26, 27, 28, 29 or 30 contiguous nucleotides of the target pre-mRNA.

An antisense oligonucleotide of 12 to 30, preferably 17, 18, 19 or 20 to 30 nucleobases in length is preferably at least 80% complementary to nucleotides in the region 4272-4331 or the region 4677-4736 taken from NC_014407 and at least comprising complementarity to the splice donor or splice acceptor sequence in the respective regions, preferably at least 90% complementary to nucleotides 4272-4331 or the region 4677-4736 taken from NC_014407. The 12 to 30, preferably 17, 18, 19 or 20 to 30 nucleobases are preferably complementary to a stretch of at least 12, 13, 14, 15, 16, 17, 18, 19, 30, 21, 22, 23, 24, 25, 26, 27, 28, 29 or 30 contiguous nucleotides of the target pre-mRNA.

An antisense oligonucleotide of 12 to 30, preferably 17, 18, 19 or 20 to 30 nucleobases in length is preferably at least 80% complementary to nucleotides in the region 4352-4411 or the region 4765-4824 taken from NC_014361 and at least comprising complementarity to the splice donor or splice acceptor sequence in the respective regions, preferably at least 90% complementary to nucleotides 4352-4411 or the region 4765-4824 taken from NC_014361. The 12 to 30, preferably 17, 18, 19 or 20 to 30 nucleobases are preferably complementary to a stretch of at least 12, 13, 14, 15, 16, 17, 18, 19, 30, 21, 22, 23, 24, 25, 26, 27, 28, 29 or 30 contiguous nucleotides of the target pre-mRNA.

An antisense oligonucleotide of 12 to 30, preferably 17, 18, 19 or 20 to 30 nucleobases in length is preferably at least 80% complementary to nucleotides in the region 4408-4467 or the region 4760-4819 taken from NC_015150 and at least comprising complementarity to the splice donor or splice acceptor sequence in the respective regions, preferably at least 90% complementary to nucleotides 4408-4467 or the region 4760-4819 taken from NC_015150. The 12 to 30, preferably 17, 18, 19 or 20 to 30 nucleobases are preferably complementary to a stretch of at least 12, 13, 14, 15, 16, 17, 18, 19, 30, 21, 22, 23, 24, 25, 26, 27, 28, 29 or 30 contiguous nucleotides of the target pre-mRNA.

An antisense oligonucleotide of 12 to 30, preferably 17, 18, 19 or 20 to 30 nucleobases in length is preferably at least 80% complementary to nucleotides in the region 4303-4362 or the region 4658-4717 taken from NC_018102 and at least comprising complementarity to the splice donor or splice acceptor sequence in the respective regions, preferably at least 90% complementary to nucleotides 4303-4362 or the region 4658-4717 taken from NC_018102. The 12 to 30, preferably 17, 18, 19 or 20 to 30 nucleobases are preferably complementary to a stretch of at least 12, 13, 14, 15, 16, 17, 18, 19, 30, 21, 22, 23, 24, 25, 26, 27, 28, 29 or 30 contiguous nucleotides of the target pre-mRNA.

An antisense oligonucleotide of 12 to 30, preferably 17, 18, 19 or 20 to 30 nucleobases in length is preferably at least 80% complementary to nucleotides in the region 4159-4218 or the region 4504-4563 taken from NC_020106 and at least comprising complementarity to the splice donor or splice acceptor sequence in the respective regions, preferably at least 90% complementary to nucleotides 4159-4218 or the region 4504-4563 taken from NC_020106. The 12 to 30, preferably 17, 18, 19 or 20 to 30 nucleobases are preferably complementary to a stretch of at least 12, 13, 14, 15, 16, 17, 18, 19, 30, 21, 22, 23, 24, 25, 26, 27, 28, 29 or 30 contiguous nucleotides of the target pre-mRNA.

An antisense oligonucleotide of 12 to 30, preferably 17, 18, 19 or 20 to 30 nucleobases in length is preferably at least 80% complementary to nucleotides in the region 4392-4451 or the region 4791-4850 taken from NC_020890 and at least comprising complementarity to the splice donor or splice acceptor sequence in the respective regions, preferably at least 90% complementary to nucleotides 4392-4451 or the region 4791-4850 taken from NC_020890. The 12 to 30, preferably 17, 18, 19 or 20 to 30 nucleobases are preferably complementary to a stretch of at least 12, 13, 14, 15, 16, 17, 18, 19, 30, 21, 22, 23, 24, 25, 26, 27, 28, 29 or 30 contiguous nucleotides of the target pre-mRNA.

An antisense oligonucleotide of 12 to 30, preferably 17, 18, 19 or 20 to 30 nucleobases in length is preferably at least 80% complementary to nucleotides in the region 4471-4530 or the region 4859-4918 taken from NC_024118 and at least comprising complementarity to the splice donor or splice acceptor sequence in the respective regions, preferably at least 90% complementary to nucleotides 4471-4530 or the region 4859-4918 taken from NC_024118. The 12 to 30, preferably 17, 18, 19 or 20 to 30 nucleobases are preferably complementary to a stretch of at least 12, 13, 14, 15, 16, 17, 18, 19, 30, 21, 22, 23, 24, 25, 26, 27, 28, 29 or 30 contiguous nucleotides of the target pre-mRNA.

An antisense oligonucleotide as described herein preferably comprises at least 12 contiguous nucleobases of SEQ ID NO: 1; SEQ ID NO: 2; SEQ ID NO: 3; SEQ ID NO: 4; SEQ ID NO: 5; SEQ ID NO: 6; SEQ ID NO: 7; SEQ ID NO: 8; SEQ ID NO: 9; SEQ ID NO: 10; SEQ ID NO: 11; SEQ ID NO: 12; SEQ ID NO: 13; SEQ ID NO: 14; SEQ ID NO: 15; SEQ ID NO: 16; SEQ ID NO: 17; SEQ ID NO: 18; SEQ ID NO: 20; SEQ ID NO: 21; SEQ ID NO: 22; SEQ ID NO: 23; SEQ ID NO: 24; SEQ ID NO: 25; SEQ ID NO: 26 or SEQ ID NO: 27 preferably of SEQ ID NO: 1; SEQ ID NO: 2; SEQ ID NO: 3; SEQ ID NO: 4; SEQ ID NO: 6; SEQ ID NO: 7; SEQ ID NO: 8; SEQ ID NO: 9; SEQ ID NO: 10; SEQ ID NO: 20; SEQ ID NO: 21; SEQ ID NO: 22; SEQ ID NO: 23; SEQ ID NO: 24 or SEQ ID NO: 25; preferably of SEQ ID NO: 1; SEQ ID NO: 2; SEQ ID NO: 3; SEQ ID NO: 4; SEQ ID NO: 20; SEQ ID NO: 21; SEQ ID NO: 22; SEQ ID NO: 23; SEQ ID NO: 24 or SEQ ID NO: 25, wherein the at least twelve nucleotides preferably comprise the reverse complement of the splice donor site, splice acceptor site or combination thereof of the target pre-mRNA, i.e. the splice donor/acceptor of the large T-antigen pre-mRNA of the respective polyomavirus. The reverse complement is present in the respective SEQ IDs.

The invention further relates to an antisense oligonucleotide comprising at least 12 contiguous nucleobases of the nucleotide sequence (see FIG. 3 and FIG. 10):

SEQ ID NO: 1
5' ACCUCUGAGCUACUCCAGGU 3';

SEQ ID NO: 2
5' ACAAACCUCUGAGCUACUCC 3';

SEQ ID NO: 3
5' CAGCACAAACCUCUGAGCUA 3';

SEQ ID NO: 4
5' UCCAUAGGUUGGCACCUAGA 3';

SEQ ID NO: 5
5' UGUUCCAUAGGUUGGCACCU 3';

SEQ ID NO: 20
5' AAACCUCUGAGCUACUCCAG 3';

SEQ ID NO: 21
5' GCACAAACCUCUGAGCUACU 3';

SEQ ID NO: 22
5' AUCAGCACAAACCUCUGAGC 3;

SEQ ID NO: 23
5' AAAUCAGCACAAACCUCUGA 3';

SEQ ID NO: 24
5' GAAAAUCAGCACAAACCUCU 3';

SEQ ID NO: 25
5' AGGAAAAUCAGCACAAACCU 3';

SEQ ID NO: 26
5' CAUAGGUUGGCACCUAUAAA 3'
or

SEQ ID NO: 27
5' UUCCAUAGGUUGGCACCUAU 3.

An antisense oligonucleotide as described herein preferably comprises at least 13, 14, 15, 16, 17, 18, 19 or 20 contiguous nucleobases of SEQ ID NO: 1; SEQ ID NO: 2; SEQ ID NO: 3; SEQ ID NO: 4; SEQ ID NO: 5; SEQ ID NO: 6; SEQ ID NO: 7; SEQ ID NO: 8; SEQ ID NO: 9; SEQ ID NO: 10; SEQ ID NO: 11; SEQ ID NO: 12; SEQ ID NO: 13; SEQ ID NO: 14; SEQ ID NO: 15; SEQ ID NO: 16; SEQ ID NO: 17; SEQ ID NO: 18; SEQ ID NO: 20; SEQ ID NO: 21; SEQ ID NO: 22; SEQ ID NO: 23; SEQ ID NO: 24; SEQ ID NO: 25; SEQ ID NO: 26 or SEQ ID NO: 27; preferably of SEQ ID NO: 1; SEQ ID NO: 2; SEQ ID NO: 3; SEQ ID NO: 4; SEQ ID NO: 6; SEQ ID NO: 7; SEQ ID NO: 8; SEQ ID NO: 9; SEQ ID NO: 10; SEQ ID NO: 20; SEQ ID NO: 21; SEQ ID NO: 22; SEQ ID NO: 23; SEQ ID NO: 24 or SEQ ID NO: 25; preferably of SEQ ID NO: 1; SEQ ID NO: 2; SEQ ID NO: 3; SEQ ID NO: 4; SEQ ID NO: 20; SEQ ID NO: 21; SEQ ID NO: 22; SEQ ID NO: 23; SEQ ID NO: 24 or SEQ ID NO: 25, wherein the at least respectively 13, 14, 15, 16, 17, 18, 19 or 20 nucleotides preferably comprise the reverse complement of the splice donor site, splice acceptor site or combination thereof of the target pre-mRNA. A nucleobase as indicated herein may be substituted by a different nucleobase with same base pairing activity in kind not necessarily in amount. An example of such an alternative is the base thymidine as a substitute for uracil. Other nucleobases may be substituted for an alternative with the same kind of base pairing activity.

Another alternative are bases that pair with any base. An example of a base is inosine. Such bases do typically not add specificity to the oligonucleotide compared to a base that pairs with the appropriate base in the target RNA. Oligonucleotides can accommodate this to some extent as is known to the person skilled in the art. If the same specificity is desired an additional selective base can be added to the oligonucleotide, for instance but not limited to one additional selective base for each inosine or other non-selective base.

The antisense oligonucleotide preferably comprises at least 12 contiguous nucleobases of the nucleotide sequence (see FIG. 9):

| SEQ ID | Virus | Target | Sequence |
|---|---|---|---|
| 1 | BKPyV | Donor | 5' ACCUCUGAGCUACUCCAGGU 3' |
| 2 | BKPyV | Donor | 5' ACAAACCUCUGAGCUACUCC 3' |
| 3 | BKPyV | Donor | 5' CAGCACAAACCUCUGAGCUA 3' |
| 4 | BKPyV | Acceptor | 5' UCCAUAGGUUGGCACCUAGA 3' |
| 5 | BKPyV | Acceptor | 5' UGUUCCAUAGGUUGGCACCU 3' |
| 6 | JCPyV | Donor | 5' ACCUCUGAACUAUUCCAUGU 3' |
| 7 | JCPyV | Donor | 5' ACCAACCUCUGAACUAUUCC 3' |
| 8 | JCPyV | Donor | 5' CACAACCAACCUCUGAACUA 3' |
| 9 | JCPyV | Acceptor | 5' UCCAUAGGUUGGCACCUAAA 3' |
| 10 | JCPyV | Acceptor | 5' UGUUCCAUAGGUUGGCACCU 3' |
| 11 | KIPyV | Donor | 5' GUAUACCUGAGAAGAUUGCC 3' |
| 12 | KIPyV | Donor | 5' UCUUUGCAGUAUACCUGAGA 3' |
| 13 | KIPyV | Acceptor | 5' UGUACCGUAUGUAGGUAUCU 3' |
| 14 | KIPyV | Acceptor | 5' CCGUAUGUAGGUAUCUAUAC 3' |
| 15 | WUPyV | Donor | 5' UCUACCUGUGAAGAGCUCCA 3' |
| 16 | WUPyV | Donor | 5' UGUGCAUUCUACCUGUGAAG 3' |
| 17 | MCPyV | Donor | 5' CCUCAUCAAACAUAGAGAAG 3' |
| 18 | MCPyV | Donor | 5' GGAAAUUUGUACUGACCUC 3' |
| 19 | Control | — | 5' AGGUCCACACUCAAUCCUCA 3' |
| 20 | HYB_06 | Donor | 5' AAACCUCUGAGCUACUCCAG 3' |
| 21 | HYB_07 | Donor | 5' GCACAAACCUCUGAGCUACU 3' |
| 22 | HYB_08 | Donor | 5' AUCAGCACAAACCUCUGAGC 3' |
| 23 | HYB_09 | Donor | 5' AAAUCAGCACAAACCUCUGA 3' |
| 24 | HYB_10 | Donor | 5' GAAAAUCAGCACAAACCUCU 3' |
| 25 | HYB_11 | Donor | 5' AGGAAAAUCAGCACAAACCU 3' |
| 26 | HYB_12 | Acceptor | 5' CAUAGGUUGGCACCUAUAAA 3' |
| 27 | HYB_13 | Acceptor | 5' UUCCAUAGGUUGGCACCUAU 3' |
| 28 | HYB_14 | Coding Exon 1 | 5' UGAGCUCCAUGGAUUCUUCC 3' |
| 29 | SAN-73 | Coding Exon 2 | 5' CACTCTTCTGTTCCAT 3' |
| 30 | SAN-74 | Donor | 5' CACAAACCTCTGAGCT 3' |

In one embodiment, the antisense oligonucleotide as described herein comprises at least one backbone modification. In one embodiment antisense oligonucleotide comprises a phosphorothioate modification. The phosphorothioate (PS) modification substitutes a sulfur atom for a non-bridging oxygen in the phosphate backbone of an oligo. This modification renders the internucleotide linkage resistant to nuclease degradation. Phosphorothioate bonds can be introduced between the last 3 to 5 nucleotides at the 5'- or 3'-end of the oligo to inhibit exonuclease degradation (see FIG. 7). Including phosphorothioate bonds throughout the entire oligo will help reduce attack by endonucleases as well (see FIG. 3).

In another embodiment the antisense oligonucleotide comprises a morpholino (phosphorodiamidate morpholino) modification. While morpholinos have standard nucleic acid bases, those bases are bound to morpholine rings linked to each other by phosphorodiamidate groups instead of phosphates. Morpholinos do not trigger the degradation of their target RNA molecules.

In one embodiment, the antisense oligonucleotide comprises at least one sugar modification on the 2' carbon of the ribose moiety of the nucleoside. In one embodiment, the antisense oligonucleotide comprises at least one 2' sugar modification. An overview of sugar modifications for antisense purposes is given in Prakash (2011; Chem. Biodivers. September 8(9): 1616-1641. Doi 10.1002/cbdv.201100081). As shown in FIG. 7, preferred 2' sugar modifications are 2'-alkoxy or 2'-alkoxyalkoxy modifications, more preferably 2'-methoxyethoxy. Preferred modifications are 2'-O-methyl (2'-O-Me), 2'-O-methoxyethyl (2'-MOE), 2'-S-constrained-ethyl (2'-cEt) and locked nucleic acid (LNA).

Other modifications include peptide nucleic acid (PNA).

In some embodiments all positions in a given antisense oligonucleotide are uniformly modified. In other embodiments some positions in a given antisense oligonucleotide are not uniformly modified. In fact, more than one of the aforementioned modifications may be incorporated in a single antisense oligonucleotide or even in a single nucleoside within an antisense oligonucleotide. The present invention also includes antisense oligonucleotides which are chimeric antisense oligonucleotide. Chimeric antisense oligonucleotides are antisense oligonucleotides which contain two or more chemically distinct regions, each made up of at least one nucleotide. These antisense oligonucleotides contain at least one region wherein the antisense oligonucleotide is modified so as to confer upon the antisense oligonucleotide increased resistance to nuclease degradation, increased cellular uptake, and/or increased binding affinity for the target nucleic acid.

An antisense oligonucleotide may serve as a substrate for enzymes capable of cleaving RNA:DNA or RNA:RNA hybrids. Often such a possibility is mediated by the inclusion of a region in the interior of the antisense oligonucleotide. Such antisense oligonucleotides are also referred to as "gapmers". A gapmer is a chimeric antisense oligonucleotide that contains a typically central block of deoxyribonucleotides monomers sufficiently long to induce RNaseH cleavage. Efficient RNase cleavage requires a stretch of 4 or more deoxyribonucleotides. Typically such stretches have 9 or more deoxyribonucleotides. In the present invention it is preferred that the antisense oligonucleotide does not contain a region that can serve as a substrate for enzymes capable of cleaving RNA:DNA or RNA:RNA hybrids.

The antisense oligonucleotide preferably comprises modified nucleotides such as phosphorothioate-modified nucleobases and/or 2' sugar modifications thereby providing resistance to inadvertent degradation by nucleases. As shown in FIG. 7, preferred 2' sugar modification are 2'-alkoxy or 2'-alkoxyalkoxy modifications, more preferably 2'-methoxyethoxy. Preferred 2' sugar modifications include 2'-O-methyl (2'-O-Me), 2'-O-methoxyethyl (2'-MOE), 2'-S-constrained-ethyl (2'-cEt) and locked nucleic acid (LNA). The backbone may contain phosphorothioate throughout. Other configurations of antisense oligonucleotide are also comprehended by this invention. The antisense oligonucleotide preferably comprises modified nucleotides providing resistance to inadvertent degradation by nucleases of the target RNA, such as phosphorothioate modified nucleobases and/or 2' sugar modifications. Such an antisense oligonucleotide is within the scope of the invention. An oligonucleotide as disclosed herein thus preferably has a region that provides nuclease resistant to the target RNA. The duplex formed by the antisense oligonucleotide and the target RNA is not sensitive to the action of RNase H.

In a preferred embodiment the antisense oligonucleotide comprises a one or more nucleobases with a modified polymer backbone. The modified polymer backbone is preferably a modified backbone is indicated elsewhere herein. In a preferred embodiment the modified polymer backbone comprises a 2'-O-methyl (2'-O-Me), 2'-O-methoxyethyl (2'-MOE), 2'-S-constrained-ethyl (2'-cEt), locked nucleic acid (LNA), peptide nucleic acid (PNA) or morpholino (PMO) nucleotide. In a preferred embodiment all of the nucleotides in the modified polymer backbone comprises a modified sugar moiety, preferably at the 2' carbon. In a preferred embodiment the phosphate group linking two nucleotides is modified into a phosphorothioate group. Preferably all of the phosphodiester linkages are phosphorothioate linkages in the modified polymer backbone.

The human polyomaviruses can be divided into several genera, referred to as the alpha, the beta and the delta genus (Helle, F. et. al., Viruses, 2017). In a preferred embodiment the polyomavirus is an alpha or a beta virus, preferably a beta virus. Several human polyomaviruses are listed in the table herein below. In a preferred embodiment the polyomavirus is a BK polyomavirus (or BK virus, also referred to in this application as BKPyV or BKV), a JC polyomavirus (or JC virus, also referred to in this application as JCV) or a Merkel cell polyomavirus (MC polyomavirus, MC virus, or also referred to in this application as MCV). In a particularly preferred embodiment the polyomavirus is BK virus or JC virus, preferably BK virus.

| Abbreviation | Accession | 3' splice site target region | 5' splice site target region |
|---|---|---|---|
| BKPyV | NC_001538 | 4537-4596 | 4881-4940 |
| JCPyV | NC_001699 | 4397-4456 | 4741-4800 |
| KIPyV | NC_009238 | 4299-4358 | 4686-4745 |
| WUPyV | NC_009539 | 4477-4536 | 4876-4935 |
| MCPyV | NC_010277 | 4693-4752 | 5124-5183 |
| HPyV6 | NC_014406 | 4264-4323 | 4654-4713 |
| HPyV7 | NC_014407 | 4272-4331 | 4677-4736 |
| TSPyV | NC_014361 | 4352-4411 | 4765-4824 |
| HPyV9 | NC_015150 | 4408-4467 | 4760-4819 |
| MWPyV | NC_018102 | 4303-4362 | 4658-4717 |
| STLPyV | NC_020106 | 4159-4218 | 4504-4563 |
| HPyV12 | NC_020890 | 4392-4451 | 4791-4850 |
| NJPyV | NC_024118 | 4471-4530 | 4859-4918 |

The invention also provides a method of inhibiting polyomavirus replication in a cell, the method comprising providing a cell that is infected with said polyomavirus with the antisense oligonucleotide as described herein. The antisense oligonucleotide is preferably an oligonucleotide that targets the polyomavirus of the infection (see FIG. 3). The cell is preferably a cell that is susceptible for replication of the polyomavirus. When the cell is a cell in an animal such as a human, it is preferred that the animal is a permissive host, i.e. a host that allows a virus to circumvent its defenses and replicate the virus. For polyomaviruses, such as BK virus and JC virus, replication is often detected first by detecting viruses in the urine of the animal (uremia). Later, when the infection persists, virus can also be detected in the serum of the animal (viremia). Most humans encounter BK and JC virus during childhood, causing mild illness. However, when reactivated or acquired in the immunocompromised host, BK and JC virus have been implicated in a number of human clinical disease states. BK is most commonly associated with renal involvement, such as ureteral stenosis, hemorrhagic cystitis and nephropathy (Leploeg, M. D. et. al., Clinical Infectious Diseases, 2001; Helle, F. et. al., Viruses, 2017). Susceptibility or permissiveness of the host can be induced by compromising the hosts immune system. Various circumstances can lead to a temporary or permanent reduction of the hosts immune capability. Immunodeficiency (or immune deficiency) is a state in which the immune system's ability to fight infectious disease and cancer is compromised or entirely absent. Most cases of immunodeficiency are acquired ("secondary") due to extrinsic factors that affect the patient's immune system. Examples of these extrinsic factors include HIV infection, extremes of age, and environmental factors, such as nutrition. Immunosuppression can also be induced by some drugs, such as glucocorticoids, cytostatics, antibodies, and compounds that act upon immunophilins (such as calcineurin inhibitors, belatacept (an immunoglobulin like molecule that has the extracellular domain of CTLA-4) and similar molecules). This can be a desired effect such as in organ transplant surgery as an anti-rejection measure and in patients suffering from an overactive immune system, as in autoimmune diseases. However, sometimes this desired effect has the additional effect of reducing the individuals ability to combat virus infections, such as polyomavirus infection. A person who has an immunodeficiency of any kind is said to be immunocompromised. An immunocompromised person may be particularly vulnerable to opportunistic infections, in addition to normal infections that could affect everyone.

In one embodiment the invention provides a method of preparing a graft for transplantation, the method characterized in that donor cells, preferably donor kidney cells are provided with the antisense oligonucleotide as described herein. The antisense oligonucleotide is preferably an oligonucleotide that targets a polyomavirus that replicates in the graft cells. In the case of a kidney graft or kidney cell graft the polyomavirus is preferably a BK virus, a JC virus, or a MC virus-specific oligonucleotide. The cells of the graft thus treated are less susceptible to replication of the polyomavirus that the antisense oligonucleotide is specific for. This increases the success rate of the transplant. It facilitates the management of transplant recipients. One of the ways to manage opportunistic polyomavirus replication in transplant recipients and other drug-induced immune suppression in patients is to reduce the administration of the immunosuppressive drug, thereby allowing the immune system to recover to the extent that the infection and or replication of the virus is reduced. When a graft is prepared as described herein, the polyomavirus infections/replication in a patient is less frequent and, when detected, often less severe when compared to patients receiving untreated grafts. It is preferred that graft recipients receive one or more additional administrations with the antisense oligonucleotide as desired. The invention also provides a method of treatment of a polyomavirus infection in a subject, the method comprising administering the antisense oligonucleotide as described herein, to the individual in need thereof. The individual is preferably an immune-compromised individual.

The graft is preferably an allograft or a xenograft. Recipients of such grafts are often treated with immunosuppressive drugs to increase the survival of the graft, or to decrease the incidence and/or the severity of host versus graft effects. Many tissues can presently be grafted. Host versus graft effects are often a high risk when transplanting cells or organs from another, non-genetically identical human or a non-human animal. Grafts include lung, heart, heart valve, kidney, liver, pancreas, intestine, thymus and bone marrow. Polyomaviruses have been detected in the plasma of up to 3% of these patients receiving immunosuppression following organ transplantation (De Vlaminck, I. et. al., Cell, 2013). The graft preferably comprises a kidney, or kidney cells. The individual is preferably the recipient of a kidney or kidney cell transplant.

The antisense oligonucleotide is preferably one that confers resistance to RNase H to a duplex of the oligonucleotide and the target RNA. The antisense oligonucleotide preferably comprises a sequence that is the reverse complement of a contiguous stretch of at least 12 and preferably at least 17 nucleobases of an RNA that can be present in human kidney cells, preferably an RNA of a human virus that can replicate in human kidney cells, preferably a polyomavirus.

In one embodiment the invention provides an antisense oligonucleotide 12 to 30, preferably 17, 18, 19 or 20 to 30 nucleobases in length which comprises a sequence that is the reverse complement of a contiguous stretch of at least 12 nucleobases of a polyomavirus T-antigen pre-mRNA and which antisense oligonucleotide can modulate splicing of said T-antigen pre-mRNA in a cell, wherein the antisense oligonucleotide comprises at least 12 contiguous nucleobases of SEQ ID NO: 1; SEQ ID NO: 2; SEQ ID NO: 3; SEQ ID NO: 4; SEQ ID NO: 5; SEQ ID NO: 6; SEQ ID NO: 7; SEQ ID NO: 8; SEQ ID NO: 9; SEQ ID NO: 10; SEQ ID NO: 11; SEQ ID NO: 12; SEQ ID NO: 13; SEQ ID NO: 14; SEQ ID NO: 15; SEQ ID NO: 16; SEQ ID NO: 17; SEQ ID NO: 18; SEQ ID NO: 20; SEQ ID NO: 21; SEQ ID NO: 22; SEQ ID NO: 23; SEQ ID NO: 24; SEQ ID NO: 25; SEQ ID NO: 26 or SEQ ID NO: 27.

Further provided is an antisense oligonucleotide comprising at least 12 contiguous nucleobases of SEQ ID NO: 1; SEQ ID NO: 2; SEQ ID NO: 3; SEQ ID NO: 4; SEQ ID NO: 5; SEQ ID NO: 6; SEQ ID NO: 7; SEQ ID NO: 8; SEQ ID NO: 9; SEQ ID NO: 10; SEQ ID NO: 11; SEQ ID NO: 12; SEQ ID NO: 13; SEQ ID NO: 14; SEQ ID NO: 15; SEQ ID NO: 16; SEQ ID NO: 17; SEQ ID NO: 18; SEQ ID NO: 20; SEQ ID NO: 21; SEQ ID NO: 22; SEQ ID NO: 23; SEQ ID NO: 24; SEQ ID NO: 25; SEQ ID NO: 26 or SEQ ID NO: 27, wherein the at least twelve nucleotides comprise the reverse complement of the splice donor sequence or the splice acceptor sequence of the large T-antigen pre-mRNA of the respective polyomavirus.

The antisense oligonucleotide as described herein preferably comprises a modification that renders the mRNA-oligonucleotide duplex resistant to the action of RNase H. Preferably comprising at least one nucleobase with a modified polymer backbone, preferably a 2'-O-methyl (2'-O-Me), 2'-O-methoxyethyl (2'-MOE), 2'-S-constrained-ethyl (2'-cEt), locked nucleic acid (LNA), peptide nucleic acid (PNA) or morpholino (PMO) nucleotide. Preferably all of the nucleobases comprise a modified polymer backbone, preferably a 2'-O-methyl (2'-O-Me), 2'-O-methoxyethyl (2'-MOE), 2'-S-constrained-ethyl (2'-cEt), locked nucleic acid (LNA), peptide nucleic acid (PNA) or morpholino (PMO) nucleotide.

In a preferred embodiment the antisense oligonucleotide comprises at least 17, preferably at least 18, 19 and preferably at least 20 contiguous nucleobases of SEQ ID NO: 1; SEQ ID NO: 2; SEQ ID NO: 3; SEQ ID NO: 4; SEQ ID NO: 5; SEQ ID NO: 6; SEQ ID NO: 7; SEQ ID NO: 8; SEQ ID NO: 9; SEQ ID NO: 10; SEQ ID NO: 11; SEQ ID NO: 12; SEQ ID NO: 13; SEQ ID NO: 14; SEQ ID NO: 15; SEQ ID NO: 16; SEQ ID NO: 17; SEQ ID NO: 18; SEQ ID NO: 20; SEQ ID NO: 21; SEQ ID NO: 22; SEQ ID NO: 23; SEQ ID NO: 24; SEQ ID NO: 25; SEQ ID NO: 26 or SEQ ID NO: 27 or comprising at least 17, preferably at least 18, 19 and preferably at least 20 contiguous nucleobases of SEQ ID NO: 1; SEQ ID NO: 2; SEQ ID NO: 3; SEQ ID NO: 4; SEQ ID NO: 5; SEQ ID NO: 6; SEQ ID NO: 7; SEQ ID NO: 8; SEQ ID NO: 9; SEQ ID NO: 10; SEQ ID NO: 11; SEQ ID NO: 12; SEQ ID NO: 13; SEQ ID NO: 14; SEQ ID NO: 15; SEQ ID NO: 16; SEQ ID NO: 17; SEQ ID NO: 18; SEQ ID NO: 20; SEQ ID NO: 21; SEQ ID NO: 22; SEQ ID NO: 23; SEQ ID NO: 24; SEQ ID NO: 25; SEQ ID NO: 26 or SEQ ID NO: 27 with one mismatch and wherein the mismatch is not the first or the last nucleotide of the contiguous stretch.

Also provided is a method of inhibiting polyomavirus replication in a cell, the method comprising providing a cell that is infected with said polyomavirus with the antisense oligonucleotide. Also provided is a method of preparing a graft for transplantation, the method characterized in that donor cells, preferably donor kidney cells are provided with the antisense oligonucleotide.

Further provided is a method of treatment of a polyomavirus infection in a subject, the method comprising administering the antisense oligonucleotide as described herein, to the individual in need thereof. Said individual is an immune-compromised individual. The individual is preferably the recipient of a kidney or kidney cell transplant.

Also provided is a method of administering an antisense oligonucleotide to an individual, for hybridization to a complementary RNA sequence in a kidney cell of said individual, the method characterized in that the antisense oligonucleotide is an oligonucleotide as described herein.

Further provided is an antisense oligonucleotide comprising a modification that renders a duplex of the antisense oligonucleotide and the target mRNA resistant to the action of RNase wherein the antisense oligonucleotide comprises the sequence of SEQ ID NO: 1; SEQ ID NO: 2; SEQ ID NO: 3; SEQ ID NO: 4; SEQ ID NO: 5; SEQ ID NO: 6; SEQ ID NO: 7; SEQ ID NO: 8; SEQ ID NO: 9; SEQ ID NO: 10; SEQ ID NO: 11; SEQ ID NO: 12; SEQ ID NO: 13; SEQ ID NO: 14; SEQ ID NO: 15; SEQ ID NO: 16; SEQ ID NO: 17; SEQ ID NO: 18; SEQ ID NO: 20; SEQ ID NO: 21; SEQ ID NO: 22; SEQ ID NO: 23; SEQ ID NO: 24; SEQ ID NO: 25; SEQ ID NO: 26 or SEQ ID NO: 27, with no, one or two mismatches.

It has been observed that oligonucleotides as described herein are efficiently delivered to and taken up by the relevant kidneys cells when administered to the animal. The method of administration is preferably IV administration. For polyomaviruses that can cross the blood-brain barrier into the central nervous system (CNS) such as JC-virus it is possible to administer an antisense oligonucleotide to the CNS. Various ways are known in the art. For antisense oligonucleotide mediated treatment of JC virus infection of the CNS intrathecal delivery is preferred. JC virus infection can also be combatted by IV delivery as the initial infection is thought to be often via the tonsils or gastro-intestinal tract whereupon it spreads to other organs such as but not limited to tubular epithelial cells in the kidneys where it may remain latent or continue to reproduce, shedding virus particles in the urine and the brain.

The antisense oligonucleotide preferably does not have a sequence that consists of the sequence

5'-CACAAACCTCTGAGCTA; (SEQ ID NO: 31)

5'-AACCUCUGAACUAUUCCAUGU; (SEQ ID NO: 32)

5'-ACCUCUGAACUAUUCCAUGUA; (SEQ ID NO: 33)

5'-TTCATCTGTTCCATAGGTTGGCACCTA; (SEQ ID NO: 34)
or

5'-TTCCATAGGTTGGCACCTAAAAAAAAA, (SEQ ID NO: 35)

or an alternative thereof where one or more thymidine's are uracil's and vice versa.

For the purpose of clarity and a concise description features are described herein as part of the same or separate embodiments, however, it will be appreciated that the scope of the invention may include embodiments having combinations of all or some of the features described.

BRIEF DESCRIPTION OF THE DRAWINGS

FIG. 2: Whole-gene sequences of TAg, including intron sequences, were aligned using clustalW ("msa" package in R) for 245 unique BK-polyomavirus isolates (downloaded from the publicly available NCBI database). From these records, only the isolates reporting a complete genome were used for the conservation of the splice sites in TAg. The Dunlop strain was used as a reference genome. A phylogenetic tree was constructed using the UPGMA method ("phangorn" and "ggtree" packages in R). A sequence logo was constructed for the acceptor and donor splice sites to show nucleotide specific conservation between subtypes ("msa" package in R).

FIG. 3: Composition of antisense oligonucleotides to modulate BKPyV TAg splicing. Sequences of antisense oligonucleotides (AONs) directed towards the exon 1—intron junction (AONs #1, #2 and #3) and intron—exon 2 junction (AONs #4 and #5) of BKPyV TAg.

FIG. 9: Design of AONs that could be employed to target other polyomaviruses. Alongside the aforementioned BK and JC virus TAg splice-modulating AONs, AONs have been designed based on the possibility that they could also target the human polyomavirus 3 (Karolinska Institute or KI), human polyomavirus 4 (Washington University or WU) and human polyomavirus 5 (Merkel Cell virus or MCV). For human polyomaviruses 3-5, 2 AONs have been designed targeting the exon 1—intron junction, and 2 for the intron—exon 2 junction, as opposed to 3 AONs at the exon 1—intron site.

FIG. 10: Schematic of BK viral genome and BKV-targeting AONs. Part 1: The BK virus genome encodes six primary proteins, namely small t and large T antigen (early genes), as well as agnoprotein and the major capsid proteins VP1, VP2 and VP3 (late genes). The viral genome also contains a non-coding region (NCCR) whose sequence possesses both an origin of replication, as well as the promoter region that is responsible for recruiting transcription factors that drive expression early and late gene expression, while also co-ordinating viral genome replication. As shown in FIG. 1, alternative splicing of early and late pre-mRNAs results in numerous protein isoforms, including small t antigen, truncated T antigen (2 introns) and large T antigen (1 intron), along with alternative splicing determining the proportion of VP1, VP2 or VP3 that is generated. The primary splice variant generated for the late region predominantly results in expression of VP1. Part 2: AON sequences used to target the exon-intron junction of BKV large T antigen (TAg) as depicted in top panel. Part 3: Schematic depicting binding sites for AONs at the exon—intron junction of BKV TAg.

FIG. 37: Schematic of JC viral genome and JCV-targeting AONs. Part 1: Similar to BK virus, the JC virus genome encodes small t and large T antigen (early genes), as well as agnoprotein and the major capsid proteins VP1, VP2 and VP3 (late genes). The viral genome also contains a non-coding region (NCCR) with an origin of replication and promoter region for transcription factor binding that drives expression of the early and late genes, and viral genome replication. In contrast to extensive knowledge regarding BKV splicing of early and late region pre-mRNAs, less is known regarding JCV splicing. Part 2: AON sequences used to target the exon-intron junction of JCV large T antigen (TAg) as depicted in top panel. Part 3: Schematic depicting binding sites for AONs at the exon—intron junction of JCV TAg.

EXAMPLES

Example 1

Figure 1:
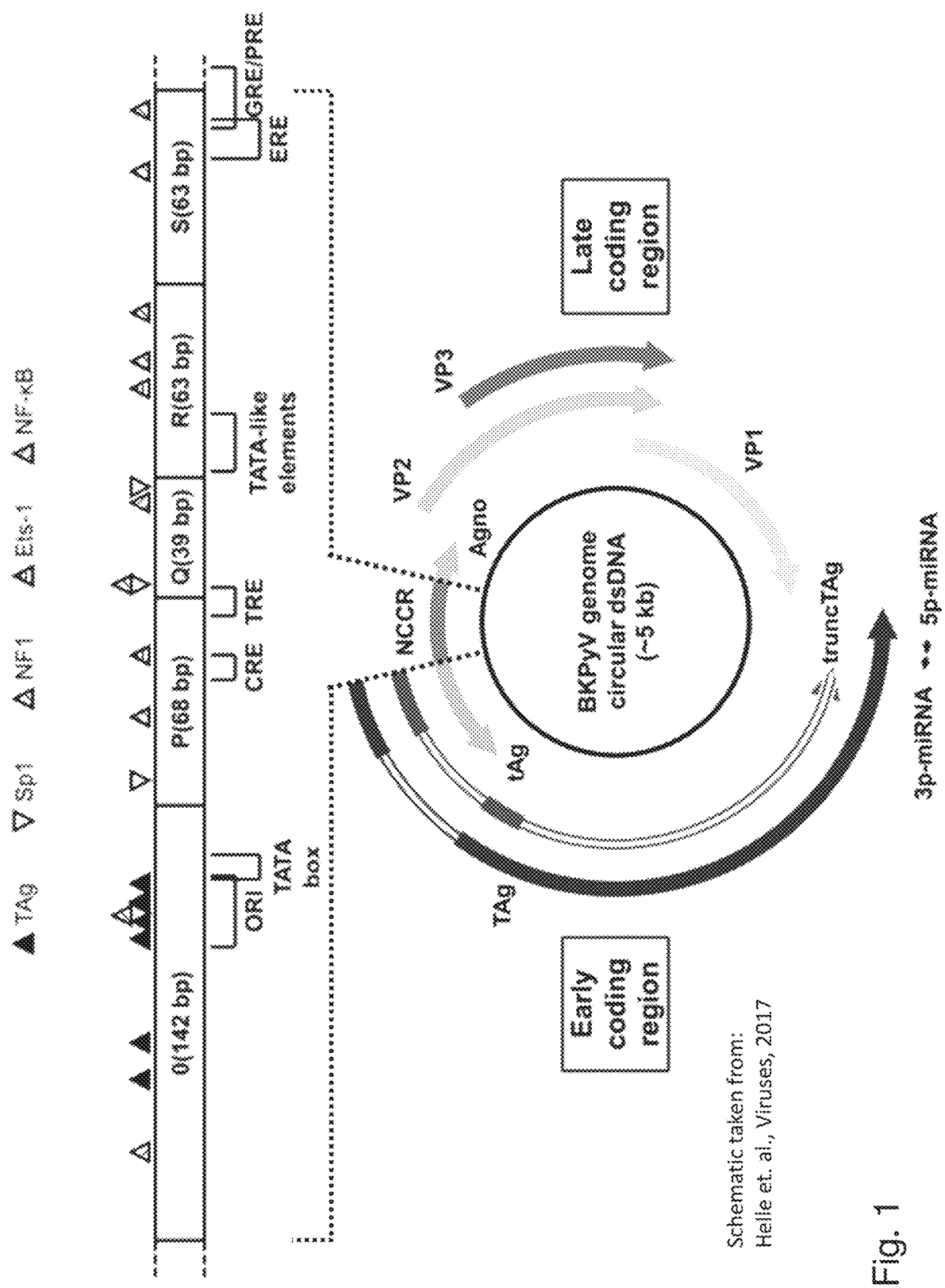
FIG. 1: Schematic of BK viral genome and sequence similarity of various BK virus genome subtypes. Left: The BK virus genome encodes five primary proteins, namely small t and large T antigen (early genes), as well as agnoprotein and the major capsid proteins VP1, VP2 and VP3 (late genes). The viral genome also contains a non-coding region (NCCR) which contains both the origin of replication, as well as the promoter region for transcription factors that drive the expression of the early and late genes, along with viral genome replication. Of note, alternative splicing of early and late pre-mRNAs results in numerous protein isoforms, including small t antigen, truncated T antigen (2 introns) and large T antigen (1 intron), along with alternative splicing determining the proportion of VP1, VP2 or VP3 that is generated. However, it is important to note that the primary splice variant generated for the late region is the mature mRNA that encodes predominantly VP1. Continued: The genomic sequence of the early region encodes the T antigen proteins, namely small t (tAg), truncated T (truncTAg) and large T antigen (TAg). tAg plays a critical role in driving infected cells into S phase, allowing for TAg-mediated viral genome replication. Furthermore, TAg binds to the NCCR to drive expression of the late region pre-mRNA. This leads to the production of VP1, VP2 and VP3, which are essential for encapsulation of the viral DNA.

Material and Methods
Accessions Used for Phylogenetic Analysis
Complete genomic sequences of BK polyomavirus isolates were downloaded from the publicly available NCBI database. From these records, only the isolates reporting a complete genome were used for the conservation of the splice sites in TAg. The Dunlop strain was used as a reference genome. Isolates "MM" and "FNL-9" were removed due to a large deletion in the intron or duplication overlapping the acceptor splice site respectively. Accession numbers of the 245 unique genomic sequences are provided below:

AB211369.1; AB211370.1; AB211371.1; AB211372.1; AB211373.1; AB211374.1; AB211375.1; AB211376.1; AB211377.1; AB211378.1; AB211379.1; AB211381.1; AB211382.1; AB211383.1; AB211384.1; AB211385.1; AB211386.1; AB211387.1; AB211388.1; AB211389.1; AB211390.1; AB211391.1; AB213487.1; AB217917.1; AB217918.1; AB217919.1; AB217920.1; AB217921.1; AB260028.1; AB260029.1; AB260030.1; AB260031.1; AB260032.1; AB260033.1; AB263912.1; AB263913.1; AB263914.1; AB263915.1; AB263916.1; AB263917.1; AB263918.1; AB263919.1; AB263920.1; AB263921.1; AB263922.1; AB263923.1; AB263924.1; AB263925.1; AB263926.1; AB263927.1; AB263928.1; AB263929.1; AB263930.1; AB263931.1; AB263932.1; AB263934.1; AB263935.1; AB263936.1; AB263938.1; AB269825.1; AB269826.1; AB269827.1; AB269828.1; AB269829.1; AB269830.1; AB269831.1; AB269832.1; AB269834.1;

AB269836.1; AB269837.1; AB269838.1; AB269840.1; AB269841.1; AB269842.1; AB269843.1; AB269844.1; AB269845.1; AB269846.1; AB269847.1; AB269848.1; AB269849.1; AB269850.1; AB269851.1; AB269852.1; AB269853.1; AB269854.1; AB269855.1; AB269856.1; AB269857.1; AB269858.1; AB269859.1; AB269860.1; AB269861.1; AB269862.1; AB269863.1; AB269864.1; AB269865.1; AB269866.1; AB269867.1; AB269868.1; AB269869.1; AB298941.1; AB298942.1; AB298945.1; AB298946.1; AB298947.1; AB301086.1; AB301087.1; AB301089.1; AB301090.1; AB301091.1; AB301092.1; AB301093.1; AB301094.1; AB301095.1; AB301096.1; AB301097.1; AB301099.1; AB301100.1; AB301101.1; AB365130.1; AB365132.1; AB365133.1; AB365134.1; AB365136.1; AB365137.1; AB365138.1; AB365139.1; AB365140.1; AB365141.1; AB365142.1; AB365144.1; AB365145.1; AB365146.1; AB365148.1; AB365149.1; AB365150.1; AB365151.1; AB365153.1; AB365154.1; AB365156.1; AB365157.1; AB365158.1; AB365159.1; AB365160.1; AB365162.1; AB365164.1; AB365165.1; AB365166.1; AB365167.1; AB365168.1; AB365170.1; AB365173.1; AB365174.1; AB365175.1; AB365176.1; AB365178.1; AB369087.1; AB369088.1; AB369089.1; AB369090.1; AB369092.1; AB369093.1; AB369094.1; AB369095.1; AB369096.1; AB369097.1; AB369098.1; AB369099.1; AB369101.1; AB464953.1; AB464954.1; AB464956.1; AB464957.1; AB464958.1; AB464960.1; AB464961.1; AB464962.1; AB485695.1; AB485696.1; AB485697.1; AB485698.1; AB485699.1; AB485700.1; AB485701.1; AB485703.1; AB485704.1; AB485707.1; AB485709.1; AB485710.1; AB485711.1; AB485712.1; AY628224.1; AY628225.1; AY628226.1; AY628227.1; AY628228.1; AY628229.1; AY628230.1; AY628231.1; AY628232.1; AY628233.1; AY628234.1; AY628235.1; AY628236.1; AY628237.1; AY628238.1; DQ305492.1; EF376992.1; FR720308.1; FR720309.1; FR720310.1; FR720311.1; FR720312.1; FR720313.1; FR720315.1; FR720317.1; FR720318.1; FR720320.1; FR720321.1; JF894228.1; JN192431.1; JN192432.1; JN192433.1; JN192435.1; JN192437.1; JN192438.1; JN192439.1; JN192440.1; JQ713822.1; KF055891.1; KF055892.1; KF055893.1; KP412983.1; KP984526.1; KY114802.1; KY114803.1; KY132094.1; KY487998.1; LC029413.1; LC309239.1; LC309240.1; LT960370.1; M23122.1; V01108.1.

Similarly, complete genomic sequences were downloaded for the 13 different prototype human polyomaviruses. The accession numbers are depicted below:

NC_001538; NC_001699; NC_009238; NC_009539; NC_010277; NC_014406; NC_014407; NC_014361; NC_015150; NC_018102; NC_020106; NC_020890; NC_024118.

Conservation of Large T Antigen Splice Sites

Whole genome nucleotide sequences from all reference human polyomaviruses were downloaded from the NCBI website (https://www.ncbi.nlm.nih.gov/nuccore) on Feb. 20, 2018 and aligned with WebPrank (available online: https://www.ebi.ac.uk/goldman-srv/webprank/) using default settings. A phylogenetic UPGMA tree was constructed and sequence logos for every splice site were created to show conservation between different human polyomaviruses. All downloaded refseq accession numbers are depicted below.

Reference sequences: NC_001538, NC_001699, NC_009238, NC_009539, NC_010277, NC_014406, NC_014407, NC_014361, NC_015150, NC_018102, NC_020106, NC_020890, NC_024118

Whole genome nucleotide sequences for all human polyomavirus isolates were downloaded from the NCBI website on Feb. 20, 2018. Whole gene sequences of Large T antigen were retrieved from only the unique genomic sequences and aligned with WebPrank using default settings Sequence logos were created for every splice site in Large T antigen to show conservation within and between different human polyomaviruses.

All downloaded accession numbers are depicted below:

BKPyV: AB211369.1, AB211370.1, AB211371.1, AB211372.1, AB211373.1, AB211374.1, AB211375.1, AB211376.1, AB211377.1, AB211378.1, AB211379.1, AB211380.1, AB211381.1, AB211382.1, AB211383.1, AB211384.1, AB211385.1, AB211386.1, AB211387.1, AB211388.1, AB211389.1, AB211390.1, AB211391.1, AB213487.1, AB217917.1, AB217918.1, AB217919.1, AB217920.1, AB217921.1, AB260028.1, AB260029.1, AB260030.1, AB260031.1, AB260032.1, AB260033.1, AB260034.1, AB263912.1, AB263913.1, AB263914.1, AB263915.1, AB263916.1, AB263917.1, AB263918.1, AB263919.1, AB263920.1, AB263921.1, AB263922.1, AB263923.1, AB263924.1, AB263925.1, AB263926.1, AB263927.1, AB263928.1, AB263929.1, AB263930.1, AB263931.1, AB263932.1, AB263933.1, AB263934.1, AB263935.1, AB263936.1, AB263937.1, AB263938.1, AB269822.1, AB269823.1, AB269824.1, AB269825.1, AB269826.1, AB269827.1, AB269828.1, AB269829.1, AB269830.1, AB269831.1, AB269832.1, AB269833.1, AB269834.1, AB269835.1, AB269836.1, AB269837.1, AB269838.1, AB269839.1, AB269840.1, AB269841.1, AB269842.1, AB269843.1, AB269844.1, AB269845.1, AB269846.1, AB269847.1, AB269848.1, AB269849.1, AB269850.1, AB269851.1, AB269852.1, AB269853.1, AB269854.1, AB269855.1, AB269856.1, AB269857.1, AB269858.1, AB269859.1, AB269860.1, AB269861.1, AB269862.1, AB269863.1, AB269864.1, AB269865.1, AB269866.1, AB269867.1, AB269868.1, AB269869.1, AB298940.1, AB298941.1, AB298942.1, AB298943.1, AB298944.1, AB298945.1, AB298946.1, AB298947.1, AB301086.1, AB301087.1, AB301088.1, AB301089.1, AB301090.1, AB301091.1, AB301092.1, AB301093.1, AB301094.1, AB301095.1, AB301096.1, AB301097.1, AB301098.1, AB301099.1, AB301100.1, AB301101.1, AB301102.1, AB301103.1, AB365130.1, AB365131.1, AB365132.1, AB365133.1, AB365134.1, AB365135.1, AB365136.1, AB365137.1, AB365138.1, AB365139.1, AB365140.1, AB365141.1, AB365142.1, AB365143.1, AB365144.1, AB365145.1, AB365146.1, AB365147.1, AB365148.1, AB365149.1, AB365150.1, AB365151.1, AB365152.1, AB365153.1, AB365154.1, AB365155.1, AB365156.1, AB365157.1, AB365158.1, AB365159.1, AB365160.1, AB365161.1, AB365162.1, AB365163.1, AB365164.1, AB365165.1, AB365166.1, AB365167.1, AB365168.1, AB365169.1, AB365170.1, AB365171.1, AB365172.1, AB365173.1, AB365174.1, AB365175.1, AB365176.1, AB365177.1, AB365178.1, AB369087.1, AB369088.1, AB369089.1, AB369090.1, AB369091.1, AB369092.1, AB369093.1, AB369094.1, AB369095.1, AB369096.1, AB369097.1, AB369098.1, AB369099.1, AB369100.1, AB369101.1, AB464953.1, AB464954.1, AB464955.1, AB464956.1, AB464957.1, AB464958.1, AB464959.1, AB464960.1, AB464961.1, AB464962.1, AB464963.1, AB485694.1, AB485695.1, AB485696.1, AB485697.1, AB485698.1, AB485699.1, AB485700.1, AB485701.1, AB485702.1, AB485703.1, AB485704.1, AB485705.1, AB485706.1, AB485707.1, AB485708.1, AB485709.1, AB485710.1, AB485711.1, AB485712.1,

AY628224.1, AY628225.1, AY628226.1, AY628227.1, AY628228.1, AY628229.1, AY628230.1, AY628231.1, AY628232.1, AY628233.1, AY628234.1, AY628235.1, AY628236.1, AY628237.1, AY628238.1, DQ305492.1, EF376992.1, FR720308.1, FR720309.1, FR720310.1, FR720311.1, FR720312.1, FR720313.1, FR720314.1, FR720315.1, FR720316.1, FR720317.1, FR720318.1, FR720319.1, FR720320.1, FR720321.1, FR720322.1, FR720323.1, JF894228.1, JN192431.1, JN192432.1, JN192433.1, JN192434.1, JN192435.1, JN192436.1, JN192437.1, JN192438.1, JN192439.1, JN192440.1, JN192441.1, JQ713822.1, KF055891.1, KF055892.1, KF055893.1, KP412983.1, KP984526.1, KY114802.1, KY114803.1, KY132094.1, KY487998.1, LC029411.1, LC029412.1, LC029413.1, LC029414.1, LC309239.1, LC309240.1, LT934539.1, LT960370.1, M23122.1, MF627830.1, MF627831.1, V01108.1, V01109.1

JCPyV: AB038249.1, AB038250.1, AB038251.1, AB038252.1, AB038253.1, AB038254.1, AB038255.1, AB048545.1, AB048546.1, AB048547.1, AB048548.1, AB048549.1, AB048550.1, AB048551.1, AB048552.1, AB048553.1, AB048554.1, AB048555.1, AB048556.1, AB048557.1, AB048558.1, AB048559.1, AB048560.1, AB048561.1, AB048562.1, AB048563.1, AB048564.1, AB048565.1, AB048566.1, AB048567.1, AB048568.1, AB048569.1, AB048570.1, AB048571.1, AB048572.1, AB048573.1, AB048574.1, AB048575.1, AB048576.1, AB048577.1, AB048578.1, AB048579.1, AB048580.1, AB048581.1, AB048582.1, AB074575.1, AB074576.1, AB074577.1, AB074578.1, AB074579.1, AB074580.1, AB074581.1, AB074582.1, AB074583.1, AB074584.1, AB074585.1, AB074586.1, AB074587.1, AB074588.1, AB074589.1, AB074590.1, AB074591.1, AB077855.1, AB077856.1, AB077857.1, AB077858.1, AB077859.1, AB077860.1, AB077861.1, AB077862.1, AB077863.1, AB077864.1, AB077865.1, AB077866.1, AB077867.1, AB077868.1, AB077869.1, AB077870.1, AB077871.1, AB077872.1, AB077873.1, AB077874.1, AB077875.1, AB077876.1, AB077877.1, AB077878.1, AB077879.1, AB081005.1, AB081006.1, AB081007.1, AB081008.1, AB081009.1, AB081010.1, AB081011.1, AB081012.1, AB081013.1, AB081014.1, AB081015.1, AB081016.1, AB081017.1, AB081018.1, AB081019.1, AB081020.1, AB081021.1, AB081022.1, AB081023.1, AB081024.1, AB081025.1, AB081026.1, AB081027.1, AB081028.1, AB081029.1, AB081030.1, AB081600.1, AB081601.1, AB081602.1, AB081603.1, AB081604.1, AB081605.1, AB081606.1, AB081607.1, AB081608.1, AB081609.1, AB081610.1, AB081611.1, AB081612.1, AB081613.1, AB081614.1, AB081615.1, AB081616.1, AB081617.1, AB081618.1, AB081654.1, AB092578.1, AB092579.1, AB092580.1, AB092581.1, AB092582.1, AB092583.1, AB092584.1, AB092585.1, AB092586.1, AB092587.1, AB103387.1, AB103402.1, AB103403.1, AB103404.1, AB103405.1, AB103406.1, AB103407.1, AB103408.1, AB103409.1, AB103410.1, AB103411.1, AB103412.1, AB103413.1, AB103414.1, AB103415.1, AB103416.1, AB103417.1, AB103418.1, AB103419.1, AB103420.1, AB103421.1, AB103422.1, AB103423.1, AB104487.1, AB113118.1, AB113119.1, AB113120.1, AB113121.1, AB113122.1, AB113123.1, AB113124.1, AB113125.1, AB113126.1, AB113127.1, AB113128.1, AB113129.1, AB113130.1, AB113131.1, AB113132.1, AB113133.1, AB113134.1, AB113135.1, AB113136.1, AB113137.1, AB113138.1, AB113139.1, AB113140.1, AB113141.1, AB113142.1, AB113143.1, AB113144.1, AB113145.1, AB113216.1, AB113217.1, AB118231.1, AB118232.1, AB118233.1, AB118234.1, AB118235.1, AB118651.1, AB118652.1, AB118653.1, AB118654.1, AB118655.1, AB118656.1, AB118657.1, AB118658.1, AB118659.1, AB126981.1, AB126982.1, AB126983.1, AB126984.1, AB126985.1, AB126986.1, AB126987.1, AB126988.1, AB126989.1, AB126990.1, AB126991.1, AB126992.1, AB126993.1, AB126994.1, AB126995.1, AB126996.1, AB126997.1, AB126998.1, AB126999.1, AB127000.1, AB127001.1, AB127002.1, AB127003.1, AB127004.1, AB127005.1, AB127006.1, AB127007.1, AB127008.1, AB127009.1, AB127010.1, AB127011.1, AB127012.1, AB127013.1, AB127014.1, AB127015.1, AB127016.1, AB127017.1, AB127018.1, AB127019.1, AB127020.1, AB127021.1, AB127022.1, AB127023.1, AB127024.1, AB127025.1, AB127026.1, AB127027.1, AB127342.1, AB127343.2, AB127344.1, AB127345.2, AB127346.1, AB127347.1, AB127348.1, AB127349.1, AB127350.2, AB127351.2, AB127352.1, AB127353.1, AB183152.1, AB195639.1, AB195640.1, AB198940.1, AB198941.1, AB198942.1, AB198943.1, AB198944.1, AB198945.1, AB198946.1, AB198947.1, AB198948.1, AB198949.1, AB198950.1, AB198951.1, AB198952.1, AB198953.1, AB198954.1, AB220939.1, AB220940.1, AB220941.1, AB220942.1, AB220943.1, AB262396.1, AB262397.1, AB262398.1, AB262399.1, AB262400.1, AB262401.1, AB262402.1, AB262403.1, AB262404.1, AB262405.1, AB262406.1, AB262407.1, AB262408.1, AB262409.1, AB262410.1, AB262411.1, AB262412.1, AB262413.1, AB362351.1, AB362352.1, AB362353.1, AB362354.1, AB362355.1, AB362356.1, AB362357.1, AB362358.1, AB362359.1, AB362360.1, AB362361.1, AB362362.1, AB362363.1, AB362364.1, AB362365.1, AB362366.1, AB372036.1, AB372037.1, AB372038.1, AF030085.1, AF295731.1, AF295732.1, AF300945.1, AF300946.1, AF300947.1, AF300948.1, AF300949.1, AF300950.1, AF300951.1, AF300952.1, AF300953.1, AF300954.1, AF300955.1, AF300956.1, AF300957.1, AF300958.1, AF300959.1, AF300960.1, AF300961.1, AF300962.1, AF300963.1, AF300964.1, AF300965.1, AF300966.1, AF300967.1, AF363830.1, AF363831.1, AF363832.1, AF363833.1, AF363834.1, AY121907.1, AY121908.1, AY121909.1, AY121910.1, AY121911.1, AY121912.1, AY121913.1, AY121914.1, AY121915.1, AY328376.1, AY342299.1, AY349147.1, AY356539.1, AY364314.1, AY366359.1, AY373463.1, AY376828.1, AY376829.1, AY376830.1, AY376831.1, AY378084.1, AY378085.1, AY378086.1, AY378087.1, AY382184.1, AY382185.1, AY382186.1, AY382187.1, AY382188.1, AY386373.1, AY386374.1, AY386375.1, AY386376.1, AY386377.1, AY386378.1, AY536239.1, AY536240.1, AY536241.1, AY536242.1, AY536243.1, DQ875211.1, DQ875212.1, EU835194.1, JF424834.1, JF424835.1, JF424836.1, JF424837.1, JF424838.1, JF424839.1, JF424840.1, JF424841.1, JF424842.1, JF424843.1, JF424844.1, JF424845.1, JF424846.1, JF424847.1, JF424848.1, JF424849.1, JF424850.1, JF424851.1, JF424852.1, JF424853.1, JF424854.1, JF424855.1, JF424856.1, JF424857.1, JF424858.1, JF424859.1, JF424860.1, JF424861.1, JF424862.1, JF424863.1, JF424864.1, JF424865.1, JF424866.1, JF424867.1, JF424868.1, JF424869.1, JF424870.1, JF424871.1, JF424872.1, JF424873.1, JF424874.1, JF424875.1, JF424876.1, JF424877.1, JF424878.1, JF424879.1, JF424880.1, JF424881.1, JF424882.1, JF424883.1, JF424884.1, JF424885.1, JF424886.1, JF424887.1, JF424888.1, JF424889.1, JF424890.1, JF424891.1, JF424892.1, JF424893.1, JF424894.1, JF424895.1, JF424896.1,

JF424897.1, JF424898.1, JF424899.1, JF424900.1, JF424901.1, JF424902.1, JF424903.1, JF424904.1, JF424905.1, JF424906.1, JF424907.1, JF424908.1, JF424909.1, JF424910.1, JF424911.1, JF424912.1, JF424913.1, JF424914.1, JF424915.1, JF424916.1, JF424917.1, JF424918.1, JF424919.1, JF424920.1, JF424921.1, JF424922.1, JF424923.1, JF424924.1, JF424925.1, JF424926.1, JF424927.1, JF424928.1, JF424929.1, JF424930.1, JF424931.1, JF424932.1, JF424933.1, JF424934.1, JF424935.1, JF424936.1, JF424937.1, JF424938.1, JF424939.1, JF424940.1, JF424941.1, JF424942.1, JF424943.1, JF424944.1, JF424945.1, JF424946.1, JF424947.1, JF424948.1, JF424949.1, JF424950.1, JF424951.1, JF424952.1, JF424953.1, JF424954.1, JF424955.1, JF424956.1, JF424957.1, JF424958.1, JF424959.1, JF424960.1, JF424961.1, JF424962.1, JF425488.1, JF425489.1, JF425490.1, JF425491.1, JF425492.1, JF425493.1, JF425494.1, JF425495.1, JF425496.1, JF425497.1, JF425498.1, JF425499.1, JF425500.1, JF425501.1, JF425502.1, JF425503.1, JF425504.1, JF425551.1, JF425552.1, JF425553.1, JF425554.1, JF425555.1, JF425556.1, JQ237146.1, JQ823124.1, JX273163.1, KJ659286.1, KJ659287.1, KJ659288.1, KJ659289.1, KM225765.1, LC164349.1, LC164350.1, LC164351.1, LC164352.1, LC164353.1, LC164354.1, MF662180.1, MF662181.1, MF662182.1, MF662183.1, MF662184.1, MF662185.1, MF662186.1, MF662187.1, MF662188.1, MF662189.1, MF662190.1, MF662191.1, MF662192.1, MF662193.1, MF662194.1, MF662195.1, MF662196.1, MF662197.1, MF662198.1, MF662199.1, MF662200.1, MF662201.1, MF662202.1, MF662203.1, MF662204.1

KIPyV: EF520287.1, EF520288.1, EF520289.1, EU358766.1, EU358767.1, KC571691.1, KM085447.1, KU746835.1

WUPyV: EF444549.1, EF444550.1, EF444551.1, EF444552.1, EF444553.1, EF444554.1, EU296475.1, EU358768.1, EU358769.1, EU711054.1, EU711055.1, EU711056.1, EU711057.1, EU711058.1, FJ794068.1, FJ890981.1, FJ890982.1, GQ926975.1, GQ926976.1, GQ926977.1, GQ926978.1, GQ926979.1, GQ926980.1, GU296361.1, GU296362.1, GU296363.1, GU296364.1, GU296365.1, GU296366.1, GU296367.1, GU296368.1, GU296369.1, GU296370.1, GU296371.1, GU296372.1, GU296373.1, GU296374.1, GU296375.1, GU296376.1, GU296377.1, GU296378.1, GU296379.1, GU296380.1, GU296381.1, GU296382.1, GU296383.1, GU296384.1, GU296385.1, GU296386.1, GU296387.1, GU296388.1, GU296389.1, GU296390.1, GU296391.1, GU296392.1, GU296393.1, GU296394.1, GU296395.1, GU296396.1, GU296397.1, GU296398.1, GU296399.1, GU296400.1, GU296401.1, GU296402.1, GU296403.1, GU296404.1, GU296405.1, GU296406.1, GU296407.1, GU296408.1, HQ218321.1, KC571693.1, KC571694.1, KC571695.1, KC571696.1, KC571697.1, KC571698.1, KC571699.1, KJ643309.1, KJ725028.1, KM265136.1, KU049032.1, KU672381.1, KX650181.1, KX650182.1, KX650184.1, KX650185.1, KX650186.1, KX650187.1, KX650188.1, KX650189.1, KX650190.1, KX650191.1, KX650192.1, KX650193.1

MCPyV: EU375803.1, EU375804.1, FJ173815.1, FJ464337.1, HM011538.1, HM011539.1, HM011540.1, HM011541.1, HM011542.1, HM011543.1, HM011544.1, HM011545.1, HM011546.1, HM011547.1, HM011548.1, HM011549.1, HM011550.1, HM011551.1, HM011552.1, HM011553.1, HM011554.1, HM011555.1, HM011556.1, HM011557.1, HM355825.1, JF812999.1, JF813000.1, JF813001.1, JF813002.1, JF813003.1, JN383838.1, JN383839.1, JN383840.1, JN383841.1, JQ479315.1, JQ479316.1, JQ479317.1, JQ479318.1, JQ479319.1, JQ479320.1, JX045708.1, JX045709.1, KC202810.1, KC571692.1, KF266963.1, KF266964.1, KF266965.1, KX781279.1, KX827417.1. NC_010277.2

HPyV6: HM011558.1, HM011559.1, HM011560.1, HM011561.1, HM011562.1, HM011563.1, KM387421.1, KM655817.1, KR090570.1, KU596573.1, KX379630.1, KX379631.1, KX771234.1

HPyV7: HM011564.1, HM011565.1, HM011566.1, HM011567.1, HM011568.1, HM011569.1, KJ733012.1, KJ733013.1, KX771235.1

TSPyV: AB873001.1, JQ723730.1, KF444091.1, KF444092.1, KF444093.1, KF444094.1, KF444095.1, KF444096.1, KF444097.1, KF444098.1, KF444099.1, KF444100.1, KF444101.1, KM007161.1, KM655816.1, KU221329.1, KX249740.1, KX249741.1, KX249742.1, KX249743.1

HPyV9: HQ696595.1, KC831440.1

MWPyV: JQ898291.1, JQ898292.1, KC549586.1, KC549587.1, KC549588.1, KC549589.1, KC549590.1, KC549591.1, KC549592.1, KC549593.1, KC549594.1, KC571700.1, KC571701.1, KC571702.1, KC571703.1, KC571704.1, KC571705.1, KC690147.1, KR338953.1

STLPyV: JX463183.1, JX463184.1, KF525270.1, KF530304.1, KF651951.1, KM893862.1, KR090571.1, NC_020106.1

HPyV12: JX308829.1, NC_020890.1

NJPyV: KF954417.1, NC_024118.1

Splice Site Conservation and Phylogenetic Trees

Whole-gene sequences of TAg, including intron sequences, were aligned using clustalW ("msa" package in R) for the 13 different polyomavirus reference sequences and all unique BK-polyomavirus isolates. A phylogenetic tree was constructed using the UPGMA method ("phangorn" and "ggtree" packages in R). A sequence logo was constructed for the acceptor and donor splice sites to show nucleotide specific conservation between subtypes ("msa" package in R).

AON Design

Antisense oligonucleotides (AONs) were designed to target the splice sites in TAg. Ribonucleic acids in the AONs contain 2'-OMe modifications. AONs are 20 nucleotides in length with a full phosphorothioate backbone (*). For in vitro studies the AONs contain a 5'-FAM label. Secondary structure and binding energy of the AONs were predicted using RNA structure. All AON sequences are depicted below:

| Name | Sequence | Target splice site in TAg | SEQ ID NO |
|---|---|---|---|
| Scrambled | G*C*A*C*C*U*C*U*G*C*G*U*C*C*U*A*G*A*A*T | Not applicable | 36 |
| 1_1 | A*C*U*C*U*G*A*G*C*U*A*C*U*C*C*A*G*G*U | Donor (exon 1) | 1 |
| 1_2 | A*C*A*A*A*C*C*U*C*U*G*A*G*C*U*A*C*U*C | Donor (exon 1) | 2 |

| Name | Sequence | Target splice site in TAg | SEQ ID NO |
|---|---|---|---|
| 1_3 | C*A*G*C*A*C*A*A*A*C*C*U*C*U*G*A*G*C*U*A | Donor (exon 1) | 3 |
| 2_1 | U*C*C*A*U*A*G*G*U*U*G*G*C*A*C*C*U*A*G*A | Acceptor (exon 2) | 4 |
| 2_2 | U*G*U*U*C*C*A*U*A*G*G*U*U*G*G*C*A*C*C*U | Acceptor (exon 2) | 5 |

*Indicates a phosphorothioate linkage.

Cell Culture

Immortalized proximal tubule kidney epithelial HK2 cells (ATCC® CRL-2190™) were obtained from ATCC and maintained at 37° C., 5% $CO_2$, in Dulbecco's Modified Eagle's medium-F12, 1:1 mixture with 15 mM Hepes, 2.5 mM L-glutamine (Lonza) and supplemented with Tri-iodo thyronine, epidermal growth factor (EGF), insulin-transferrin-selenium-ethanolamine (ITS-X), hydrocortison and 100 U/mL penicillin-streptomycin. BK polyomavirus (ATCC® VR-837™) was obtained from ATCC and diluted in complete HK2 culture media to reduce the infectious load. For treatment experiments, cells were seeded in 6-, or 12-wells plates (Corning) at a density of 32,000 cells/cm² and grown overnight. AON treatment was performed by incubating the cells for 5 h with lipofectamine 3000 (Thermo Fisher) at an AON concentration of 50 nM, after which the lipofectamine was washed off. Infections with BK polyomavirus were performed 24 h after washing of the cells by incubating the cells with BK polyomavirus-containing culture media for 2 h, after which the virus was washed off. Supernatant was collected after washing and at 3, 5 and 7 days after infection to determine the production of viral particles using PCR. A viral load sample was collected before infection to determine the infectious load. RNA and protein was harvested at day 7 to determine the expression of TAg and VP1.

Viral Load Determinations

In order to determine the viral load in the culture supernatant, 200 μL was collected from every well for every time point. Pierce Universal Nuclease was added to every sample to degrade unpackaged DNA for 15 minutes at RT and was then inactivated with 5 mM EDTA. Viral DNA was isolated from the supernatant using the DNA mini kit (Qiagen) and the viral load was determined using Taqman PCR as described below (Wunderink, H. F., et. al., *J. Clin. Virol.*, 2017).

To monitor the quality of DNA extraction and potential PCR inhibition, we added low concentrations of phocine herpesvirus to the lysis buffer. DNA was eluted in a final volume of 100 μL elution buffer, of which 10 μL was used as input for real-time quantitative PCR (qPCR). Using the primers 440BKVs 5'-GAAAAGGAGAGT-GTCCAGGG-3' (SEQ ID NO: 37) and 441BKVas 5'-GAACTTC-TACTCCTCCTT-TTATTAGT-3' (SEQ ID NO:38) and a Taqman probe 576BKV-TQ-FAM FAM 5'-CCAAAAAGC-CAAAGGAACCC-3'-BHQ1 (SEQ ID NO:39), a 90-bp fragment within the BKPyV VP1 gene was amplified. The BKPyV qPCR and phocine herpesvirus PCR were duplexed for DNA quality and potential PCR inhibition monitoring. Furthermore, the BKPyV qPCR was validated to detect BKPyV genotypes I-IV.

Quantitative PCR reactions were performed in a total volume of 50 μL, containing 25 μL HotStarTaq Master Mix (QIAGEN, Hilden, Germany), 0.5 μmol/L of each primer, 0.35 μmol/L BKPyV probe, and 3.5 mmol/L MgCl2. Reactions were performed using a CFX96 real-time detection system (Bio-Rad, Hercules, Calif., USA) with the following cycle conditions: 15 min at 95° C. followed by 45 cycles of amplification (30 s at 95° C.; 30 s at 55° C.; 30 s at 72° C.). For quantification, a standard of a quantified BKPyV-positive urine sample was used. Analytical sensitivity of the BKPyV qPCR was ~10 copies/mL. On each plate, 3 negative controls were included; these controls tested negative in all PCR assays. PCR results with a cycle threshold ≥40 were considered negative.

Antibodies and Western Blot

Protein concentrations were determined using the BCA method. Samples were run on a 4-15% TGX gel and transferred to a nitrocellulose or PVDF membrane. Antibodies used were: rabbit polyclonal anti-actin-HRP (loading control), rabbit polyclonal anti-SV40 VP1 (ab53977, Abcam), mouse monoclonal anti-SV40 T-antigen [PAb416] (ab16879, Abcam) and mouse monoclonal anti-SV40 T-Antigen (PAb108, Thermo Fisher). The primary antibody was incubated overnight at 4° C. for TAg and VP1 and 30 minutes at RT for actin. Secondary antibodies used for TAg and VP1 were goat polyclonal anti-mouse-HRP (P044701-2, Agilent) and goat polyclonal anti-rabbit-HRP (P044801-2, Agilent) respectively. The membranes were incubated with SuperSignal™ West Femto Maximum Sensitivity Substrate (Thermo Fisher) and protein bands were visualized using the ChemiDoc MP Imaging System (Bio Rad).

Real-Time qPCR

BK-infected HK2 cells were lysed in Trizol and RNA was isolated using the RNeasy kit (Qiagen). A DNAse I (Qiagen) treatment was added to remove excess DNA during the isolation and cDNA was synthesized using Promega reverse transcriptase, DTT, dNTPs and random primers. Real time PCR was performed on a CFX384 Touch™ Real-Time PCR Detection System (Bio Rad) with SYBR™ Select Master Mix (Thermo Fisher) and the following primers:

| Gene | Forward | SEQ ID NO | Reverse | SEQ ID NO |
|---|---|---|---|---|
| GAPDH | ACAACTTTGGTATCGTGGAAGG | 40 | GCCATCACGCCACAGTTTC | 41 |
| TAg | GAGGAGGATGTAAAGGTAGCTCA | 42 | ACTGGCAAACATATCTTCATGGC | 43 |
| VP1 | TGCAGGGTCACAAAAAGTGC | 44 | AGCACTCCCTGCATTTCCAA | 45 |

Results
Design of BK-Targeting Antisense Oligonucleotides

Efficient antisense oligonucleotides (AONs) that target the BKPyV large T antigen (TAg) must be specific for BKPyV in the sense that they are not specific for host RNA species, while preferably also being as universal to other different BKPyV isolates and different polyomaviruses in general as possible. dsDNA viruses (in this cases polyomaviruses) as compared to dsRNA/ssRNA viruses are characterized by less genetic drift. Nonetheless, there remain a large number of BKPyV genotypes and subgenotypes that give rise to a large number of BKPyV serotypes (see phylogenetic tree in FIG. 2). Since TAg contains two exons, we first identified the genomic sequence at the exon-intron junctions in attempts to identify AON candidates (See FIG. 2). To achieve this, we extracted the available unique BKPyV TAg genomic sequences (n=245 accession numbers provided in Material and Methods section) from the NCBI database and aligned these using ClustalW. Regions that depicted that a high level of sequence similarity (or conservation) were targeted. These studies revealed a high degree of conservation in exon 1 and flanking intronic sequence (see FIG. 2). Exon 2 also displayed a high level of sequence conservation. Flanking intronic sequence was both T nucleotide-rich and less conserved within 4 nucleotides from the exon boundary. AON were targeted to exon 1 of BKPyV TAg and bridge portions of intronic sequence at exon 1. For exon 2 AON were targeted to 4-6 nucleotides in the intronic region of exon 2 and the flanking exon 2 sequence.

As shown in FIG. 3, we elected to design 5 AONs targeting BKPyV TAg, 3 of which target the exon 1—intron portion (designated AON #1, #2 and #3), while 2 AONs target the exon 2—intron portion (termed AON #4 and #5). The AONs progressively shift from primarily exonic to including significant intron-binding sequence for exon 1 targeting AONs (AON 1-3). See Material and Methods section and FIG. 3 for exact sequences, as well as the backbone and sugar moiety modifications.

This design allowed us to specifically target the TAg of BKPyV, while also being universal for distinct BKPyV genotypes in kidney transplant patients.

AON-Mediated Reduction in BKPyV TAg RNA

We employed lipofectamine-based delivery of the AONs, which markedly improved AON uptake within 5 hours after transfection. Moreover, we titrated AON dosage based on FAM label cellular intensity to be maximal at approximately 50 nM. Twenty-four hours (24 h) after AON administration, HK2 cells were infected with BKV for 2 hours, after which the cells were washed and cultured for 3, 5 and 7 days. At these points, RNA was harvested from the cells and qRT-PCR performed to determine which AONs could affect TAg expression levels. HK2 cells that were not transfected with AONs (untreated) displayed similar expression levels of TAg as compared to scrambled-AON (Scr) treated cells (data not shown).

It is well established that a considerable proportion of AONs designed to modulate expression levels or splicing of a given target RNA are efficacious. Our studies using the AONs #2, #3, or #4 repeatedly displayed significant reductions in TAg RNA levels, generally revealing 5- to 10-fold attenuation in the RNA levels of this viral DNA driver (see FIG. 4, left panel).

BKPyV-infected cultures that were treated with the AONs #2, #3, #4 or #5 repeated exhibited diminished TAg RNA expression levels. This establishes the sites targeted by these AON as good target sites for reducing BK virus production by reducing TAg production. Of note, this reduction is observed in the setting a high MOI, namely in the range of 100.

AON-Mediated Reduction of VP1 RNA and Protein

In cells latently infected by polyomavirus, such as BKV-infected proximal tubule cells of the kidney, low levels of TAg RNA and protein expression are maintained. In individuals with a compromised immune system, be it natural or induced by an immunosuppressive regimen, replication of virus and induction of TAg expression is observed (Hasegawa, M. et. al., Transplantation Proceedings, 2014; Nickeleit, V. et. al., JASN, 2018). Augmentation of TAg levels, along with the interaction with accessory transcription factors to the non-coding/promoter region of the BKV genome drives both BK genome replication and expression of the (late region) major capsid proteins. Collectively, the TAg-mediated activation of viral DNA replication and encapsulation by the capsid proteins results in the generation of infectious viral particles that can be detected in both the urine (viruria) and in the serum (viremia)(Helle, F. et. al., Viruses, 2017).

Figure 5:
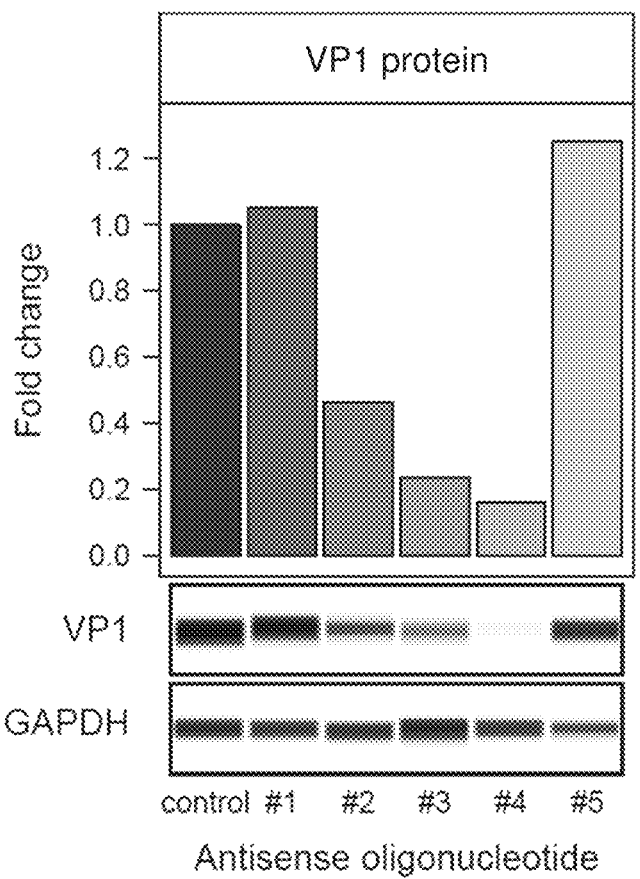
FIG. 5: TAg splice-modulating AONs reduce expression levels of VP1 protein in BKPyV infected human epithelial cells. Western blot analysis of HK2 cellular lysates harvested 7 days post-infection with BK polyomavirus at a multiplicity of infection of ~100. As compared to scramble AON-treated HK2 cells, AON #2, #3 and #4 clearly abrogate expression levels of VP1 protein (n=4).

To test whether AONs are effective in reducing BKV generation we determined the expression profile of TAg-activated proteins, including VP1. VP1 is the major structural constituent of the icosahedral viral capsid. This outer shell has 72 pentamers that are joined in a stoichiometry of 5:1 by either VP2 or VP3. As such, we performed qRT-PCR for VP1, which revealed that expression levels of VP1 are much higher than TAg per copies of GAPDH (data not shown). This is in keeping with the fact that TAg, along with other transcription factors, induces expression of VP1 mRNA. Furthermore, in all studies, our AONs #2, #3, #4 and #5 reduced VP1 RNA expression levels, along with striking reductions in VP1 protein (see FIG. 5, right panel).

Figure 4:
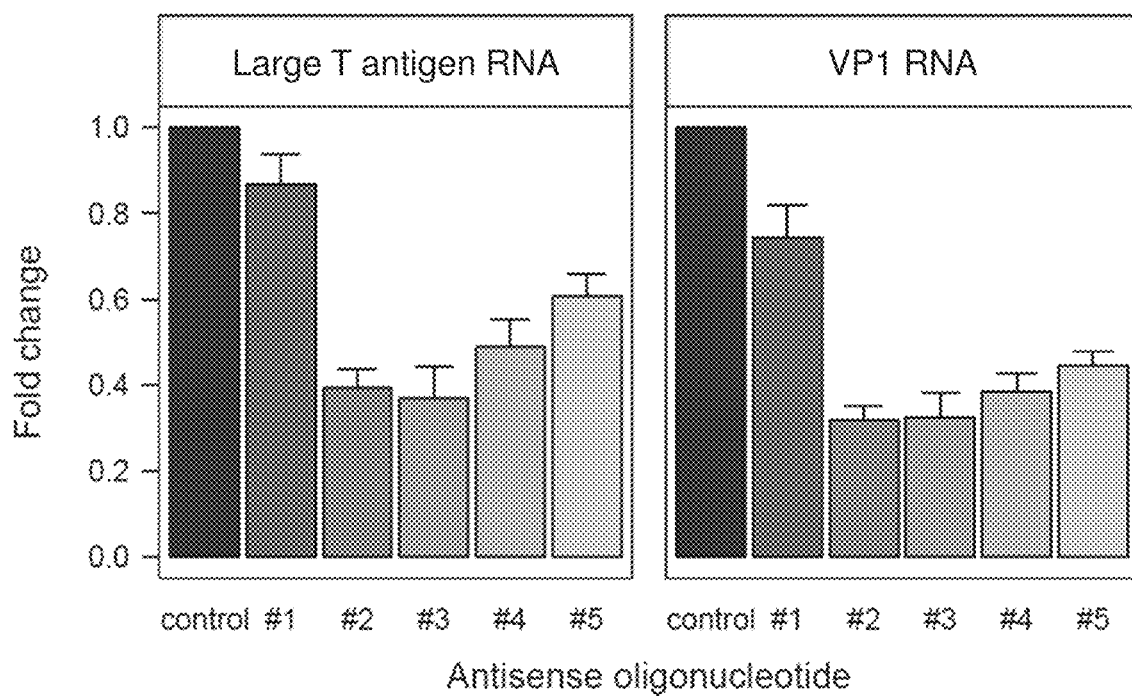
FIG. 4: TAg splice-modulating AONs reduce expression levels of TAg and VP1 mRNAs in BKPyV infected human epithelial cells. Left: Reduction in TAg RNA levels in scramble AON-treated HK2 cells versus HK2 cells treated with splice-modulating AONs #1, #2, #3, #4 and #5 at 7 days following infection with BKPyV virus at a multiplicity of infection of ~100 (n=5; $p<0.05$). Right: Reduction in VP1 RNA levels in scramble AON-treated HK2 cells versus HK2 cells treated with splice-modulating AONs #1, #2, #3, #4 and #5 following infection with BKPyV virus at a multiplicity of infection of ~100 (n=5; $p<0.05$).

We also tested whether a combination therapy of AONs #2 and #4 could more effectively reduce TAg and VP1 RNA levels. This combination was also selected based on the fact that the aforementioned Western blot for VP1 in AON-treated cells (FIG. 5) suggested that these two AONs lead to the most potent loss of VP1 protein. Based on TAg and VP1 mRNA expression levels, this combinatorial treatment did not yield evidence that suggested that together they were more efficacious (FIG. 4).

The observed reduction in VP1 shows that TAg splice-targeting AONs are effective. By reducing TAg RNA (and potentially protein expression), expression levels of the BKPyV late region genes and corresponding proteins are reduced. Moreover, alongside a role for VP1 in encapsulating the viral DNA, VP1 also serves a pivotal mediating role in the infectivity of newly-formed viral particles by binding to the cell surface of neighbouring and/or distant cells at sialic acids on glycans (Helle, F. et. al., Viruses, 2017). As such, the infectivity of BKPyV would likely be compromised upon a reduction (or in the absence) of VP1 protein.

TAg Splice-Targeting AONs Decrease BK Viral Titer

Figure 6:
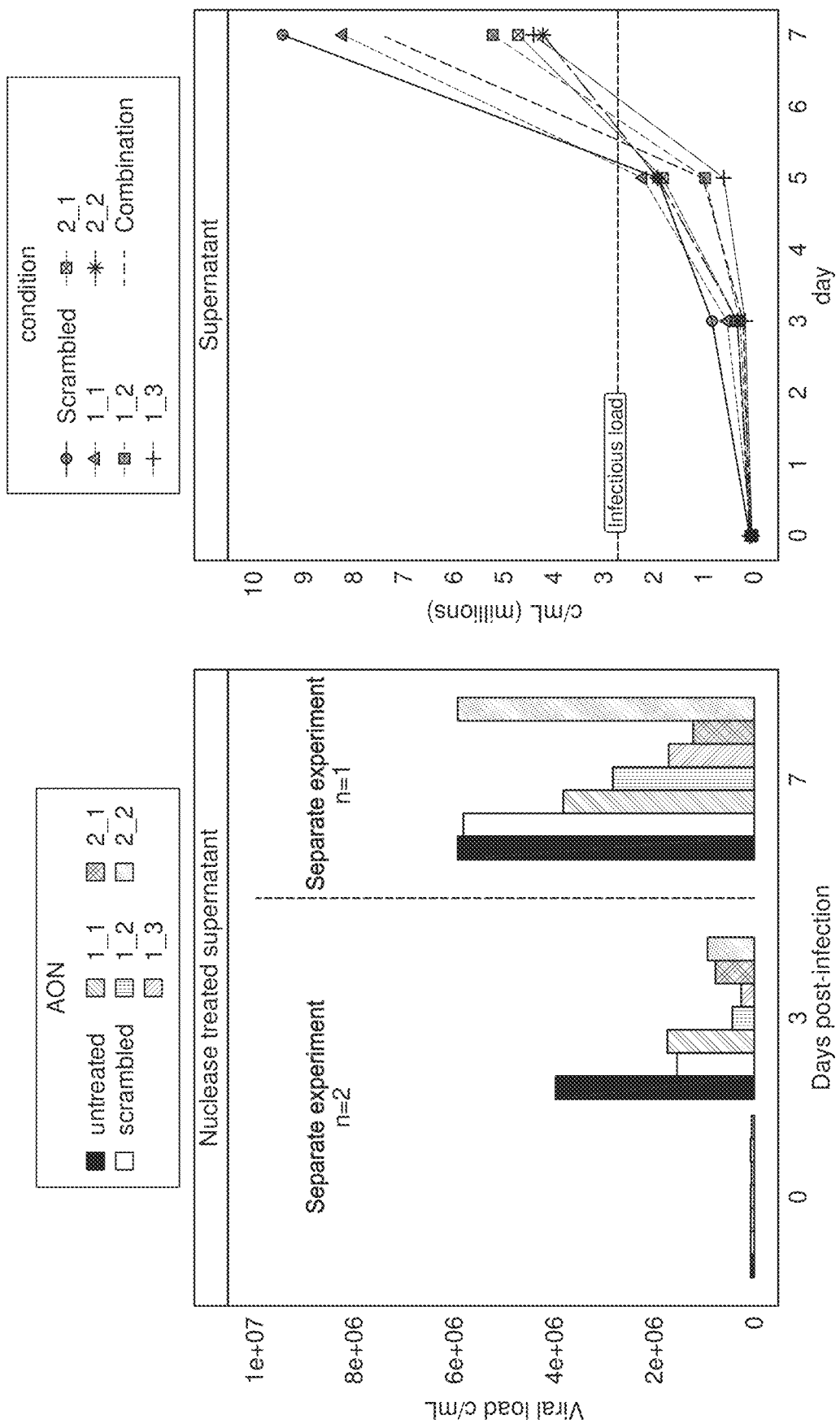
FIG. 6: TAg splice-modulating AONs reduce BK virus replication. Viral DNA concentrations in the culture supernatant were determined by the PCR analysis method for VP1 in the BKPyV genome. HK2 cells treated with AONs #2, #3 and #4 consistently reveal reduced levels of BKPyV genome in the culture supernatant, as compared to those treated with the scrambled AON.

Concomitant with our screens for TAg and VP1 RNA and protein levels (at day 7) in HK2 cells pre-treated with our TAg splice-targeting AONs, we also assessed the viral load in the culture supernatant at 3, 5 and 7 days after BKPyV infection. We determined whether the decrease in VP1 affected encapsulated viral DNA production, as a reduction in TAg expression could potentially impact both viral genomic replication and VP1 protein generation. We determined the virus particles in culture supernatant by quantitating encapsulated DNA. To discern between encapsulated and non-encapsulated DNA, we applied an (endo)nuclease treatment to digest non-encapsulated DNA. As shown in FIG. 6, these studies revealed that AON #1 at day 3 reduced viral DNA levels, but by 7 days that this level has normalized and is similar to viral DNA levels in scramble AON-treated cells (FIG. 6). AONs #2, #3 and #4 are characterized by reductions in viral titer at both time intervals, with AONs #2, #3 and #4 in particular attenuating encapsulated viral DNA up to 6-fold (FIG. 6). The aforementioned combination of AON #2 and #4 only slightly reduced viral load at days 3 and 7 (FIG. 6).

Thus AON-mediated attenuation of TAg and VP1 RNA and protein leads to a decrease in virus production.

Alkyl Modifications at the 2' Position of the Ribose Sugar

Figure 7:
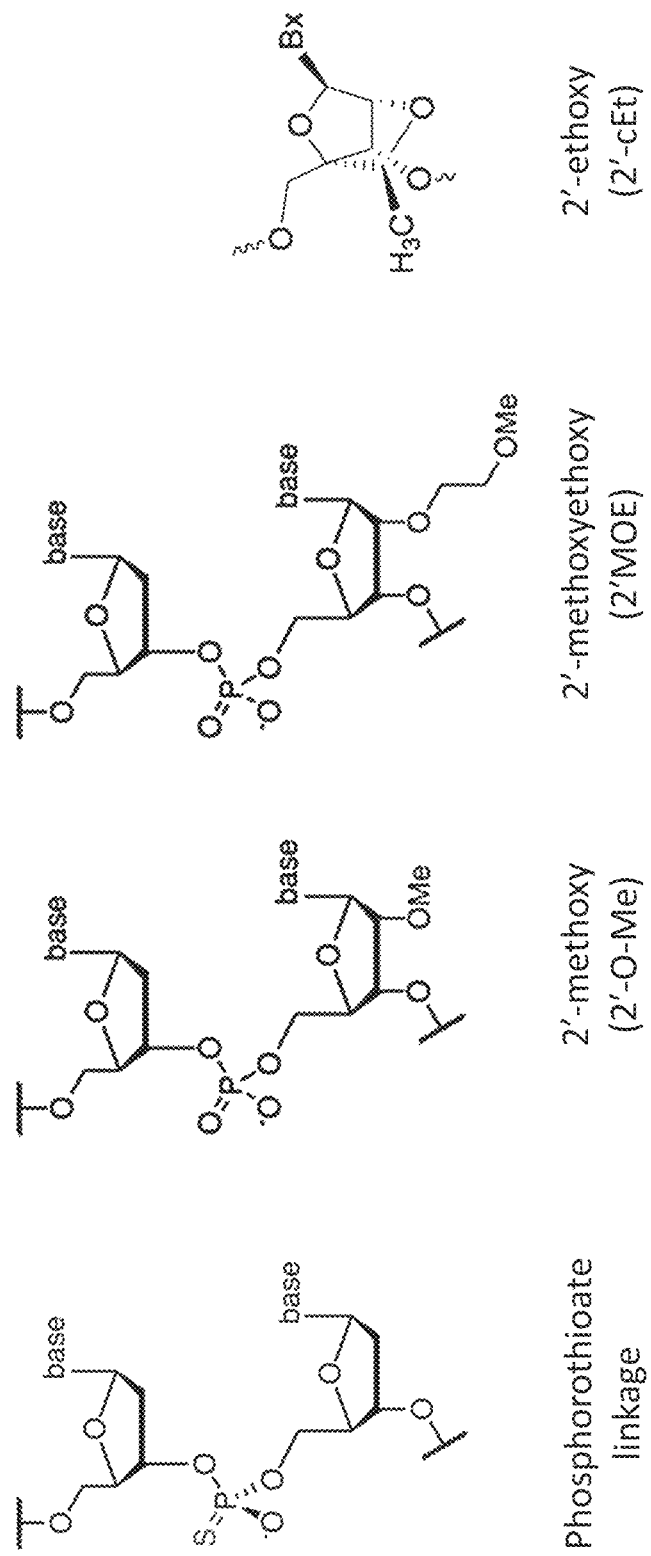
FIG. 7: Chemical modifications to AONs. Depicted are some chemical modifications that have been applied to the current TAg splice-modulating AONs (phosphorothioate backbone and 2'-OMe on ribose moiety). Other embodiments of these AONs could employ 2'-MOE or 2'-cEt modifications at this position. These modifications primarily serve to improve AON stability.

Altering the 2'-position of the ribose sugar on AONs impacts their capacity to reduce TAg and VP1 RNA and protein levels, and BKV DNA production (FIG. 7). The aforementioned data is based on a 2'-O methyl (2'-OMe) modification of the ribose sugar on each nucleotide within an antisense oligonucleotide. RNA and protein have been harvested from HK2 cells pre-treated with both 2'-OMe or 2'-methoxy (2'-MOE) nucleotides (see FIG. 7).

TAg Splice-Targeting AONs for Other Polyomaviruses

Figure 8:
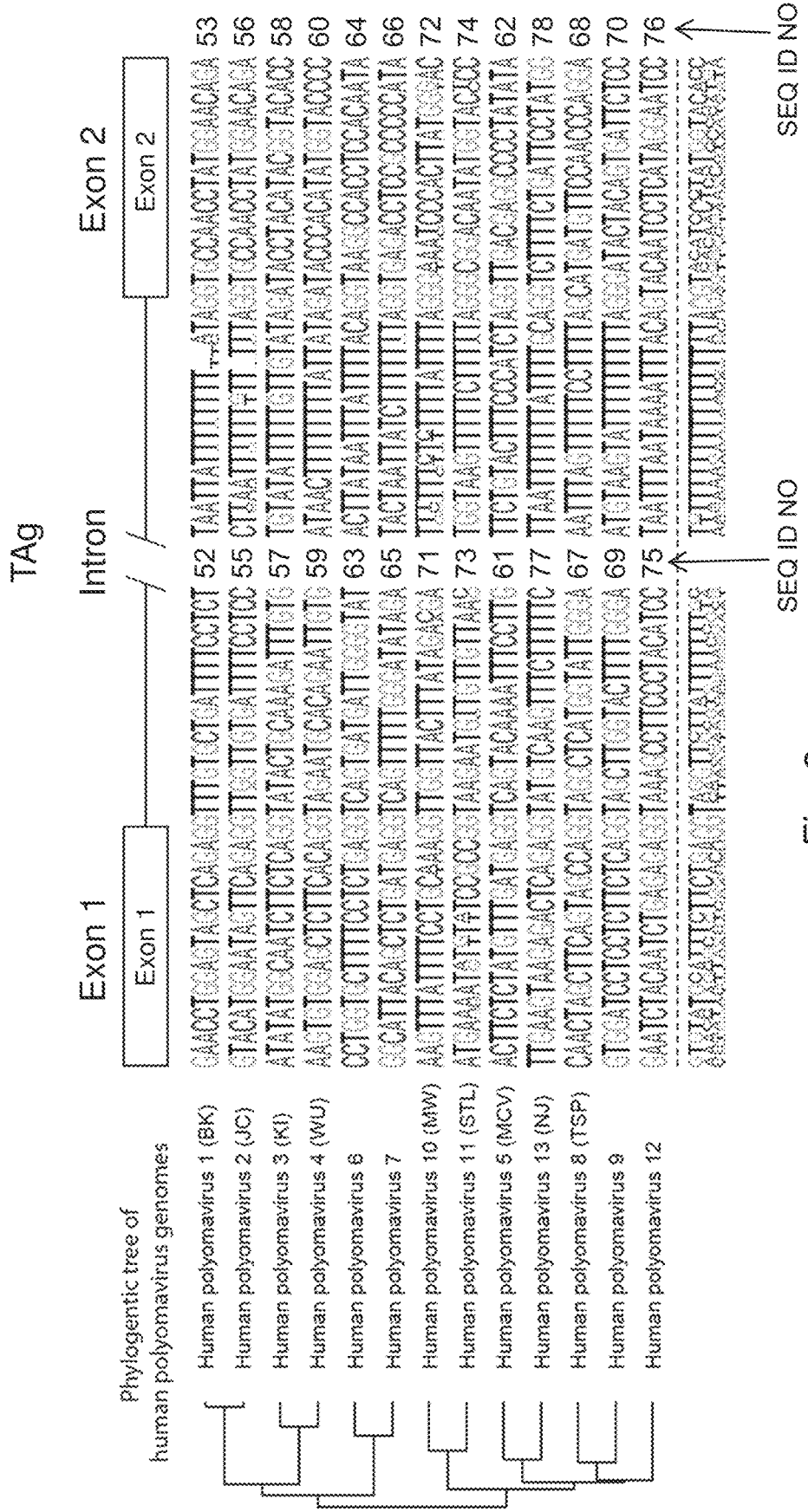
FIG. 8: Sequence similarity for the 13 polyomaviruses known to have human hosts. Of note, these strains cover the alpha, beta and delta genus, the majority of which have recently been identified. As shown in the phylogenetic tree information on the left side of the figure, BKPyV and JCPyV share considerable sequence similarity, suggesting that their co-localization in the proximal tubule epithelial cells of the kidney lends them to targeting with the herein described splice-modulating AONs.

Alongside BKV, we have also developed AONs that similarly target TAg for JC virus (JCV). JCV has 75% sequence similarity to BKV, a level of conservation that is also observed at the exon 1—intron junction, whereas the sequence similarity at the intron—exon 2 junction is virtually 100% (FIG. 8). AONs targeting exon 2 for BKV can thus also reduce JCV load. JCV can also infect kidney cells such as proximal tubule cells, which are believed to be a secondary site of infection, following initial infection via the tonsils and/or digestive tract. The TAg splice-targeting AONs, in particular those targeting the intron—exon 2 splice site can thus simultaneously abrogate BKV and JCV production. Moreover, we are generating novel AONs that target the unique JCV exon 1—intron sequence.

Given that the genomic sequence at the exon 1—intron and intron—exon 2 junctions for TAg have been determined for all known polyomaviruses, it is possible to design AONs that affect splicing of TAg in all of these polyomaviruses (FIG. 9).

Examples of suitable AON for other polyomaviruses are depicted in FIG. 9.

Example 2

Material and Methods
Phylogenetic Conservation of BKV Subtypes

Complete genomic sequences of BK polyomavirus isolates were downloaded from the publicly available NCBI database (before 07-09-2018). From these records, only the isolates reporting a complete genome were used for analysis. Isolates "MM" and "FNL-9" were removed due to a large deletion in the intron or duplication overlapping the acceptor splice site respectively. Identical sequences were removed, yielding 248 unique genomic sequences of which the accession numbers are provided below:

AB211369, AB211370, AB211371, AB211372, AB211373, AB211374, AB211375, AB211376, AB211377, AB211378, AB211379, AB211381, AB211382, AB211383, AB211384, AB211385, AB211386, AB211387, AB211388, AB211389, AB211390, AB211391, AB213487, AB217917, AB217918, AB217919, AB217920, AB217921, AB260028, AB260029, AB260030, AB260031, AB260032, AB260033, AB263912, AB263913, AB263914, AB263915, AB263916, AB263917, AB263918, AB263919, AB263920, AB263921, AB263922, AB263923, AB263924, AB263925, AB263926, AB263927, AB263928, AB263929, AB263930, AB263931, AB263932, AB263934, AB263935, AB263936, AB263938, AB269825, AB269826, AB269827, AB269828, AB269829, AB269830, AB269831, AB269832, AB269834, AB269836, AB269837, AB269838, AB269840, AB269841, AB269842, AB269843, AB269844, AB269845, AB269846, AB269847, AB269848, AB269849, AB269850, AB269851, AB269852, AB269853, AB269854, AB269855, AB269856, AB269857, AB269858, AB269859, AB269860, AB269861, AB269862, AB269863, AB269864, AB269865, AB269866, AB269867, AB269868, AB269869, AB298941, AB298942, AB298945, AB298946, AB298947, AB301086, AB301087, AB301089, AB301090, AB301091, AB301092, AB301093, AB301094, AB301095, AB301096, AB301097, AB301099, AB301100, AB301101, AB365130, AB365132, AB365133, AB365134, AB365136, AB365137, AB365138, AB365139, AB365140, AB365141, AB365142, AB365144, AB365145, AB365146, AB365148, AB365149, AB365150, AB365151, AB365153, AB365154, AB365156, AB365157, AB365158, AB365159, AB365160, AB365162, AB365164, AB365165, AB365166, AB365167, AB365168, AB365170, AB365173, AB365174, AB365175, AB365176, AB365178, AB369087, AB369088, AB369089, AB369090, AB369092, AB369093, AB369094, AB369095, AB369096, AB369097, AB369098, AB369099, AB369101, AB464953, AB464954, AB464956, AB464957, AB464958, AB464960, AB464961, AB464962, AB485695, AB485696, AB485697, AB485698, AB485699, AB485700, AB485701, AB485703, AB485704, AB485707, AB485709, AB485710, AB485711, AB485712, AY628224, AY628225, AY628226, AY628227, AY628228, AY628229, AY628230, AY628231, AY628232, AY628233, AY628234, AY628235, AY628236, AY628237, AY628238, DQ305492, EF376992, FR720308, FR720309, FR720310, FR720311, FR720312, FR720313, FR720315, FR720317, FR720318, FR720320, FR720321, JF894228, JN192431, JN192432, JN192433, JN192435, JN192437, JN192438, JN192439, JN192440, JQ713822, KF055891, KF055892, KF055893, KP412983, KP984526, KY114802, KY114803, KY132094, KY487998, LC029413, LC309239, LC309240, LT960370, M23122, MF358970, MF627830, MF627831, V01108.

Splice Site Conservation and Phylogenetic Trees

Whole-gene sequences of TAg, including intron sequences, were aligned using Prank (v.140603). Manual adjustments were made to the aligned sequences to adjust for imperfections when aligning deletions. A phylogenetic tree was constructed using the Neighbor-Joining method (MEGA version 10.0.5) with bootstrapping (1000 replications) and the Kimura 2-parameter model. The phylogenetic tree was further visualized in R ("ggtree") and sequence logos were constructed ("ggseqlogo") for the acceptor and donor splice sites to show nucleotide specific conservation between subtypes. Subtypes of sequences were determined using reference sequences described by Zhong et al (Zhong, J Gen Virol, 2009).

Oligonucleotide Design

Antisense oligonucleotides were designed as described in EXAMPLE 1. For in vivo studies, a 2'-MOE AON (HYB_01) without 5' 6-FAM label was used.

Animals

Male C57BL6/J mice between 6 and 10 weeks of age were intravenously injected with 40 mg/kg 2'-MOE AON without 5' 6-FAM label or saline (volume of +−100 uL corrected for body weight). Animals were sacrificed under isoflurane anesthesia using venous exsanguination 24 after administration of AON or saline. Organs were removed and fixed in formalin and paraffin embedding.

Cell Culture

Human kidney proximal tubular epithelial cells (HK2, ATCC®) were maintained in Dulbecco's Modified Eagle Medium:Nutrient Mixture F-12 (Gibco) supplemented with 3,3',5-Triiodo-L-thyronine sodium salt (Sigma-Aldrich), insulin-transferrin-selenium-ethanolamine (ITS-X; Sigma-Aldrich), human epidermal growth factor (EGF; Sigma-Aldrich), hydrocortison (Sigma-Aldrich), and 100 U/mL penicillin-streptomycin (Gibco). Human renal proximal tubular epithelial cells (PTEC, Sciencell Research Laboratories) were maintained in complete REGM™ renal epithelial cell growth medium (Lonza). Primary human astrocytes (Sciencell Research Laboratories) were maintained in complete Astrocyte Medium (Sciencell Research Laboratorie). IPSc-derived astrocytes and oligodendrocytes were maintained in complete BrainPhys™ Neuronal Medium (Stemcell Technologies). All cells were cultivated at 37° C., 5% $CO_2$.

AON Treatment and Viral Infection of Cells

Cells were seeded at the required cell density and cultivated overnight. Cellular uptake of AONs was achieved by cultivating cells in the presence of 50 nM AON with lipofectamine 2000 for 4 h (human astrocytes and iPSc astrocytes/oligodendrocytes, Invitrogen) or lipofectamine 3000 for 5 h (HK2 and PTEC, Invitrogen), after which the cells were washed in normal culture media. BKV infection of HK2 epithelial cells or human renal epithelial cells was performed as described in EXAMPLE 1. JCV infection of astrocytes/oligodendrocytes was achieved by cultivating the cells in the presence of JC polyomavirus (MAD-4 strain, ATCC® VR-1583™) overnight. The cells were washed extensively after infection in order to remove excess viral particles. Culture media was partially refreshed, and supernatant samples were taken at specific time points after infection to study viral particle production. Re-infection of cells was performed by taking the supernatant of wells containing infected cells after treatment. This supernatant was then diluted 2-fold and transferred to a new well containing uninfected, untreated cells for 2 h, after which the cells were washed extensively. The infected cells were washed after 7 days using 4% PFA.

Viral Load Determinations

Viral loads in the culture supernatant were performed as described in EXAMPLE 1, with the following exceptions. 1) 100 µL samples were collected from every well at every time point. 2) Unpackaged DNA was degraded using the TURBO DNA-free kit (Invitrogen) before isolation.

Real-Time qPCR

Isolation of RNA, cDNA synthesis and real-time qPCR was performed as described in EXAMPLE 1. However, after isolation of RNA, residual DNA was degraded using the TURBO DNA-free kit (Invitrogen). For the amplification of T-antigen splice variants, the Phusion® High-Fidelity PCR Kit was utilized using HF buffer and the following primers: forward ATGGAGCTCATGGACCTTTTAGG, reverse TGCAACTCTTGACTATGGGGG. QPCR detection of JC virus RNA was performed using the following primers:

Antibodies

The following primary antibodies were used: rabbit anti-SV40 VP1 (ab53977), mouse anti-SV40 T-antigen (PAb416), mouse anti-SV40 T-antigen (PAb108), rabbit anti-GAPDH (D16H11), biotinylated Lotus Lectin (LTL, B-1325). The rabbit anti-phosphorothioate antibody was kindly provided by Jonathan Watts (UMASS Medical School, Mass., USA). The following secondary antibodies were used: goat-anti-rabbit Alexa 488 (A11008), goat-anti-rabbit Alexa 568 (A11011), goat-anti-rabbit HRP (P044801-2) and streptavidin Alexa 532 (S11224).

Protein quantification Protein lysates were generated by lysing cells in lysis buffer containing 50 mM Tris-HCl, 150 mM NaCl, 1% SDS, 0.5% deoxycholate, 0.5% triton X-100 and protease inhibitors (pH 7.5). Sample protein concentrations were determined using Pierce™ BCA Protein Assay Kit (Thermo Fisher Scientific). Quantification of protein expression was performed using the Wes Simple Western automated immunoassay system with a 12-230 kDa Separation Matrix and anti-Rabbit detection module (ProteinSimple).

Immunohistochemistry For re-infection experiments, cells were fixed with 4% PFA and permeabilized in 0.3% Triton-X/3% BSA (Merck, Zwijndrecht, the Netherlands)/1% NGS (Dako, Amstelveen, Netherlands)/1% FCS in PBS for 1 h at RT. Primary antibody was incubated in 3% BSA/1% NGS/1% FCS in PBS at 4° C. overnight, after which cells were washed extensively and incubated with secondary antibody for 1 h at RT. Image acquisition and quantification of re-infected cells was performed using the ImageXpress Micro High-Content Imaging System and MetaXpress software using custom modules to identify and count (TAg+) nuclei. Further processing of in vivo images (colour deconvolution and thresholding) was performed using ImageJ.

Mouse organs were embedded in paraffin, cut and slides were dewaxed, rehydrated and endogenous peroxidases were quenched for 10 min at RT in 3% $H_2O_2$ in methanol. Antigen retrieval was performed using Proteinase K (Agilent, Amstelveen, the Netherlands) for 10 min at RT, followed by a blocking step using Background buster (Innovex, Gujarat, India). Between steps, slides were washed in TBS/Tween. Primary antibody incubation (anti-phosphorothioate or LTL) was performed at 4° C. in 2% BSA/5% NGS in TBS/Tween. Secondary antibody incubation was performed for 90 min at RT. Nuclei were stained using Hoechst 33258 (Molecular Probes, Leiden, the Netherlands) and slides were mounted using Prolong Gold (Invitrogen). Image acquisition was performed using the Pannoramic MIDI II (3DHISTECH, Budapest, Hungary).

Next Generation Sequencing

RNA-seq was performed on RNA samples derived from infected, AON-treated HK2 cells using Illumina sequencing technology. In short, sample quality was determined using the Fragment Analyzer and the NEBNext Ultra II Directional RNA Library Prep Kit for Illumina was used to process the sample(s). The sample preparation was per-

| Gene | Forward | SEQ ID NO | Reverse | SEQ ID NO |
| --- | --- | --- | --- | --- |
| GADPH | ACAACTTTGGTATCGTGGAAGG | 40 | GCCATCACGCCACAGTTTC | 41 |
| TAg | CACCCTGATAAAGGTGGGGAC | 42 | GCAAAACAGGTCTTCATCCCAC | 43 |
| VP1 | CCAAAGAATGCCACAGTGCAA | 44 | GTGGGATCAGGAACCCAACAT | 45 | formed according to the protocol "NEBNext Ultra II Directional RNA Library Prep Kit for Illumina" (NEB #E7760S/L). Briefly, rRNA was depleted from total RNA using the rRNA depletion kit (NEB #E6310). After fragmentation of the rRNA reduced RNA, a cDNA synthesis was performed. This was used for ligation with the sequencing adapters and PCR amplification of the resulting product. The quality and yield after sample preparation was measured with the Fragment Analyzer. The size of the resulting products was consistent with the expected size distribution (a broad peak between 300-500 bp). Clustering and DNA sequencing using the NovaSeq6000 was performed according to manufacturer's protocols. A concentration of 1.1 nM of DNA was used. NovaSeq control software NCS v1.5 was used. Image analysis, base calling, and quality check was performed with the Illumina data analysis pipeline RTA3.3.5 and Bcl2fastq v2.20.

The human reference Homo_sapiens.GRCh38.dna.primary_assembly was combined with the virus reference LC029411.1. The combined genome was used for alignment of the reads for each sample. The reads were mapped to the reference sequence using a short read aligner based on Burrows-Wheeler Transform (Tophat v2.0.14) with default settings. Based on the mapped locations in the alignment file the frequency of how often a read was mapped on a transcript was determined with HTSeq v0.6.1p1.

Splice Event Identification Using Eventpointer

In order to identify alternative splicing events in NGS data, "Eventpointer" was applied on reads mapped to the viral reference genome. The resulting splice events were quantified using Kallisto to generate percent spliced (PSI) values for each event. For statistical testing, the scrambled AON was used as the control condition.

Pacific Biosciences Long-Read Sequencing

RNA integrity was first assessed on a bioanalyzer. The cDNA synthesis was performed with the SMARTer cDNA synthesis kit (Takara) and specific large T products were amplified using Kapa HiFi HotStart Ready Mix (Roche). cDNA products were size selected after which amplicons were barcoded per sample using the SMRTbell Barcoded Adapter Complete Prep Kit (PacBio), then pooled equimolar and sequenced on a PacBio Sequel 1M v3 LR SMRT cell.

The identification, polishing, and annotation of transcripts was carried out using the Iso-Seq3 bioinformatics pipeline made public by Pacific Biosciences (https://github.com/PacificBiosciences/IsoSeq3). Reads were first classified into full-length and non-full-length based on the presence of sample-specific barcodes. To find transcript clusters, an isoform-level clustering algorithm (ICE) performs a pair-wise alignment and reiterative assignment of full-length reads to clusters based on likelihood. After ICE, partial reads are added to the isoform clusters to increase coverage for a final consensus using the Arrow algorithm. The output from the bioinformatics pipeline is a set of full-length transcript sequences that can be mapped to the reference sequence to construct an annotation file in GFF format. Based on the Arrow algorithm's predicted consensus accuracy, transcript sequences that had a predicted accuracy of >99% (excluding QVs from the first 100 bp and last 30 bp due to occasionally insufficient coverage for accurate estimation of accuracies) were considered HQ transcripts and used for further analysis. The HQ transcript sequences were mapped back to the reference sequence and filtered for >99% alignment coverage and >85% alignment identity. Redundant transcripts were collapsed to create a final dataset used in this study.

Results

Development of Novel BKV-Targeting AON

Figure 11:
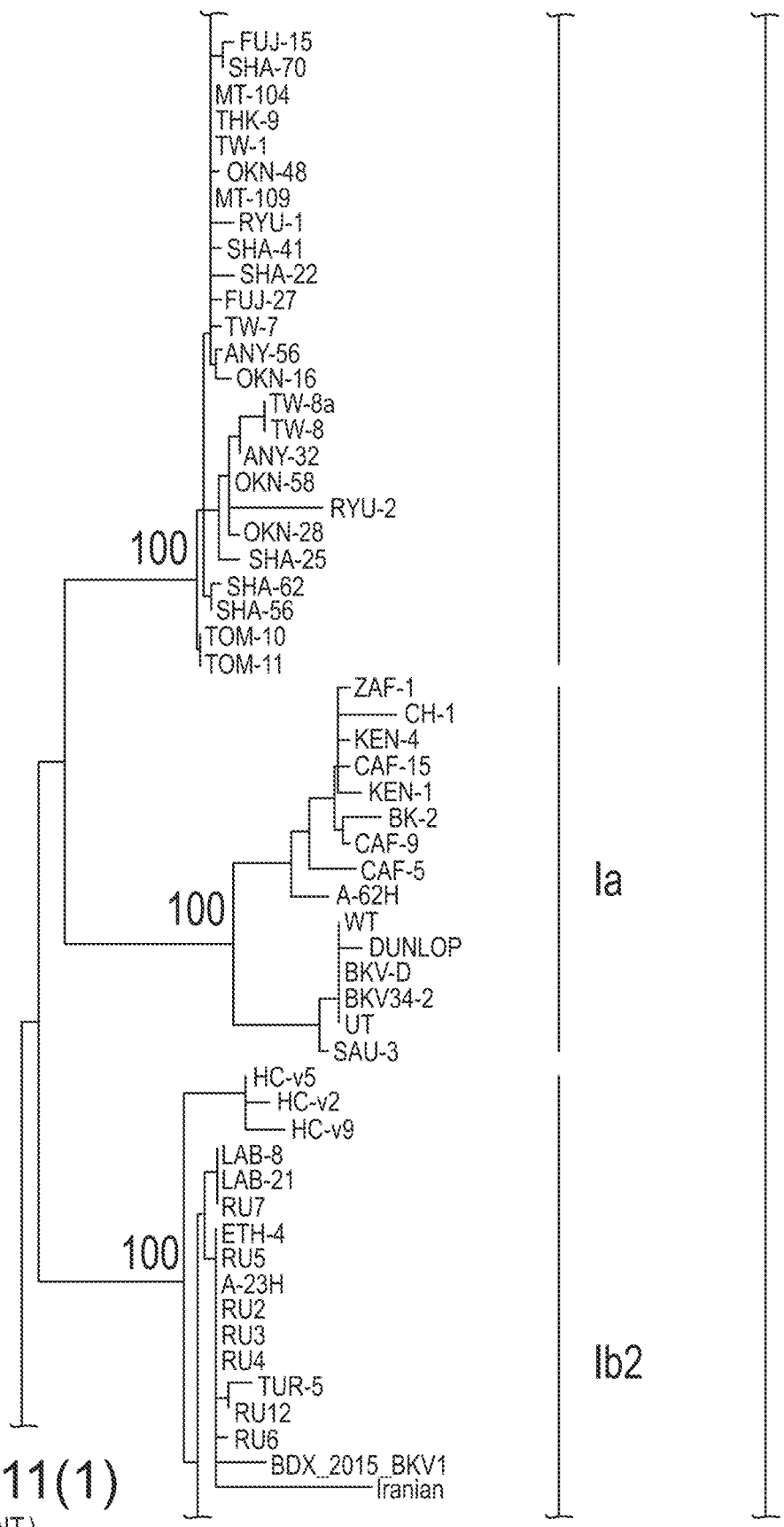
FIG. 11: Bioinformatic analysis of TAg splice site conservation for design of universal BKV-targeting AONs. Part 1: Phylogenetic tree containing whole gene TAg sequences for unique BKV isolates/strains showing clear distinctions between BKV subgroups. Part 2: Sequence logos for TAg splice sites with flanking regions (20 nucleotides) showing a high sequence conservation between subgroups. Sequences of antisense oligonucleotides (AONs) directed towards the exon 1—intron junction (HYB_01, HYB_02, HYB_03, HYB_06, HYB_07, HYB_08, HYB_09, HYB_10 and HYB_11) and intron—exon 2 junction (HYB_04, HYB_05, HYB_12, and HYB_13) of BKV TAg are provided.
Figure 11:
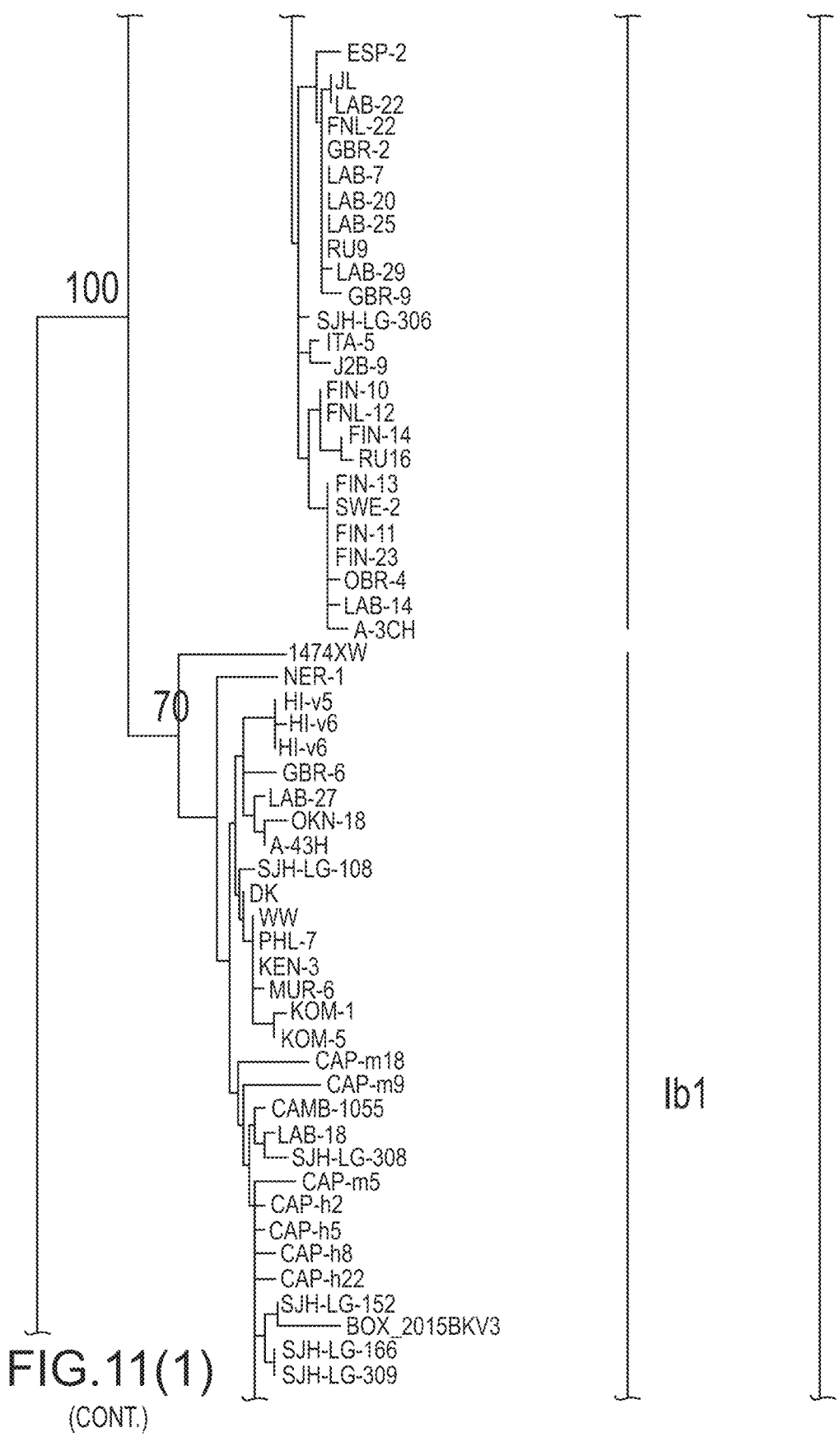
Figure 11:
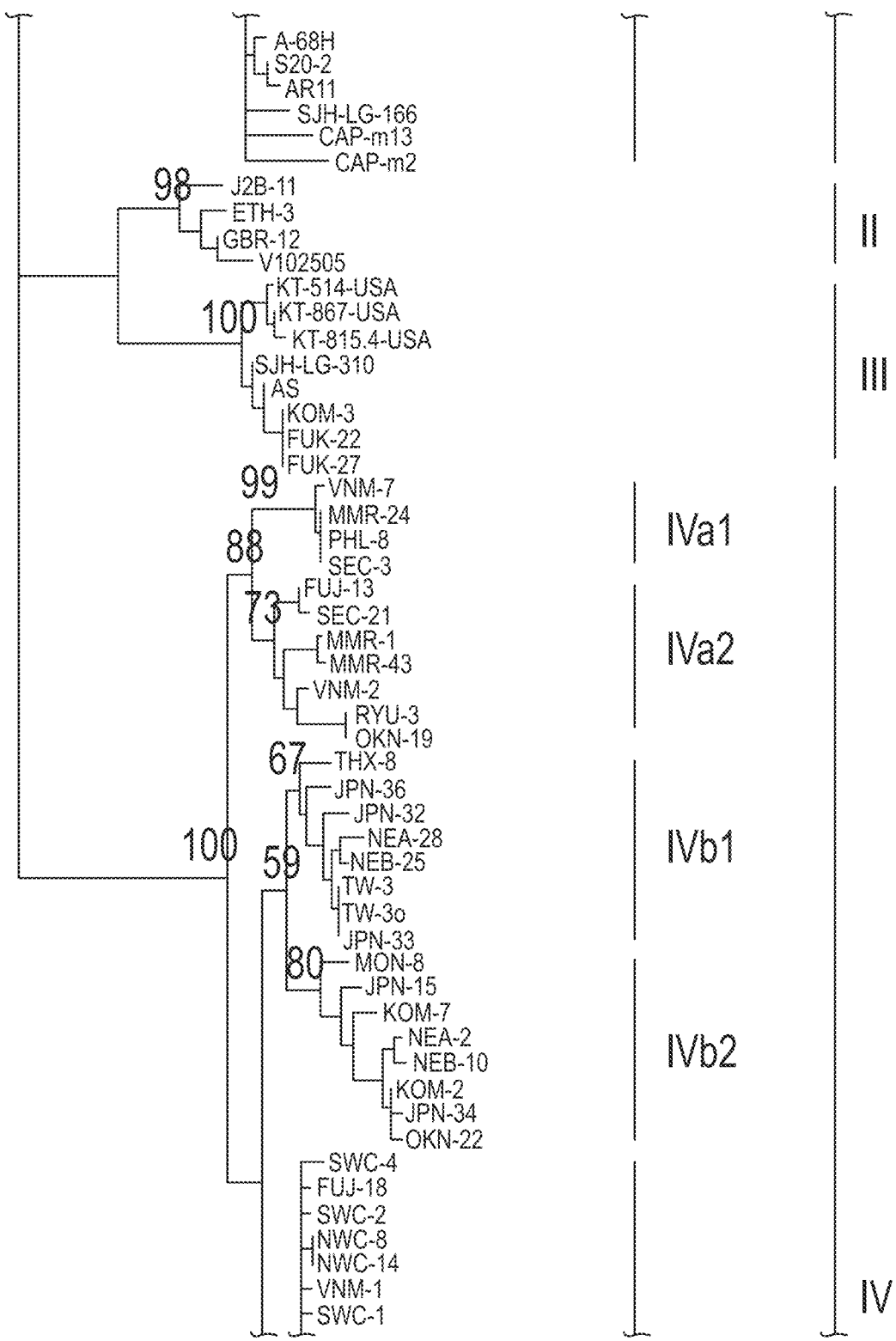
Figure 11:
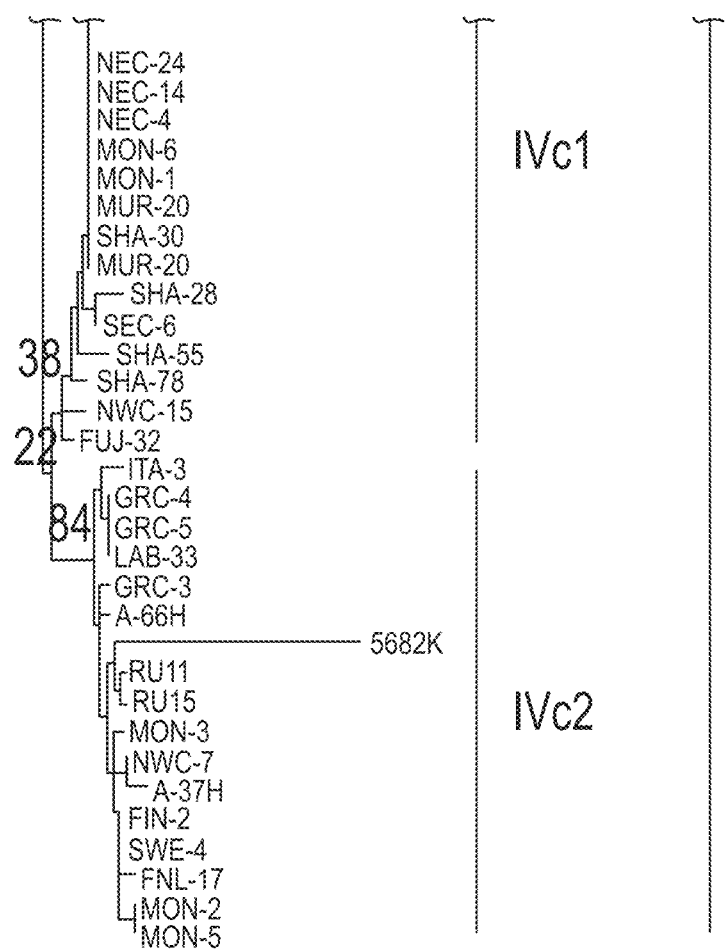

As shown in FIGS. 10 and 11, alongside our previous AONs, we elected to design 9 new AONs that target BKV TAg, 6 of which target the exon 1—intron portion (designated HYB_06, _07, _08, _09, _10, and _11), while 2 new AONs target the exon 2—intron portion (termed HYB_12 and _13). Alongside these 9 new TAg exon-intron junction targeting AONs, we also tested 2 AONs previously described by Santaris Pharma (WO2012/143427A1), which have different compositions relative to our AONs yet are complementary to a part of the exon 1—intron junction (SAN_74) or solely a part of exon 2 (SAN_73). Furthermore, we also designed and tested an AON that binds exclusively to the coding region of exon 1, namely HYB_14. The AONs progressively shift from primarily exonic to including significant intron-binding sequence for exon 1 targeting AONs, now collectively termed (HYB_01, _02, _03, _06, _07, _08, _09, _10, _11) and exon 2 targeting AONs (HYB_04, _05, _12 and _13).

AON-Mediated Reduction in BKV Tag RNA

Figure 12:
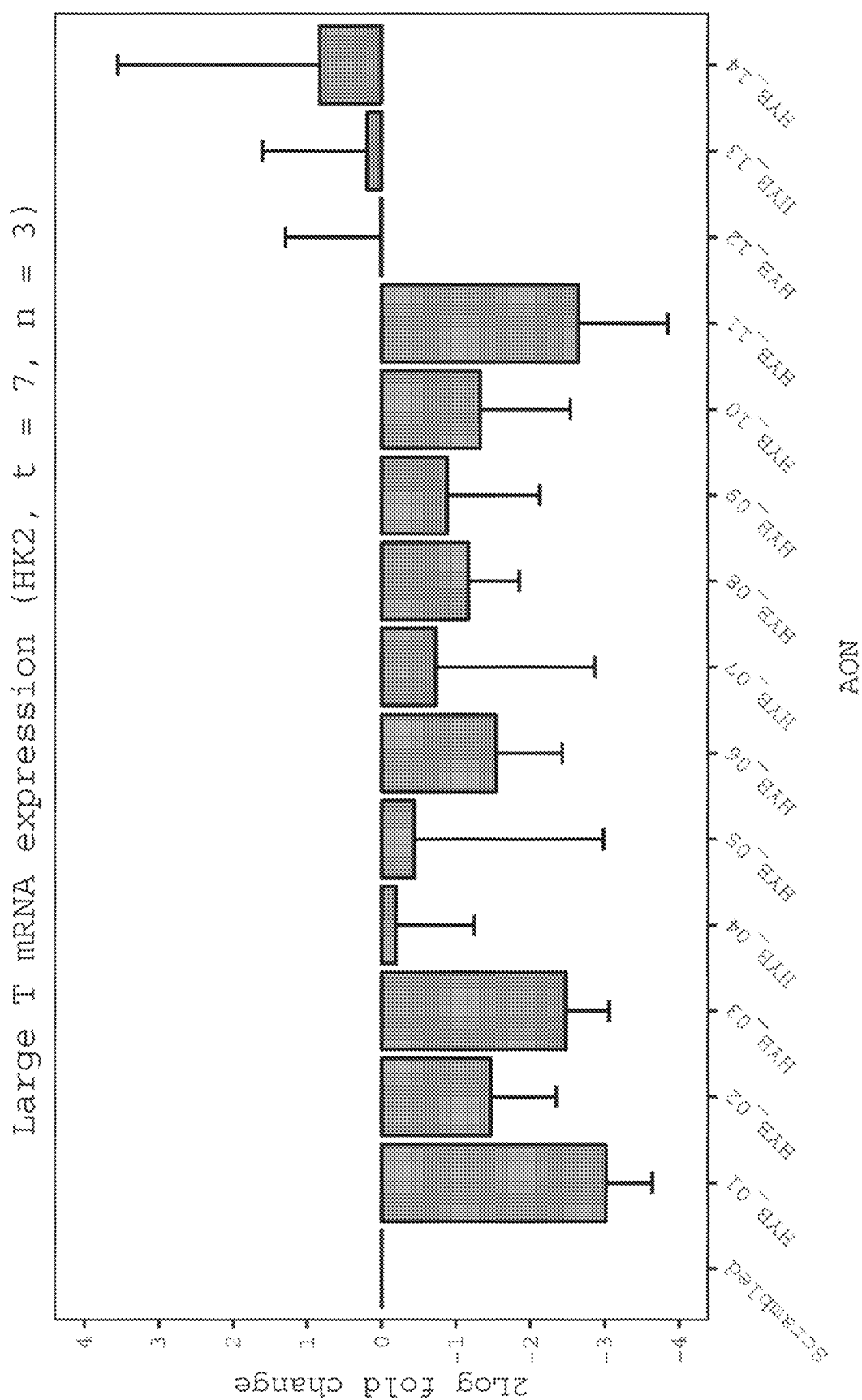
FIG. 12: TAg splice-modulating AONs reduce expression levels of TAg mRNAs in BKV-infected human kidney epithelial cells. Reduction in TAg RNA levels in scramble AON-treated HK2 cells versus HK2 cells treated with BKV-targeting AONs, after which cells were infected with BKV at a multiplicity of infection of ~100 (n=3 biological replicates). Note: HYB_14 binds exclusively to the exonic region of TAg exon 1 and does not target an exon—intron boundary.
Figure 19:
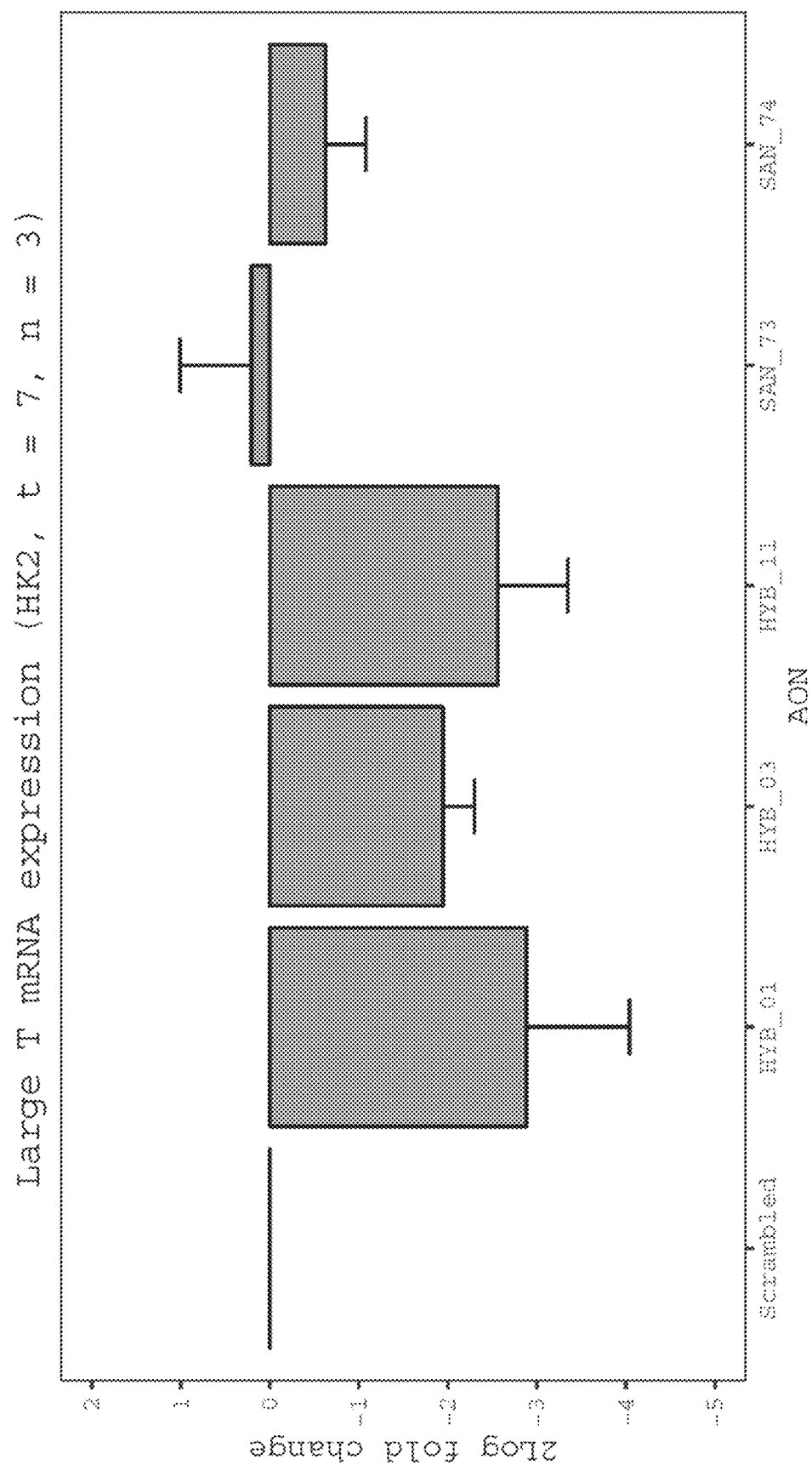
FIG. 19: TAg splice-modulating lead AONs reduce expression levels of TAg mRNAs in BKV-infected human kidney epithelial cells. Reduction in TAg RNA levels in scramble AON-treated HK2 cells versus HK2 cells treated with BKV-targeting lead AONs (HYB_01, HYB_03 or HYB_11), after which cells were infected with BKV at a multiplicity of infection of ~100 (n=3 biological replicates). Note: SAN_73 and SAN_74 are previously described AONs (16 nucleotides in length). These data are representative of a biological n=3.

The BKV-targeting AONs displayed varying ranges of potency in reducing TAg mRNA levels. As shown in FIGS. 12 and 19, of the 14 AONs designed to target the exon-intron junction of TAg, HYB_01, HYB_03 and HYB_11 induced the greatest reductions in TAg mRNA expression, generally in the range of 8- or greater-fold attenuation in the RNA levels of this viral DNA driver at 7 days post-infection.

Figure 18:
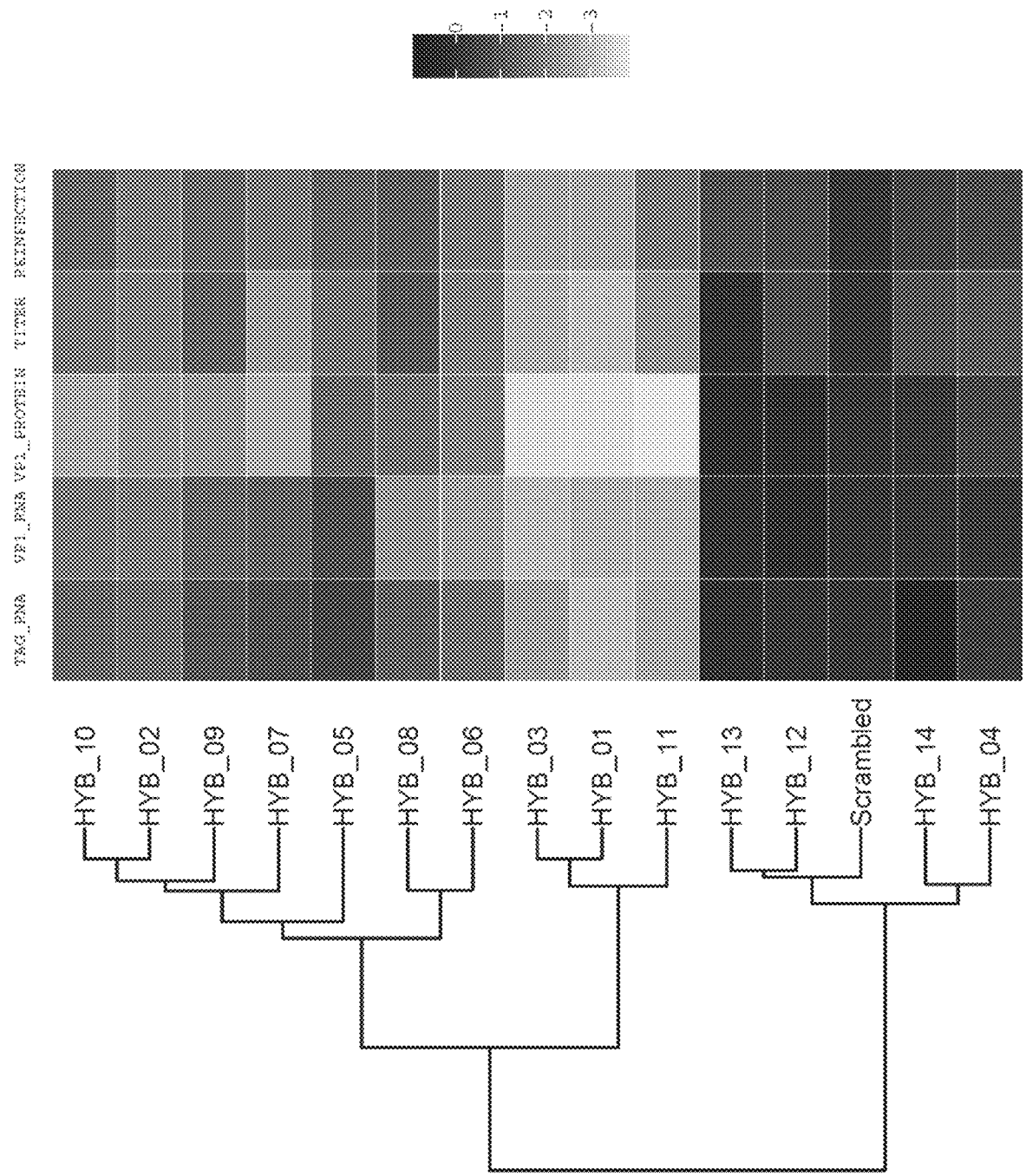
FIG. 18: Heatmap depicting cumulative effects of BKV-targeting AON treatment on various aspects of BKV infection of HK2 cells. Summary of effects observed on TAg and VP1 mRNA, VP1 protein, viral particle production and re-infection. Scale indicates that black represents little-to-no effect while white indicates large effect (2 log fold change compared to scrambled, n=3).
Figure 25:
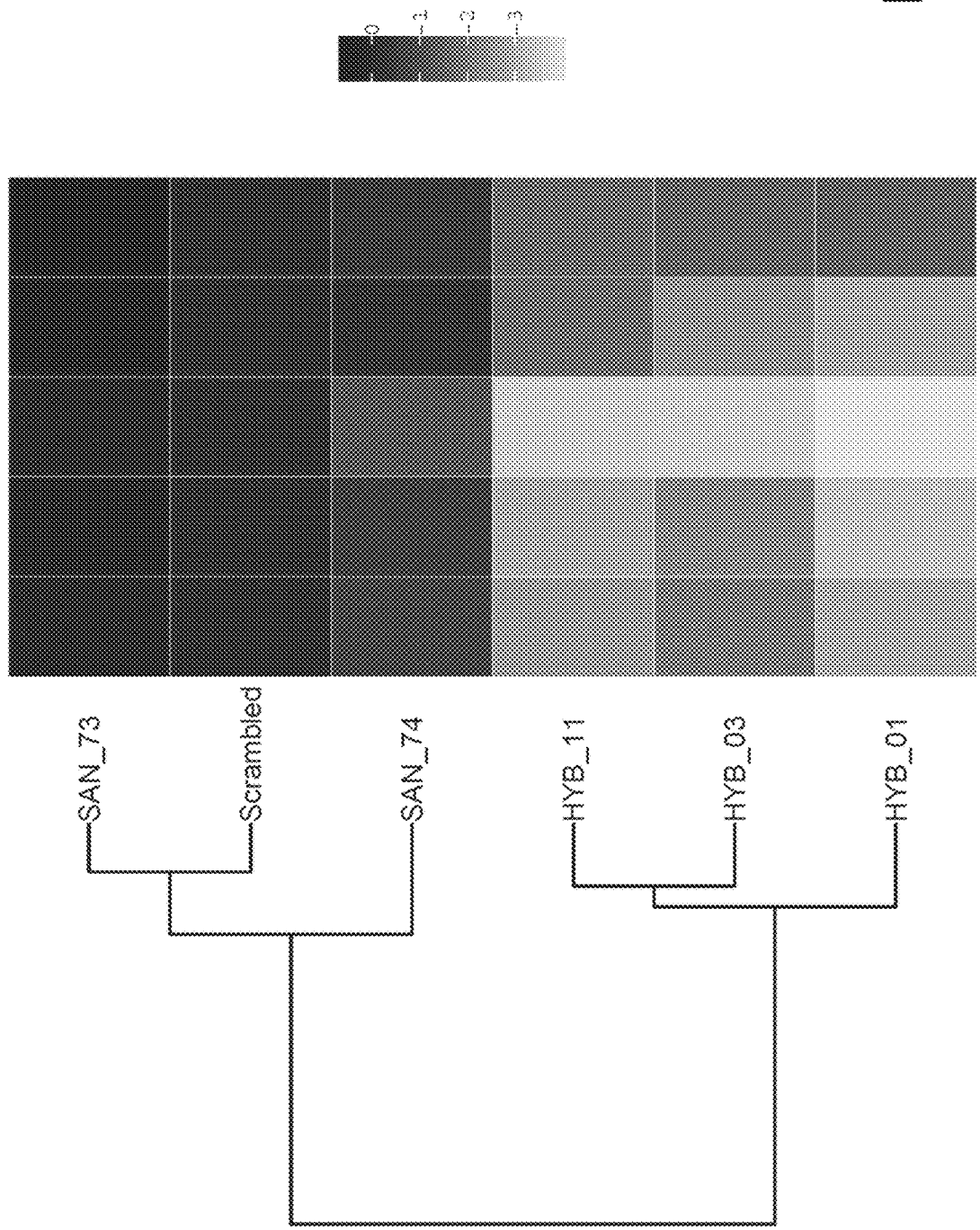
FIG. 25: Heatmap depicting cumulative effects of BKV-targeting lead compound AON treatment on various aspects of BKV infection of HK2 cells. Summary of effects observed on TAg and VP1 mRNA, VP1 protein, viral particle production and re-infection for HK2 cells pre-treated with our lead compound AONs (HYB_01, HYB_03 or HYB_11). Scale indicates that black represents little-to-no effect while white indicates large effect (2 log fold change compared to scrambled, n=3).

Furthermore, our data also suggest that AONs targeting the exon 1—intron junction is more effective in reducing TAg mRNA levels than AONs targeting the exon 2—intronic junction (HYB_04, HYB_05, HYB_12 and HYB_13). This trend is bioinformatically depicted in FIGS. 18 and 25, where solely HYB_05 clusters with the AONs that target the exon 1—intronic junction. Similarly, SAN_73 and SAN_74 proved largely ineffective in reducing TAg mRNA expression levels. Of note, these reductions in TAg mRNA are observed in the setting a high MOI, namely in the range of 100.

Figure 28:
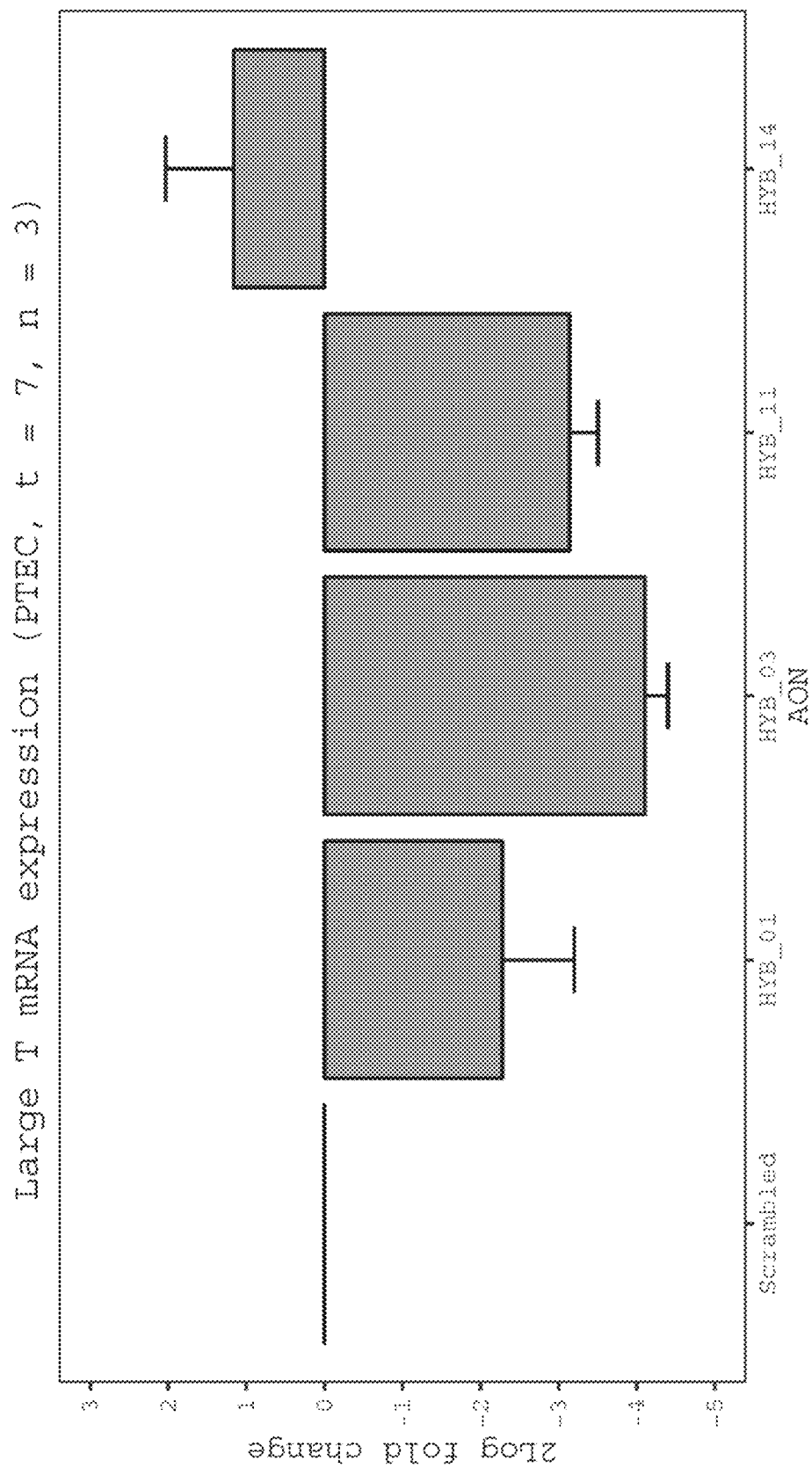
FIG. 28: TAg splice-modulating lead AONs reduce expression levels of TAg mRNAs in BKV-infected human primary proximal tubule epithelial cells (hPTECs). Reduction in TAg RNA levels in scramble AON-treated hPTECs versus hPTECs treated with BKV-targeting lead AONs (HYB_01, HYB_03 or HYB_11) or HYB_14, after which cells were infected with BKV at a multiplicity of infection of ~100 (n=3 biological replicates). These data are representative of a biological n=3.

Alongside HK2 cells, we also tested our BKV-targeting AONs in primary proximal tubule epithelial cells (hPTECs). Based on the significant and consistent reductions in TAg mRNA expression levels observed in HK2 cells with HYB_01, HYB_03 and HYB_11, we elected to proceed at this phase with these three being designated our 'lead compounds'. As shown in FIG. 28, HYB_01, HYB_03 and HYB_11 all dramatically reduced expression of TAg mRNA in hPTECs (n=3 biological replicates), while HYB_14 proved ineffective in reducing TAg mRNA levels in hPTECs.

Figure 26:
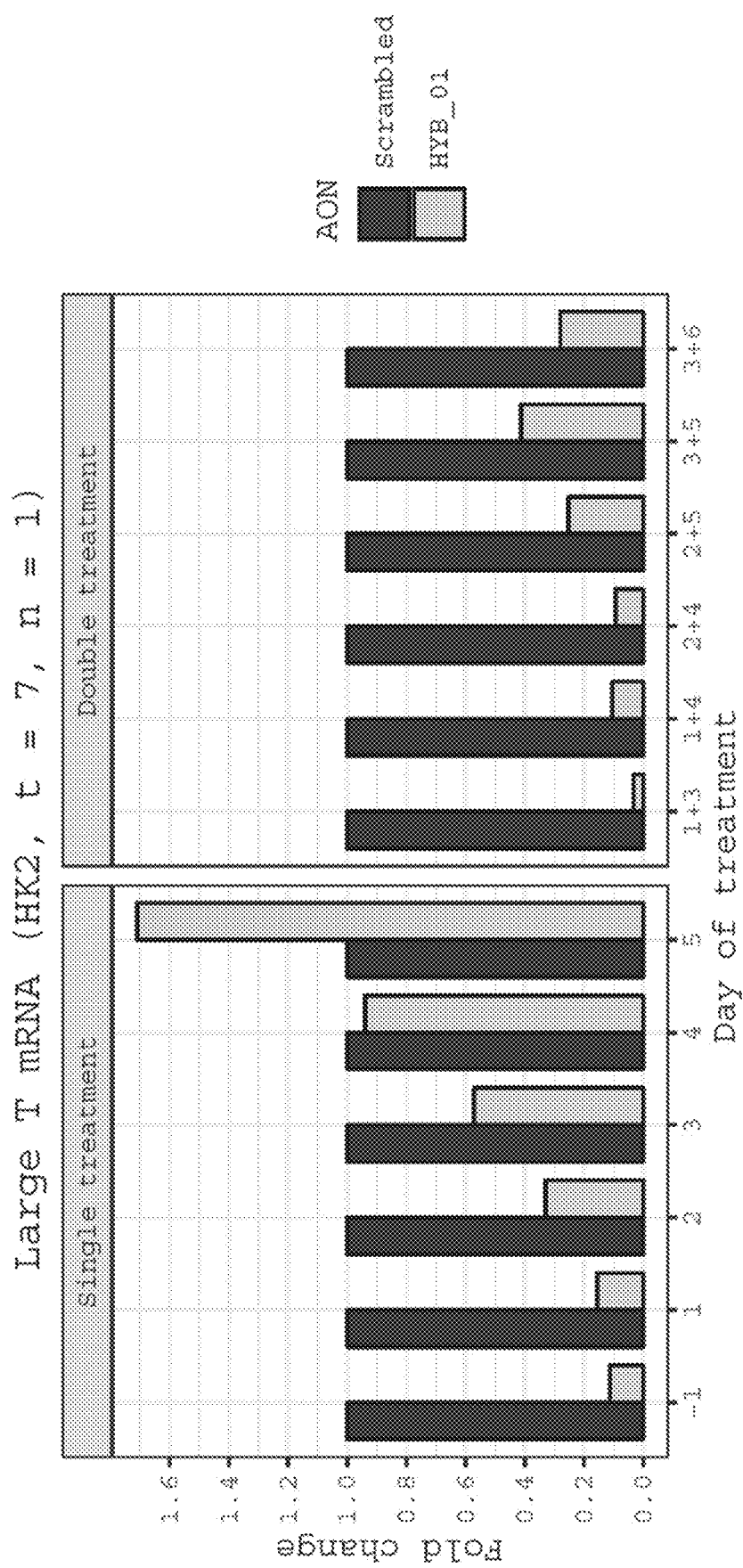
FIG. 26: Efficacy of TAg splice-modulating AON to reduce TAg mRNA expression in HK2 pre-infected with BKV. As opposed to pre-AON treatment, we first infected HK2 cells with BKV, and subsequently assessed the efficacy with which the AONs could reduce TAg mRNA expression levels. Left panel: single dosing of AONs post-infection significantly reduced expression levels of TAg mRNA, albeit that addition of AON at later timepoints appears less efficacious. Right panel: multiple doses of the BKV-targeting AON more potently reduces TAg mRNA expression levels. It is noted that RNA expression levels for all time points of treatment were determined at t=7 post infection, resulting in shorter exposures to treatment for later time points compared to early treatment. Data are representative of biological n=1.
Figure 27:
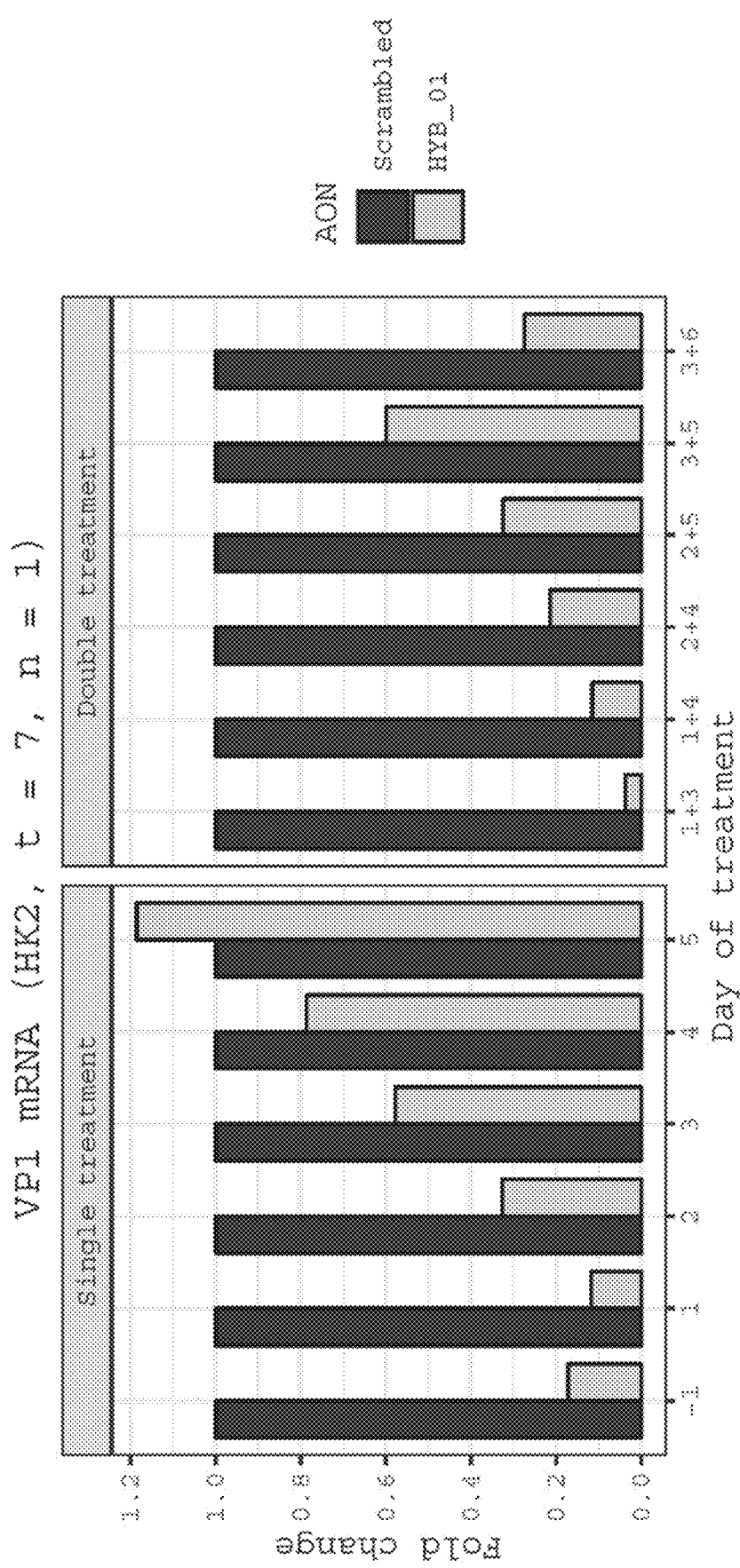
FIG. 27: Efficacy of TAg splice-modulating AON to reduce VP1 mRNA expression in HK2 pre-infected with BKV. As opposed to pre-AON treatment, we first infected HK2 cells with BKV, and subsequently assessed the efficacy with which the AONs could reduce VP1 mRNA expression levels. Left panel: single dosing of AONs post-infection significantly reduced expression levels of VP1 mRNA, albeit that addition of AON at later timepoints appears less efficacious. Right panel: multiple doses of the BKV-targeting AON more potently reduces VP1 mRNA expression levels. It is noted that RNA expression levels for all time points of treatment were determined at t=7 post infection, resulting in shorter exposures to treatment for later time points compared to early treatment. Data are representative of biological n=1.

Interestingly, the majority of our studies involve pre-treatment with AON prior to infection with BKV. Preliminary studies in which we first infected HK2 cells with BKV and subsequently treated the cells with AON (namely HYB_01) revealed that our BKV-targeting AONs can efficiently repress BKV TAg expression in cells that harbour BKV 7 days post-infection (FIG. 26, left panel), and that the administration of multiple dosages post-infection can potentially further suppress TAg mRNA expression levels (FIG. 26, right panel).

AON-Mediated Reduction of VP1 RNA and Protein

Figure 13:
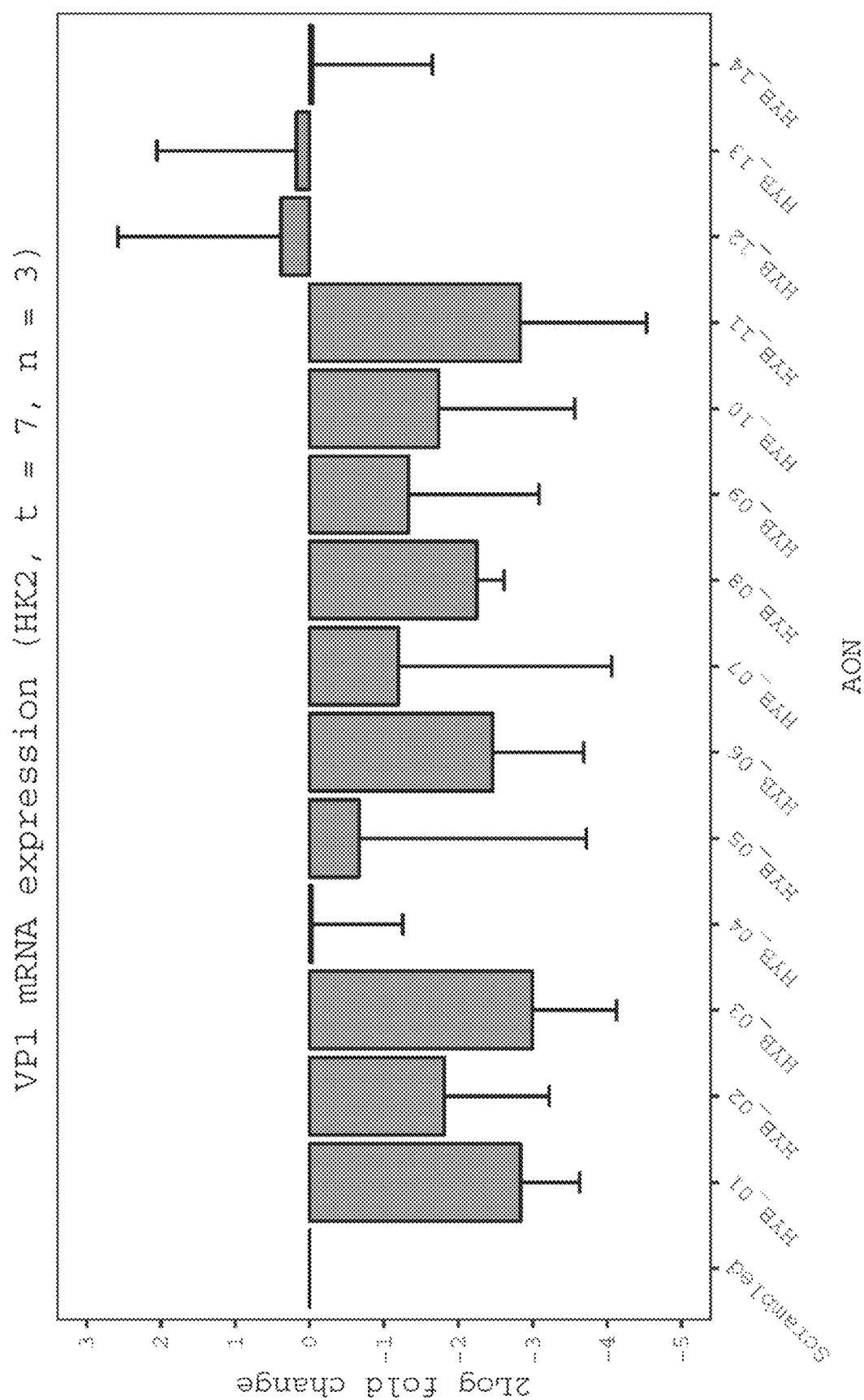
FIG. 13: TAg splice-modulating AONs reduce expression levels of VP1 mRNAs in BKV-infected human kidney epithelial cells. Reduction in VP1 RNA levels in scramble AON-treated HK2 cells versus HK2 cells treated with BKV-targeting AONs, after which cells were infected with BKV at a multiplicity of infection of ~100 (n=3 biological replicates). Note: HYB_14 binds exclusively to the exonic region of TAg exon 1 and does not target an exon—intron boundary.
Figure 14:
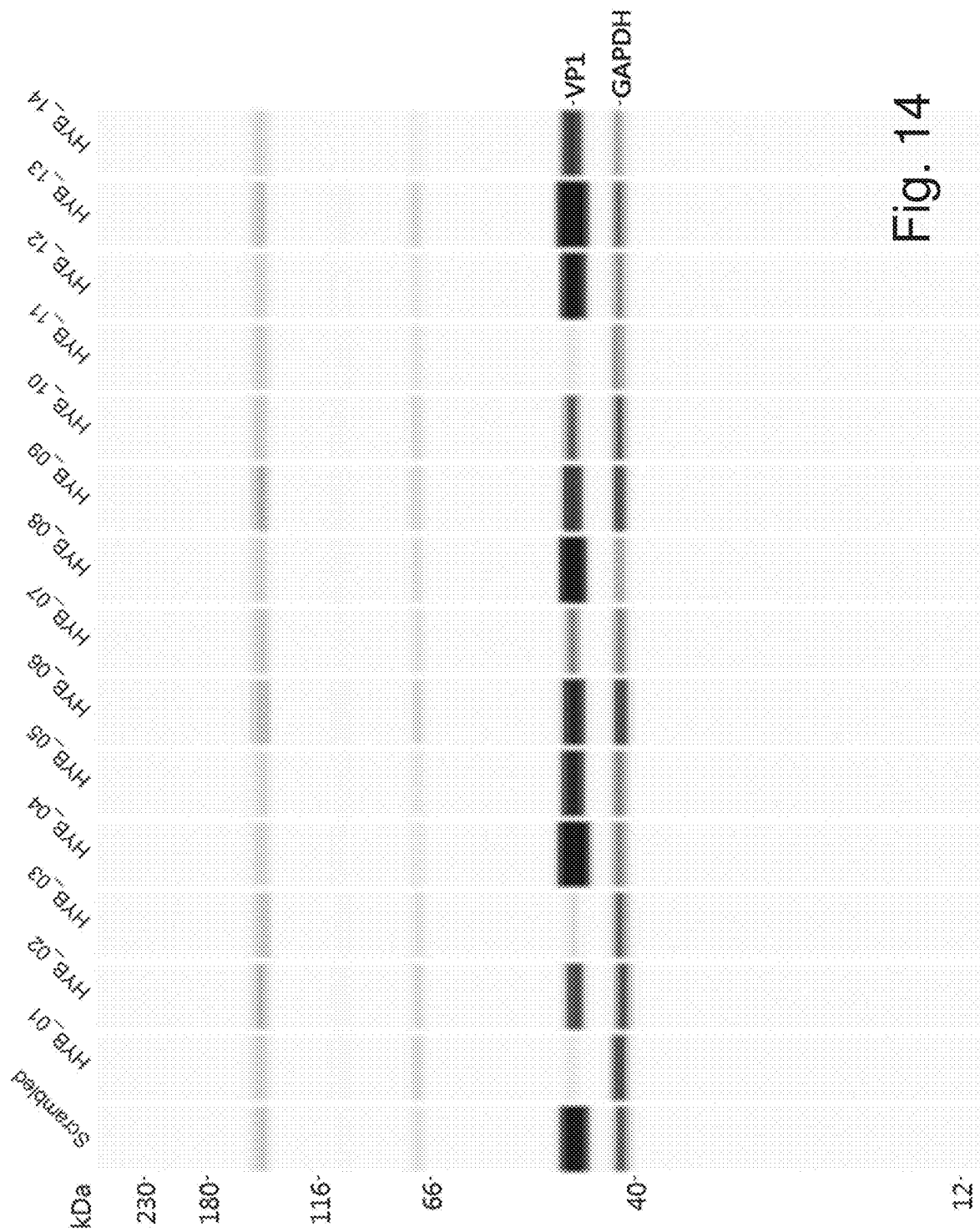
FIG. 14: TAg splice-modulating AONs reduce VP1 protein expression levels in BKV-infected human kidney epithelial cells. Representative Western blot analysis of cellular lysates harvested from BKV-targeting AON-treated HK2 cells. Blot depicts VP1 protein levels of lysates harvested 7 days post-infection with BK polyomavirus at a multiplicity of infection of ~100 (n=3 biological replicates).
Figure 15:
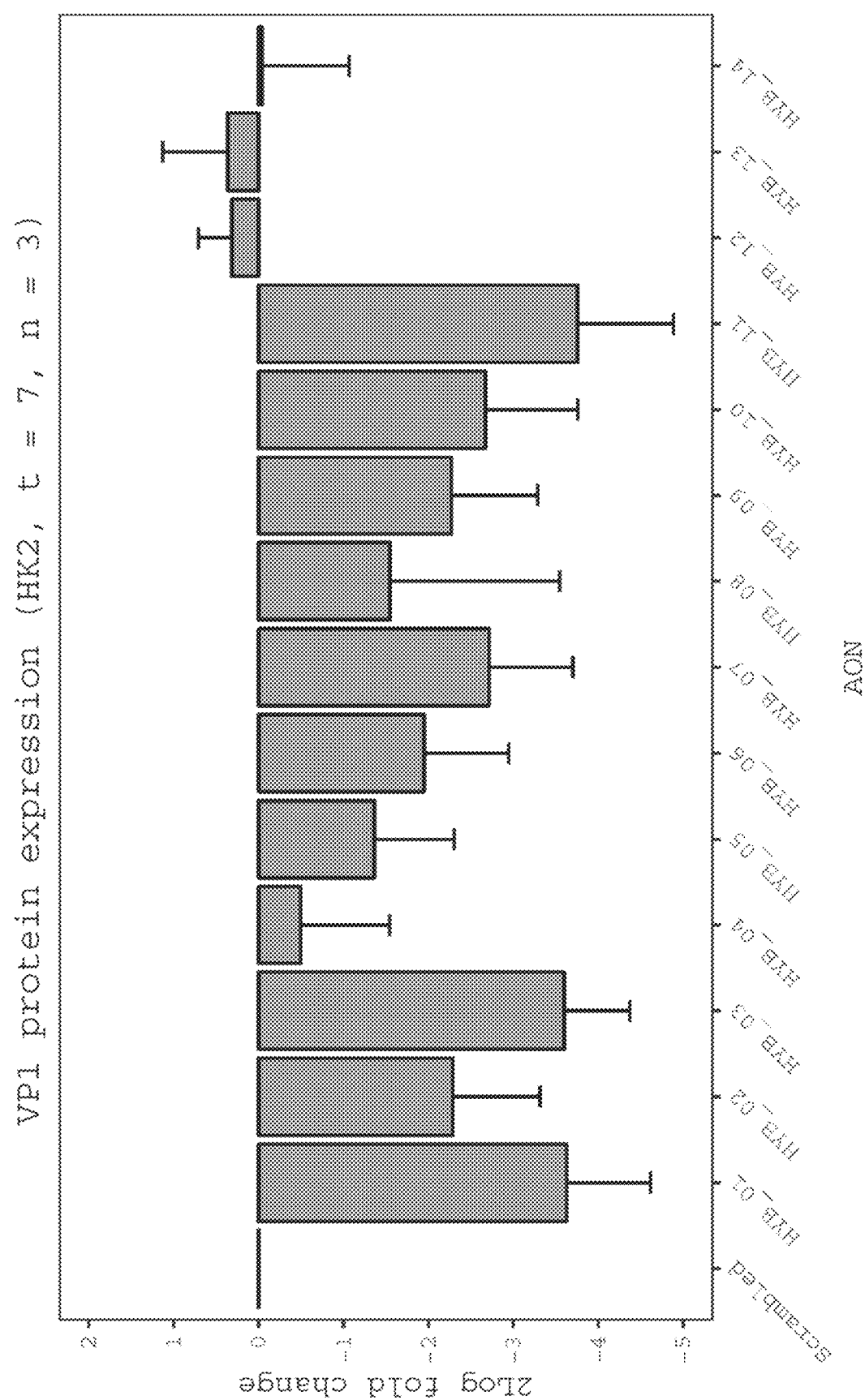
FIG. 15: Quantification of VP1 protein expression levels in human kidney epithelial cells following treatment with BKV-targeting AONs and infected with BKV. Quantification of Western blot analysis of HK2 cellular lysates harvested 7 days post-infection with BK polyomavirus at a multiplicity of infection of ~100. Scramble AON-treated HK2 cells were used as a control, and all values are in log 2 scale (n=3 biological replicates). Note: HYB_14 binds exclusively to the exonic region of TAg exon 1 and does not target an exon—intron boundary.
Figure 20:
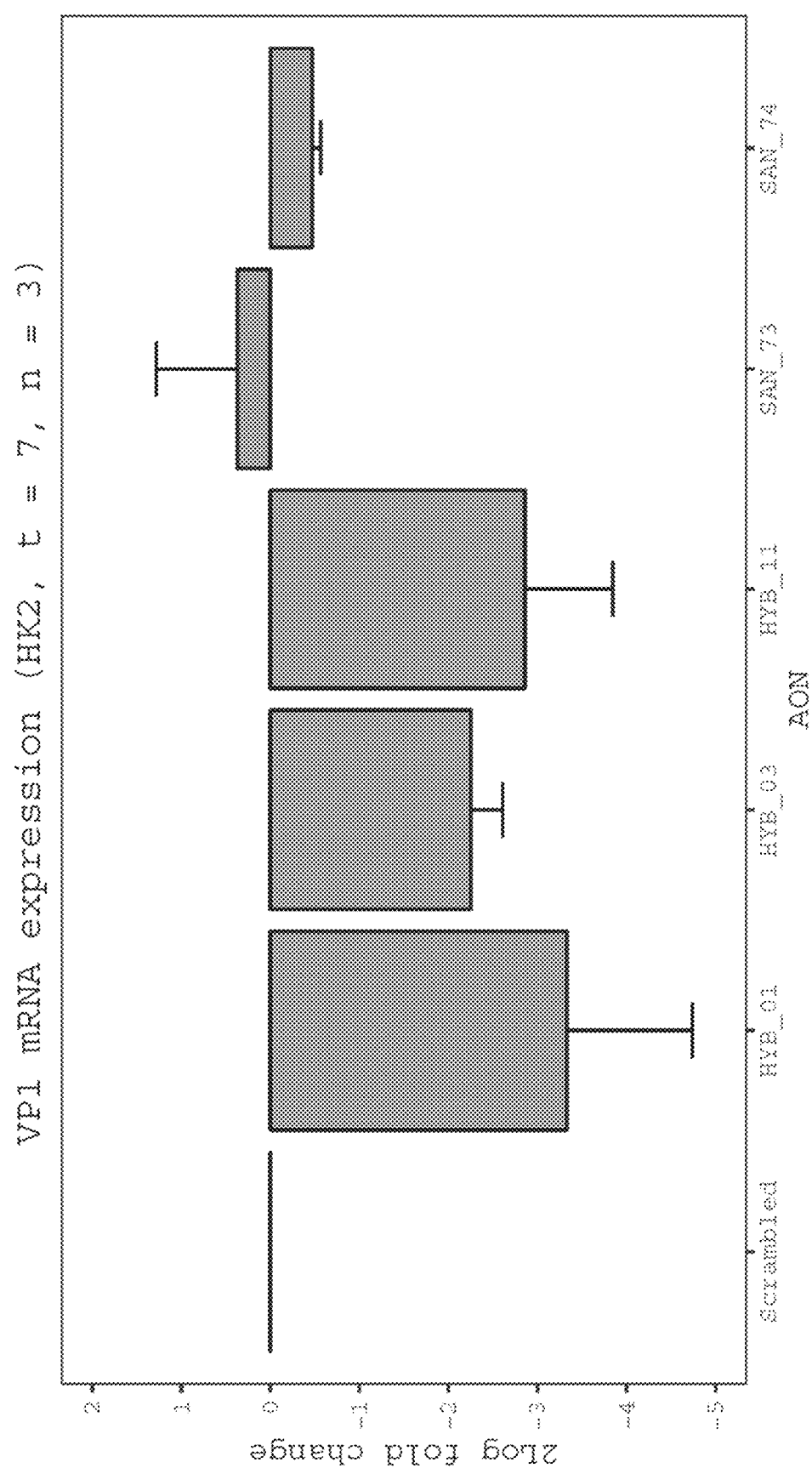
FIG. 20: TAg splice-modulating lead AONs reduce expression levels of VP1 mRNAs in BKV-infected human kidney epithelial cells. Reduction in VP1 mRNA levels in scramble AON-treated HK2 cells versus HK2 cells treated with BKV-targeting lead AONs (HYB_01, HYB_03 or HYB_11), after which cells were infected with BKV at a multiplicity of infection of ~100. Note: SAN_73 and SAN_74 are previously described AONs (16 nucleotides in length). These data are representative of a biological n=3.
Figure 21:
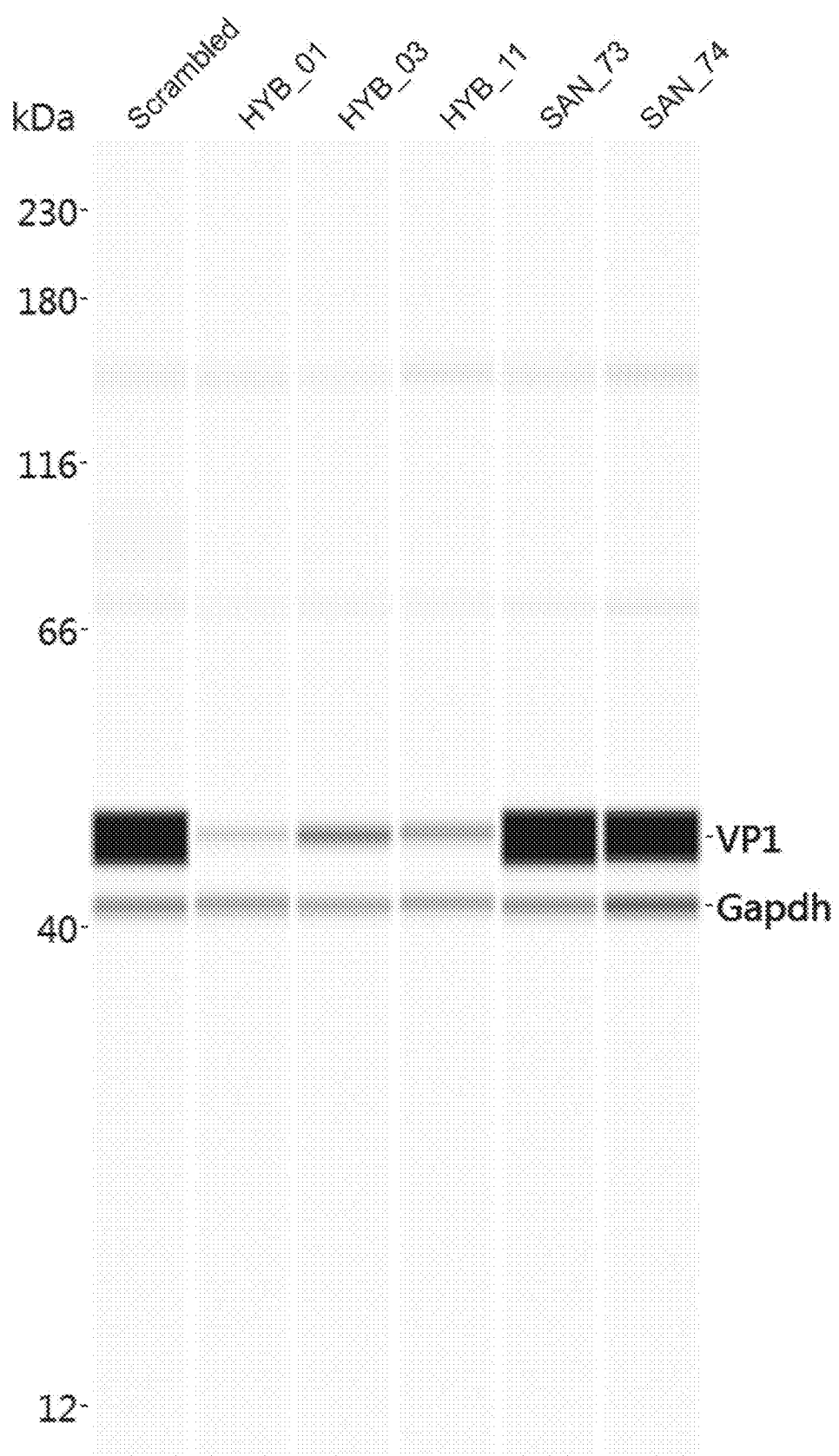
FIG. 21: TAg splice-modulating lead AONs reduce VP1 protein expression levels in BKV-infected human kidney epithelial cells. Representative Western blot visualization of VP1 protein levels in cellular lysates harvested from HK2 cells treated with BKV-targeting lead compound AONs and 7 days post-infection with BK polyomavirus at a multiplicity of infection of ~100 (n=3 biological replicates).
Figure 22:
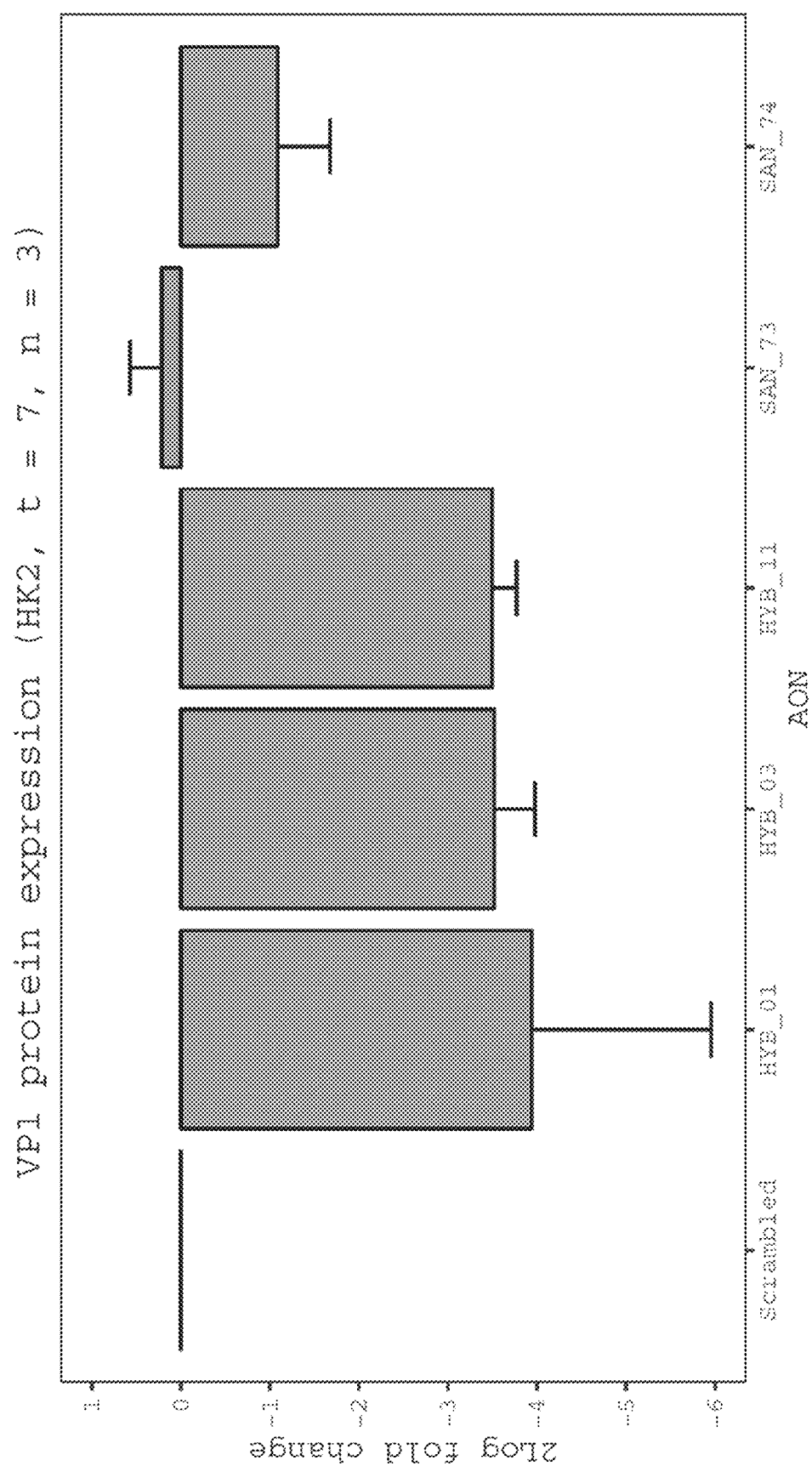
FIG. 22: TAg splice-modulating lead AONs reduce expression levels of VP1 protein in BKV-infected human kidney epithelial cells. Reduction in VP1 protein levels in scramble AON-treated HK2 cells versus HK2 cells treated with BKV-targeting lead AONs (HYB_01, HYB_03 or HYB_11), after which cells were infected with BKV at a multiplicity of infection of ~100. Note: SAN_73 and SAN_74 are previously described AONs (16 nucleotides in length). These data are representative of a biological n=3.

Interestingly, VP1 mRNA expression levels were reduced by most of the BKV-targeting AONs, with the exception of HYB_04, HYB_12, HYB_13 and HYB_14 (FIGS. 13 and 20). Similar to our results obtained for TAg mRNA, HYB_01, HYB_03 and HYB_11 in particular resulted in striking reductions in VP1 RNA expression in HK2 cells (FIG. 13). Moreover, HYB_01 efficiently reduced VP1 mRNA levels regardless of whether the AON was administered prior to infection or post-infection with BK virus in HK2 cells (FIG. 26, left and right panels). Importantly, the observed reductions in VP1 mRNA resulted in dramatic attenuation of VP1 protein levels in HK2 cells (FIGS. 14-15 and 21-22). In keeping with our observations for TAg mRNA levels, SAN_73 and SAN_74 did not significantly impact expression levels of VP1 mRNA and protein.

Figure 29:
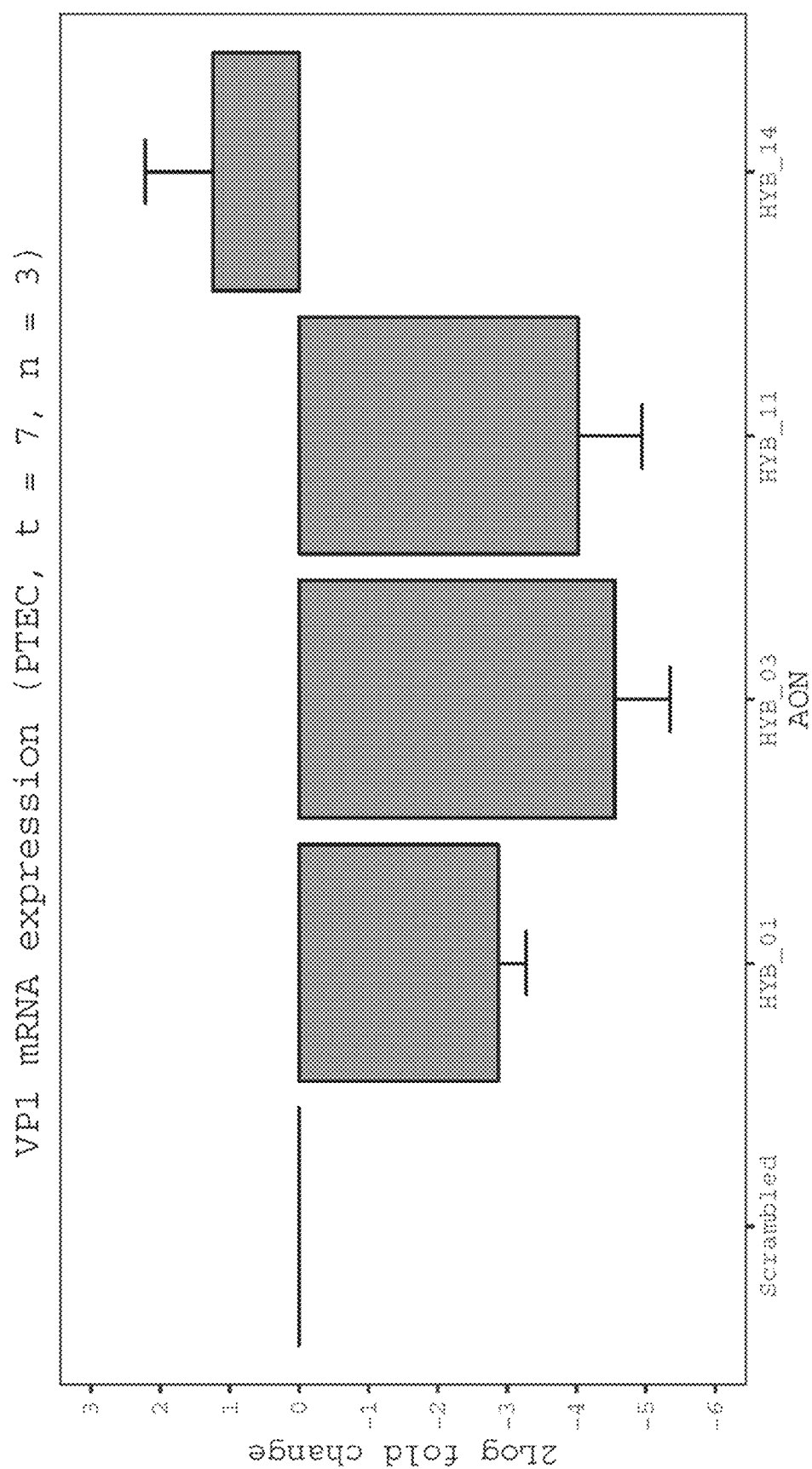
FIG. 29: TAg splice-modulating lead AONs reduce expression levels of VP1 mRNAs in BKV-infected hPTECs. Reduction in VP1 RNA levels in scramble AON-treated hPTECs versus hPTECs treated with BKV-targeting lead AONs (HYB_01, HYB_03 or HYB_11) or HYB_14, after which cells were infected with BKV at a multiplicity of infection of ~100 (n=3 biological replicates). These data are representative of a biological n=3.
Figure 30:
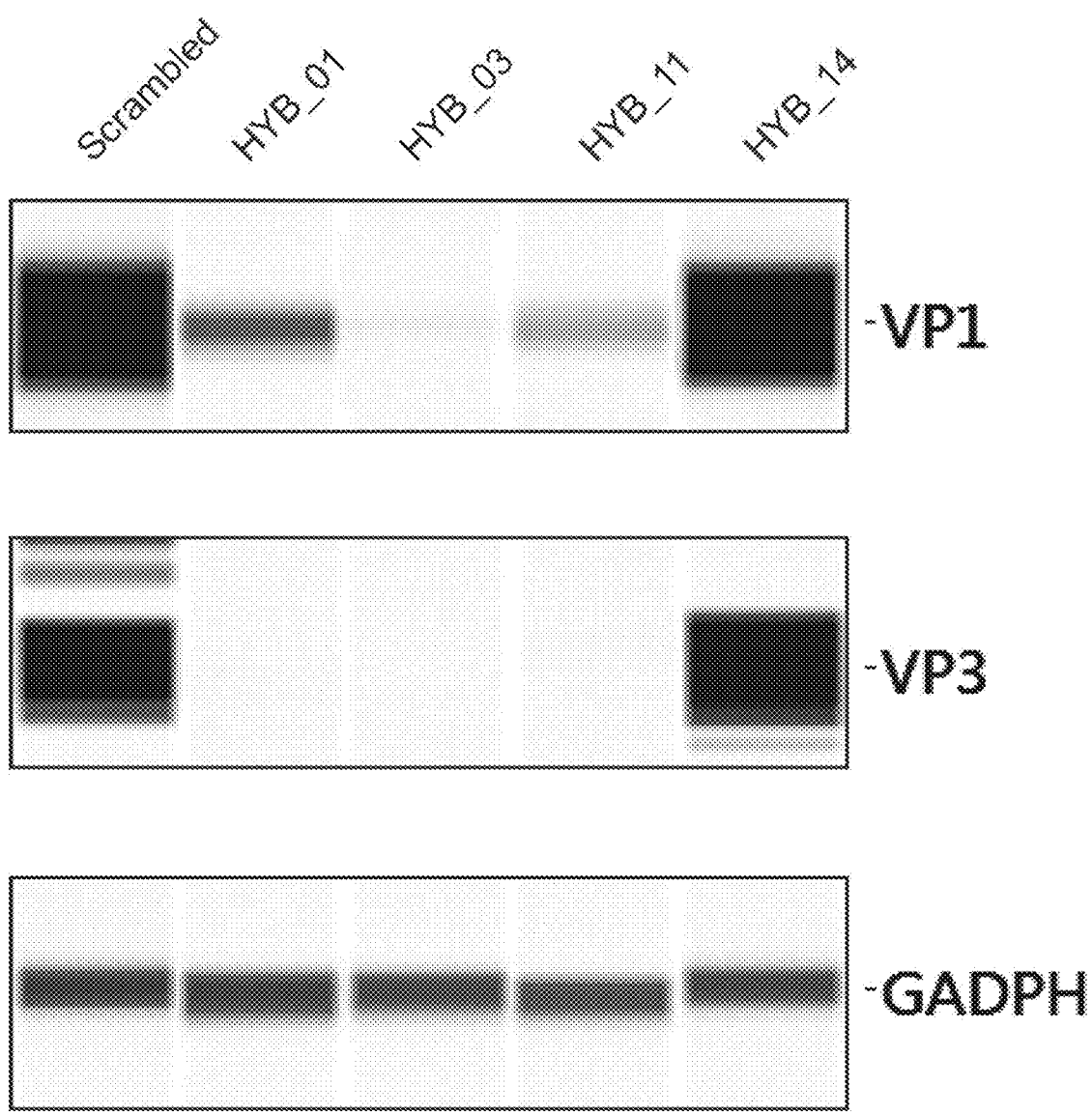
FIG. 30: TAg splice-modulating lead AONs reduce VP1 and VP3 protein expression levels in BKV-infected hPTECs. Representative Western blot visualization of VP1 and VP3 protein levels in cellular lysates harvested from hPTECs treated with BKV-targeting lead compound AONs and 7 days post-infection with BK polyomavirus at a multiplicity of infection of ~100 (VP1 and GAPDH: n=3 biological replicates, VP3: n=1).
Figure 31:
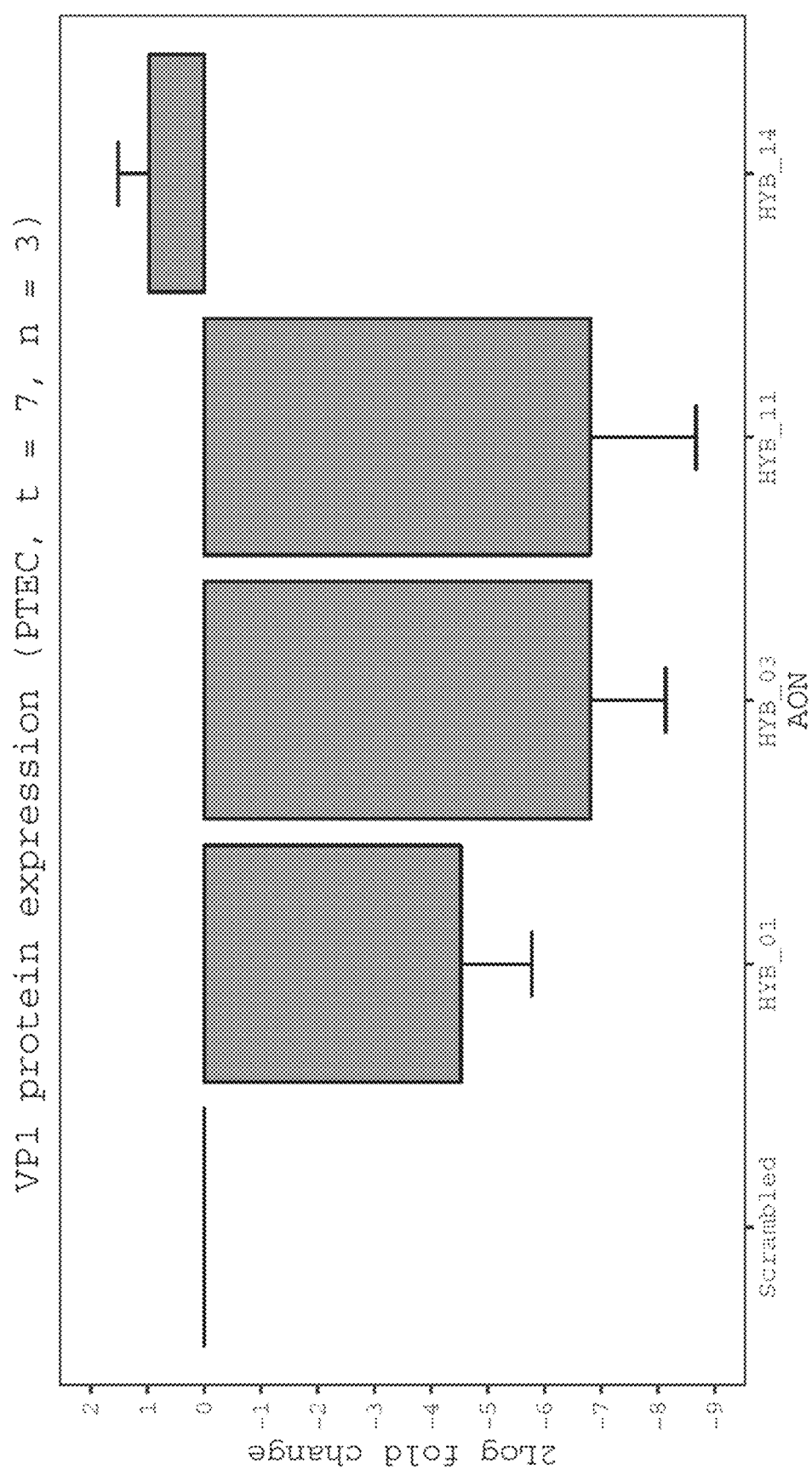
FIG. 31: TAg splice-modulating lead AONs reduce expression levels of VP1 proteins in BKV-infected hPTECs. Reduction in VP1 protein levels in scramble AON-treated hPTECs versus hPTECs treated with BKV-targeting lead AONs (HYB_01, HYB_03 or HYB_11) or HYB_14, after which cells were infected with BKV at a multiplicity of infection of ~100 (n=3 biological replicates). These data are representative of a biological n=3.
Figure 32:
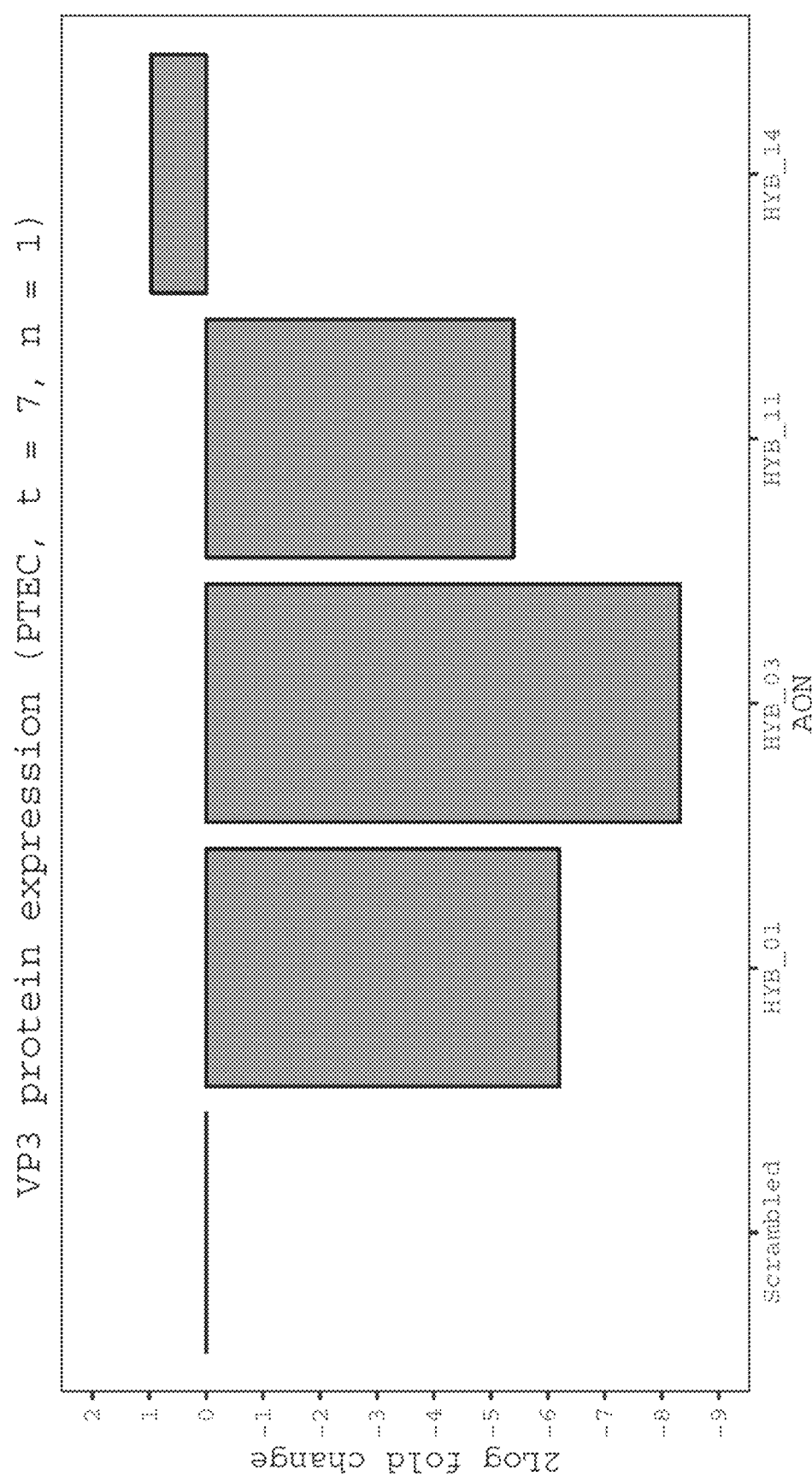
FIG. 32: TAg splice-modulating lead AONs reduce expression levels of VP3 proteins in BKV-infected hPTECs. Reduction in VP3 protein levels in scramble AON-treated hPTECs versus hPTECs treated with BKV-targeting lead AONs (HYB_01, HYB_03 or HYB_11) or HYB_14, after which cells were infected with BKV at a multiplicity of infection of ~100 (n=3 biological replicates). These data are representative of a biological n=1.

As shown in FIGS. 29-31, HYB_01, HYB_03 and HYB_11 all dramatically reduced expression of VP1 mRNA and protein in hPTECs (n=3 biological replicates). Furthermore, HYB_14 did not affect VP1 mRNA and protein levels. Moreover, we have also gained preliminary evidence that our AONs also effectively reduce VP3 protein levels (FIGS. 30 and 32).

Infection and Re-Infection of Human Proximal Tubule Epithelial Cells

Figure 17:
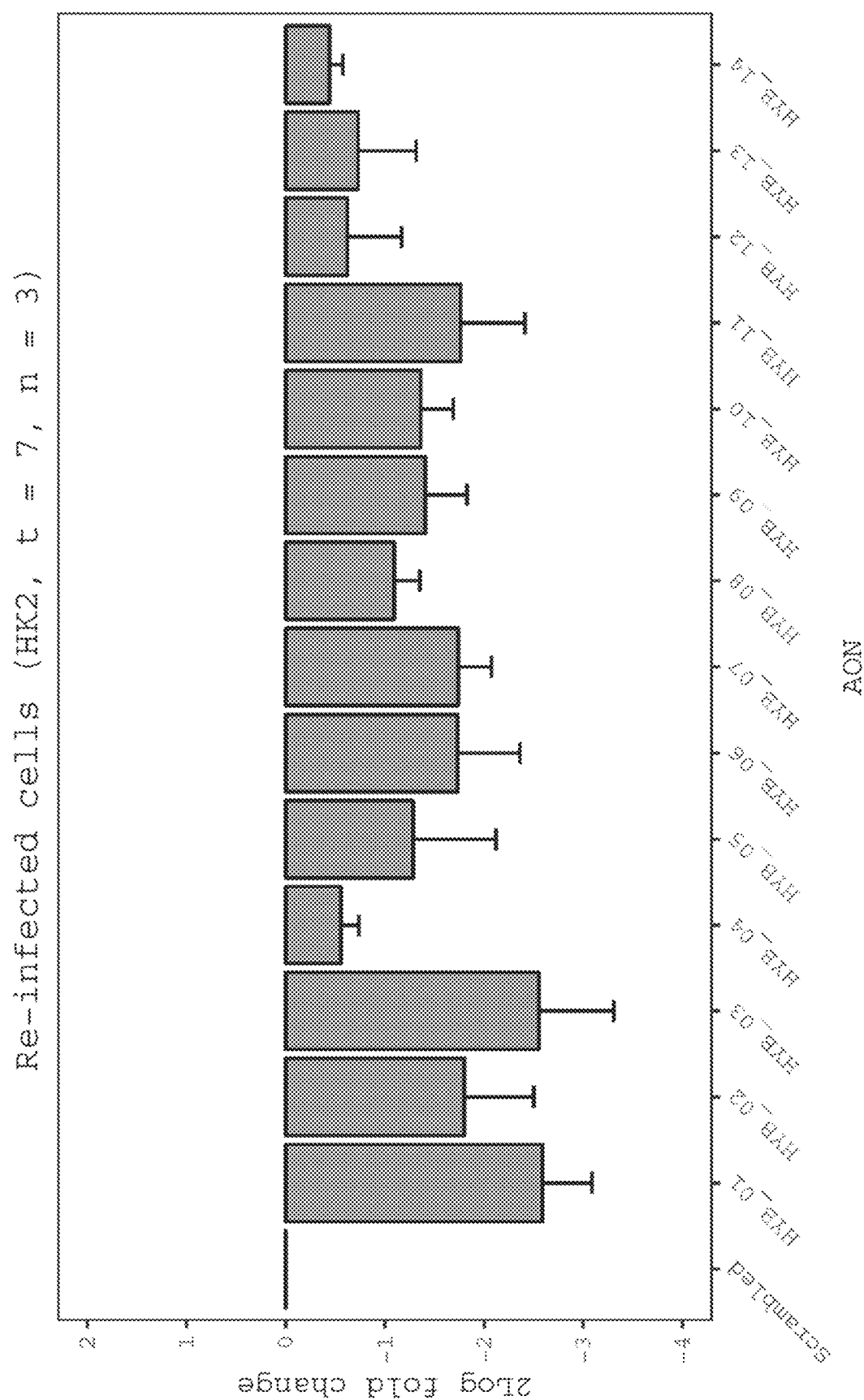
FIG. 17: TAg splice-modulating AONs reduce levels of HK2 re-infection. Culture supernatant was removed at 7 days from HK2 cells that had been pre-treated with BKV-targeting AONs and infected with BKV. The supernatant was used to infect untreated HK2 cells (2 h) after which the cells were cultured for 7 days and stained immunohistochemically for TAg and hoechst (for nuclei). Subsequently, the percent positive cells were determined and depicted relative to scramble AON-treated cells. Data are representative of biological n=3.
Figure 24:
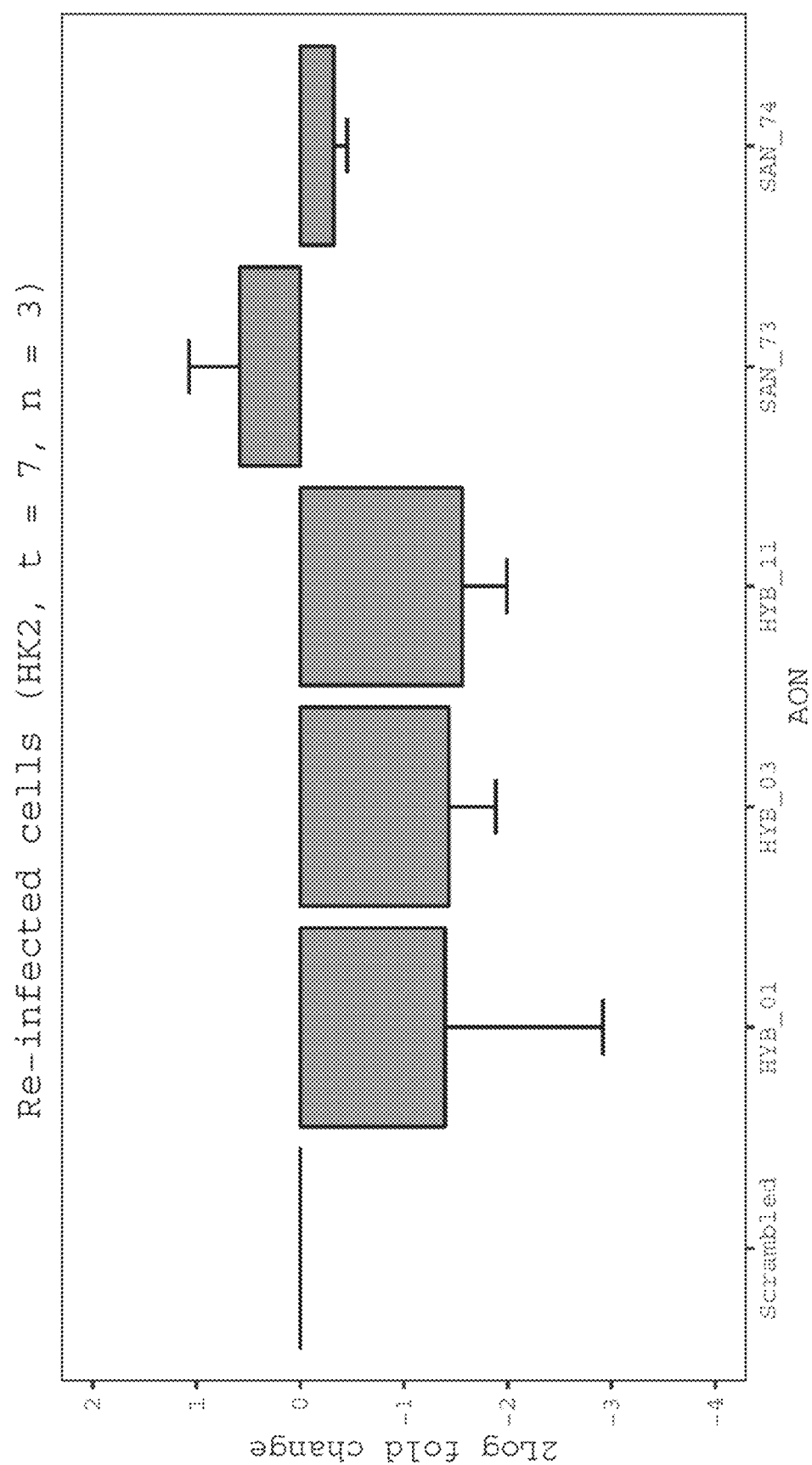
FIG. 24: TAg splice-modulating lead AONs reduce levels of HK2 re-infection. Culture supernatant was removed at 7 days from HK2 cells that had been pre-treated with BKV-targeting lead AONs (HYB_01, HYB_03 or HYB_11) and infected with BKV. The supernatant was used to infect untreated HK2 cells (2 h) after which the cells were cultured for 7 days and stained immunohistochemically for TAg and Hoechst (for nuclei). Subsequently, the percent positive cells were determined and depicted relative to scramble AON-treated cells. Data are representative of biological n=3.

We next assessed whether our broad assortment of BKV-targeting AONs could impact the degree of infection and re-infection by BKV in HK2 cells. To achieve this, we first treated HK2 cells with BKV-targeting AONs and infected the cells with BKV. After 7 days, we harvested the viral particle-containing supernatant and used this to infect new batches of untreated HK2 cells. After 7 days, we performed immunofluorescent staining for TAg-infected cells and scored this as a percent positive (by counterstaining with Hoechst for nuclei). As shown in FIGS. 17 and 24, these studies revealed that cells previously treated with our BKV-targeting AONs displayed significantly lower levels of re-infection. In contrast, pre-treatment of HK2 cells with SAN_73 and SAN_74 did not decrease re-infection levels to the degree observed with HYB_01, HYB_03 and HYB_11.

BKV-Targeting AONs Influence Viral Particle Production

Figure 16:
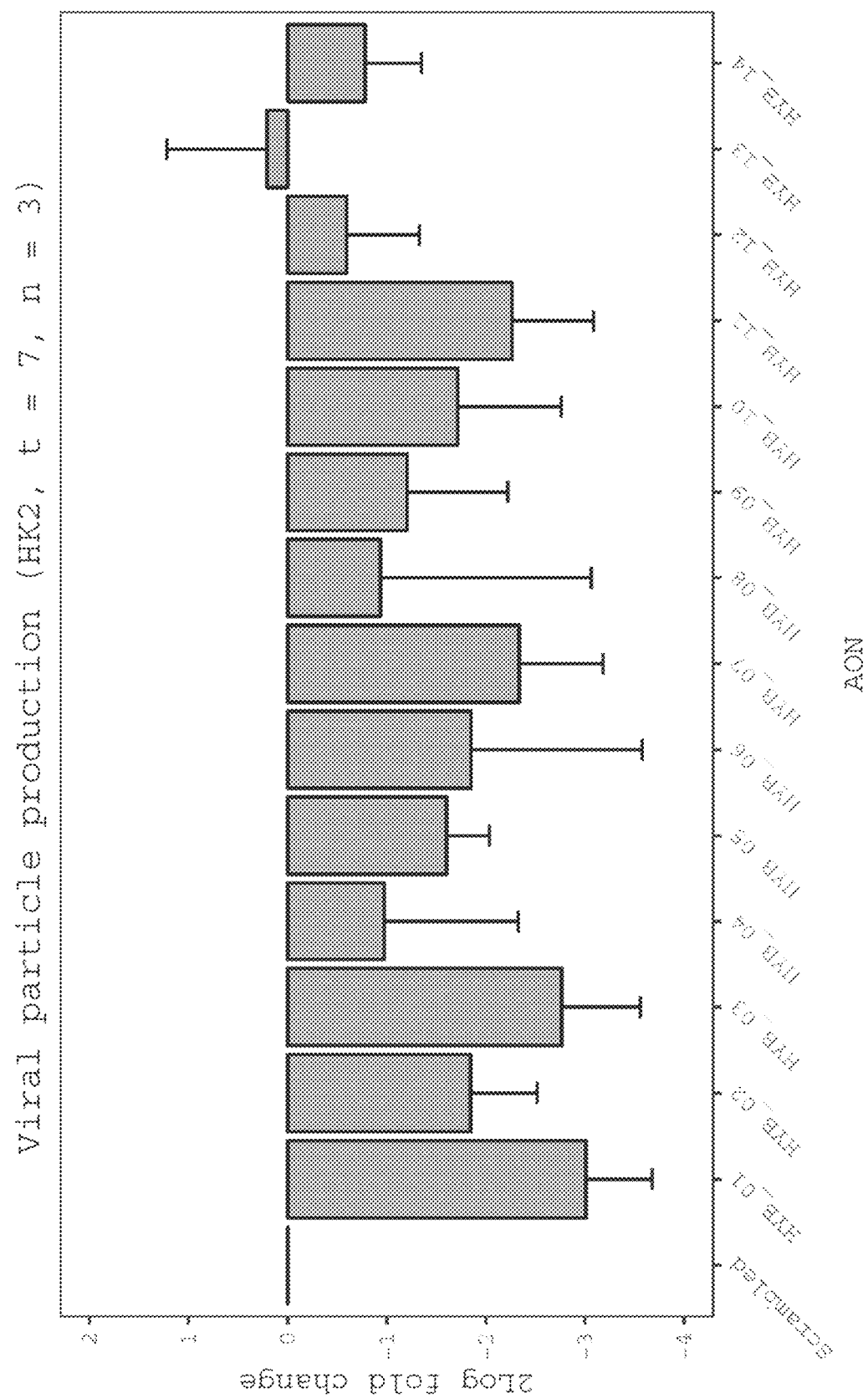
FIG. 16: TAg splice-modulating AONs reduce BKV DNA replication. Viral particle concentrations in the culture supernatant at 7 days post-infection were determined by the PCR analysis method for VP1 in the BKV genome. HK2 cells treated with BKV-targeting AONs consistently reveal reduced levels of BKV particles in the culture supernatant, as compared to those treated with the scrambled AON. Data represent a biological n=3.
Figure 23:
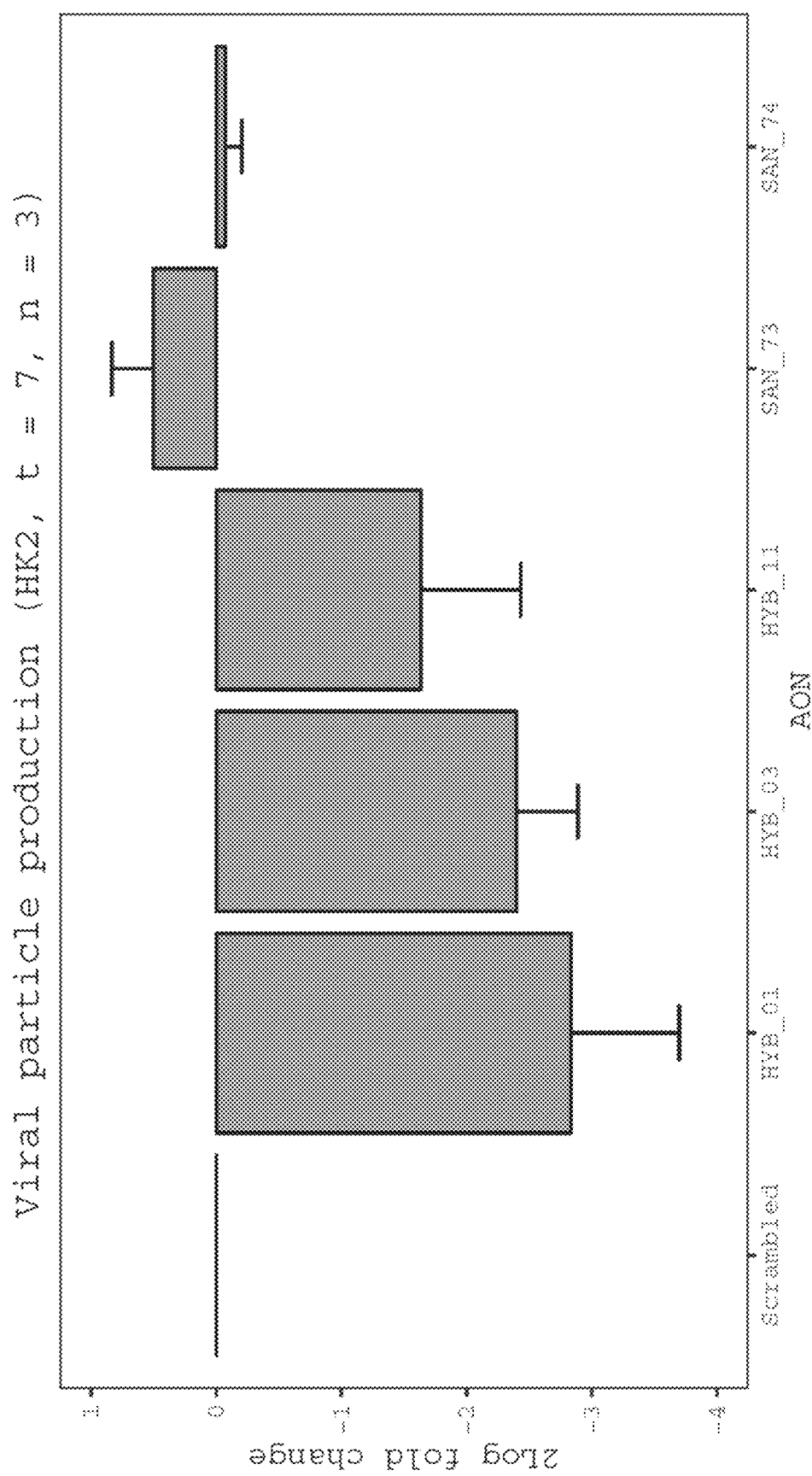
FIG. 23: TAg splice-modulating lead AONs reduce viral particle production in BKV-infected human kidney epithelial cells. Reduction in the levels of viral particles in scramble AON-treated HK2 cells versus HK2 cells treated with BKV-targeting lead AONs (HYB_01, HYB_03 or HYB_11), after which cells were infected with BKV at a multiplicity of infection of ~100. Note: SAN_73 and SAN_74 are previously described AONs (16 nucleotides in length). These data are representative of a biological n=3.
Figure 33:
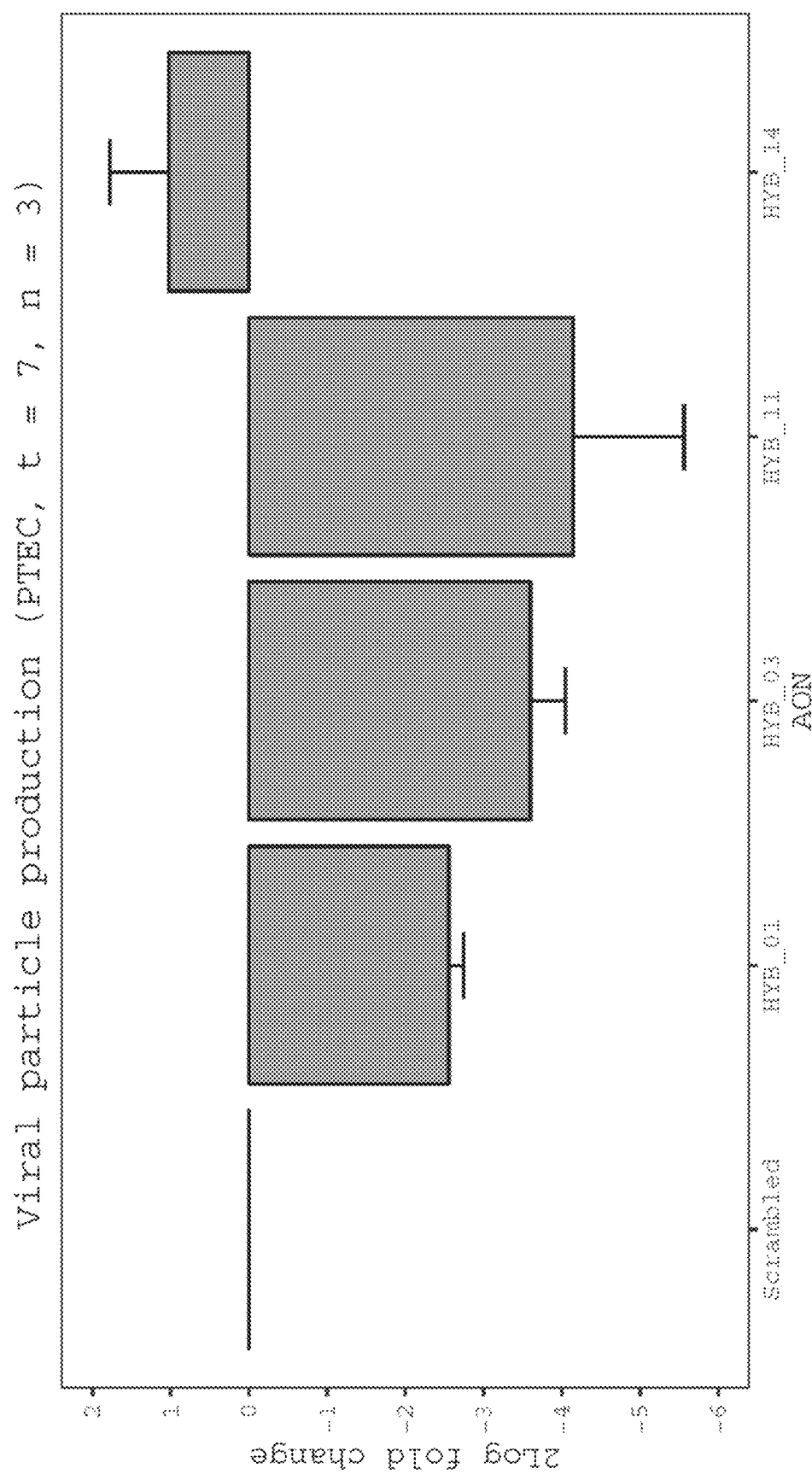
FIG. 33: TAg splice-modulating lead AONs reduce viral particle production in BKV-infected hPTECs. Reduction in the levels of viral particles in scramble AON-treated hPTECs versus hPTECs treated with BKV-targeting lead AONs (HYB_01, HYB_03 or HYB_11) or HYB_14, after which cells were infected with BKV at a multiplicity of infection of ~100. These data are representative of a biological n=3.
Figure 34:
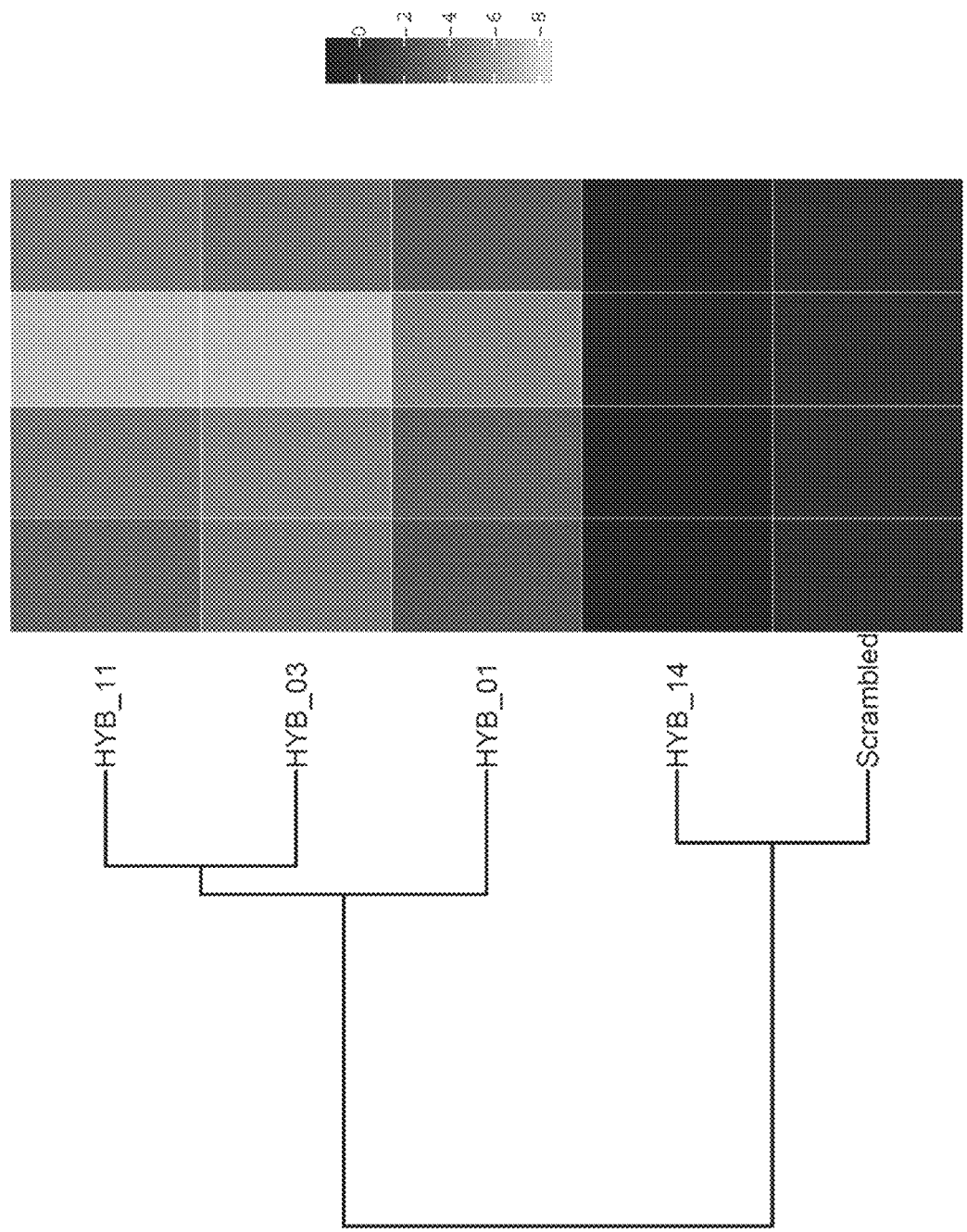
FIG. 34: Heatmap depicting cumulative effects of BKV-targeting lead compound AON treatment on various aspects of BKV infection of hPTECs. Summary of effects observed on TAg and VP1 mRNA, VP1 protein and viral particle production for hPTECs pre-treated with our lead compound AONs (HYB_01, HYB_03 or HYB_11) or HYB_14. Scale indicates that black represents little-to-no effect while white indicates large effect (2 log fold change compared to scrambled, n=3).

The observed reductions in VP1 protein, a protein that is required to package the BK virus DNA, should severely impact the formation and release of new viral particles into the supernatant. Indeed, as shown in FIGS. 16, 23 and 33, the vast majority of our BKV-targeting AONs decrease viral particle production 7 days post-infection, whereby the greatest reductions are yielded by HYB_01, HYB_03 and HYB_11. In contrast, SAN_73 and SAN_74 were found to but slightly decrease viral particle production. This mechanism is likely responsible for decreased (re-)infection of local and distal cells in vitro, and strongly suggests that the uptake of our BKV-targeting AONs in proximal tubule epithelial cells of the kidney post-kidney transplantation would be an effective therapeutic modality in preventing BKV activation and/or spreading.

BKV-Targeting AONs Modulate Splicing of TAg

Figure 42:
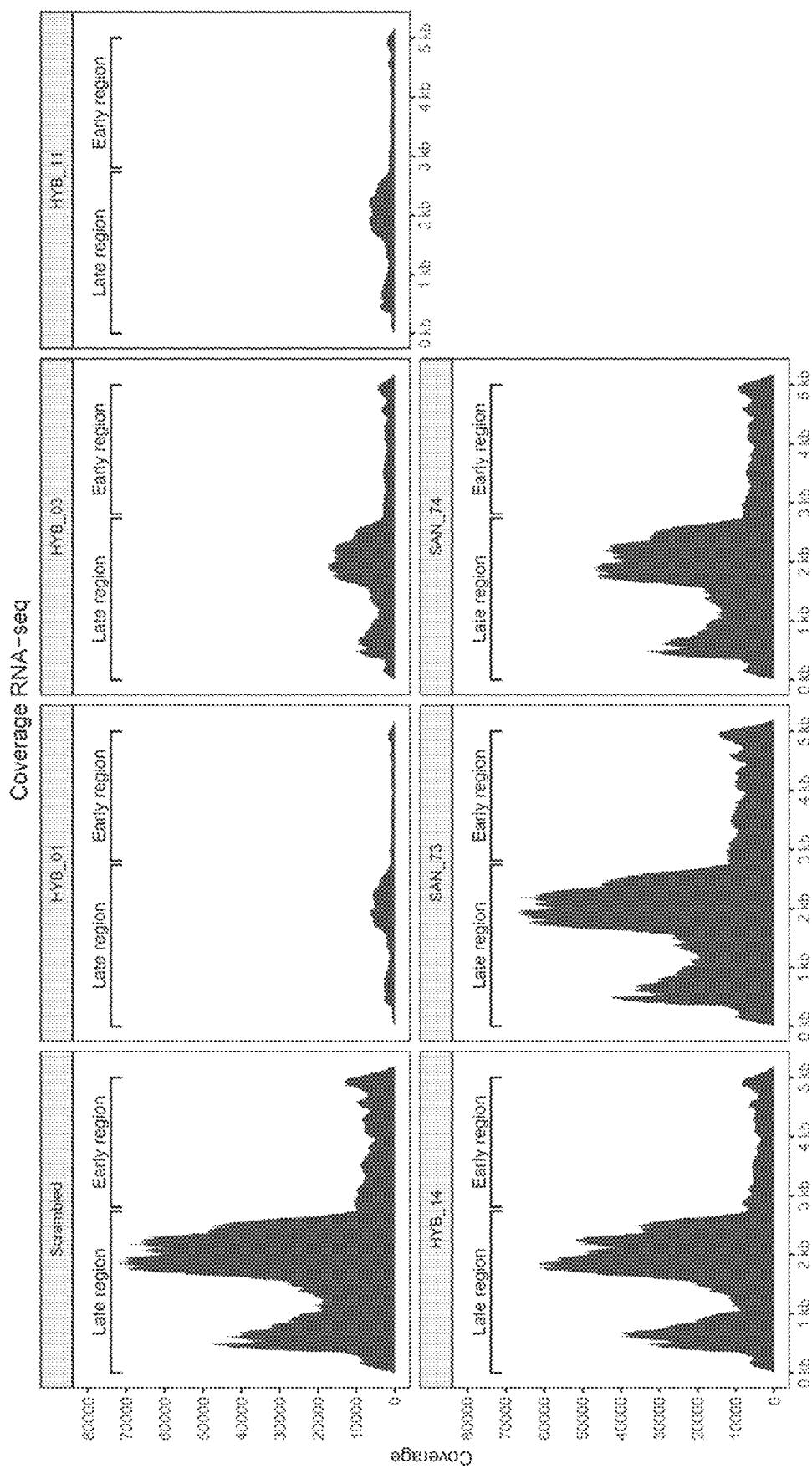
FIG. 42: Coverage of BKV genome by RNAs amplified during RNA-seq. Alignment of paired-end reads to the BKV genome from scrambled control, HYB_01, HYB_03, HYB_11, HYB_14 or SAN_73 and SAN_74 treated cells allows for semi-quantitative assessment of BKV RNA expression levels. Data are indicative of a biological n=3 and have been separated into early and late phase gene expression profiles.

To gain mechanistic insight into how our BKV-targeting AONs are leading to the herein described reductions in TAg and VP1 mRNA, we performed RNA-seq of RNA harvested from HK2 cells that were treated with a scrambled AON, HYB_01, HYB_03, HYB_11, HYB_14, SAN_73 or SAN_74, after which the cells were infected with BKV for 2 hours. Post-washing, the cells were cultured for 7 days after which RNA was harvested, assessed on a bioanalyzer for signs of degradation. Subsequently, equivalent quantities of RNA were ribo-depleted, underwent library preparation after which RNA-seq was performed. In keeping with our aforementioned reductions in TAg and VP1 mRNA in HK2 cells, coverage of the BKV genome from scrambled control, HYB_14 or SAN_73 and SAN_74-treated cells were clearly higher than those treated with BKV-targeting AONs (FIG. 42). For analysis of changes in BKV splicing, both the human genome as well as the BKV genome was provided for alignment of sequences, with Bowtie being used to align the paired-end reads.

Figure 35:
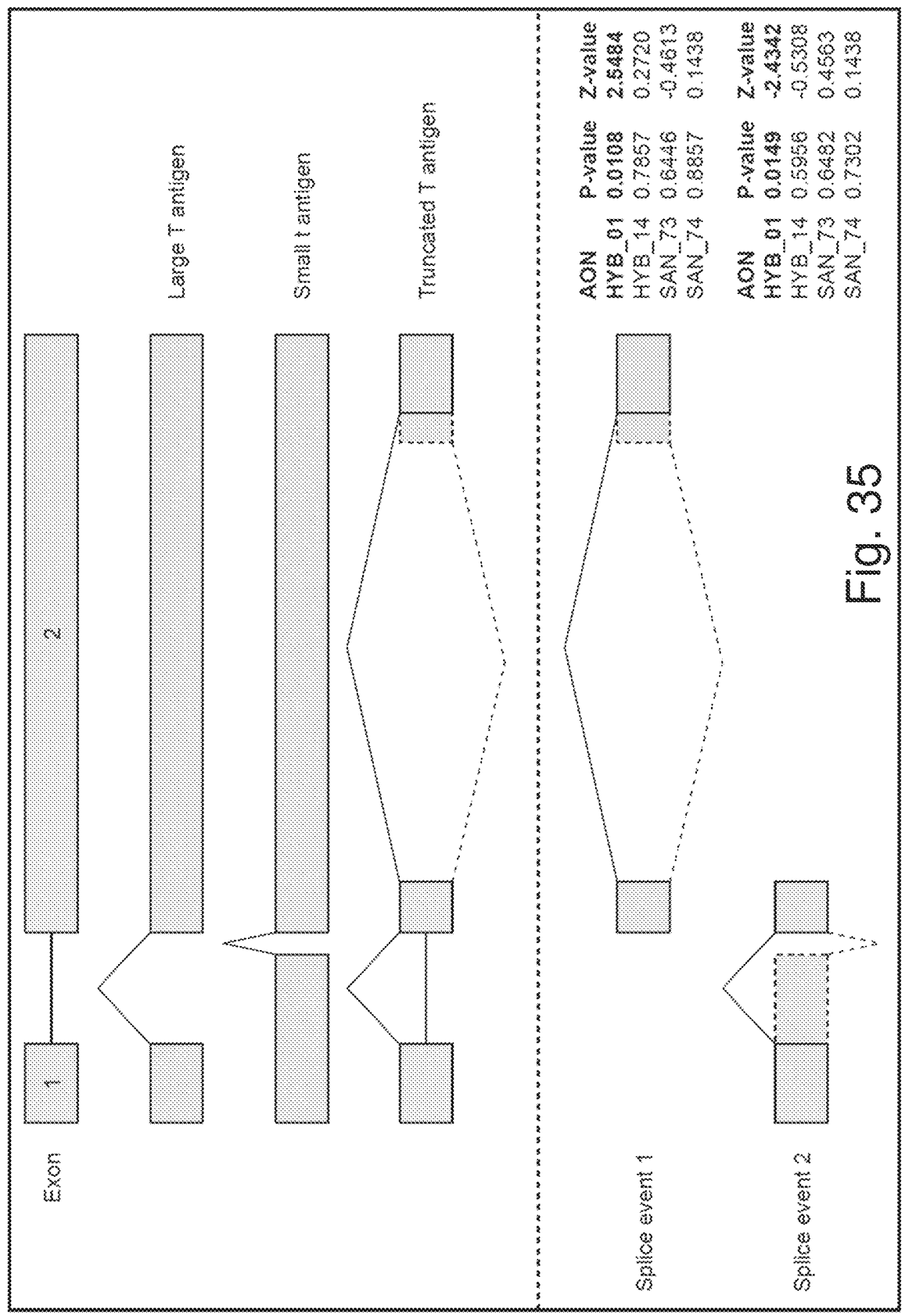
FIG. 35: RNA-seq analysis of modulation of splicing induced by lead BKV-targeting AONs. Primary transcripts and splicing events are depicted in upper portion of panel, while in lower portion of panel the observed splicing patterns and z-scores are presented, indicating that our BKV-targeting AONs indeed modulate splicing. Events are observed at the exon 1—intronic site as well as at the 3'-region of exon 2. Collectively, the presence of a single AON that appears to impact both proximal and distal effects in splicing is indicative of a complex splicing event.

In order to quantify alternative splicing in the samples, EventPointer was applied. A specific GTF file with different transcripts of the virus was used. The algorithm tries to identify possible alternative splicing events and relate each of the transcripts to the possible alternative paths. To assess splicing in a highly complex pre-mRNA such as TAg, the pre-mRNA was dissected into unique splice events, leading the TAg pre-mRNA to initially be separated into 7 fragments. At each junction, defined by the frequency that a splice event was detected, the percent spliced in (PSI) was determined. This resulted in four unique alternative splice events that occurred in all conditions at a high frequency as determined by EventPointer. The frequency of these events was scored using Kallisto software, resulting in a quantification per transcript (with units being transcripts per million). After statistical testing for significance, significant changes in splicing were observed at the exon 1—intron junction of TAg, precisely the site where our AONs are binding and predicted to impact splicing (FIG. 35). Here, the upper panel provides a schematic of the relevant splicing events in the TAg pre-mRNA that can subsequently be dissected into unique splicing events as shown in the bottom panel. For splice event 1, HYB_01 yields a highly significant modulation in the splicing pattern for truncated T antigen (P=0.0108), as an alternative splice acceptor site is preferentially used relative to HK2 cells treated with a scrambled control AON (Z-value=2.5484). Similarly, for splice event 2 a highly significant change in splicing is detected (p=0.0149) where HYB_01 leads to the preferential generation of small t antigen (tAg) as opposed to TAg (Z-value −2.4342). In contrast, no significant splicing changes are detected in cells treated with HYB_14, SAN_73 or SAN_74. The absence of splicing modulation for SAN_74 is in particular striking given that this AON also bridges the exon 1—intron junction. This strongly suggests that the size of our AONs (20 nt as opposed to 16 nt in length) plays a role in determining their capacity to impact splicing of TAg, potentially as a result of steric hinderance.

Furthermore, the data depicted in FIG. 35 also suggest that the modulation of splicing at the exon 1—intronic junction (splice event 2) influences splicing decisions occurring within exon 2 (splice event 1). Hence, our BKV-targeting AONs appear to be triggering a mutually exclusive or complex splicing event downstream in the TAg pre-mRNA. These studies are based on a biological n=3.

Figure 43:
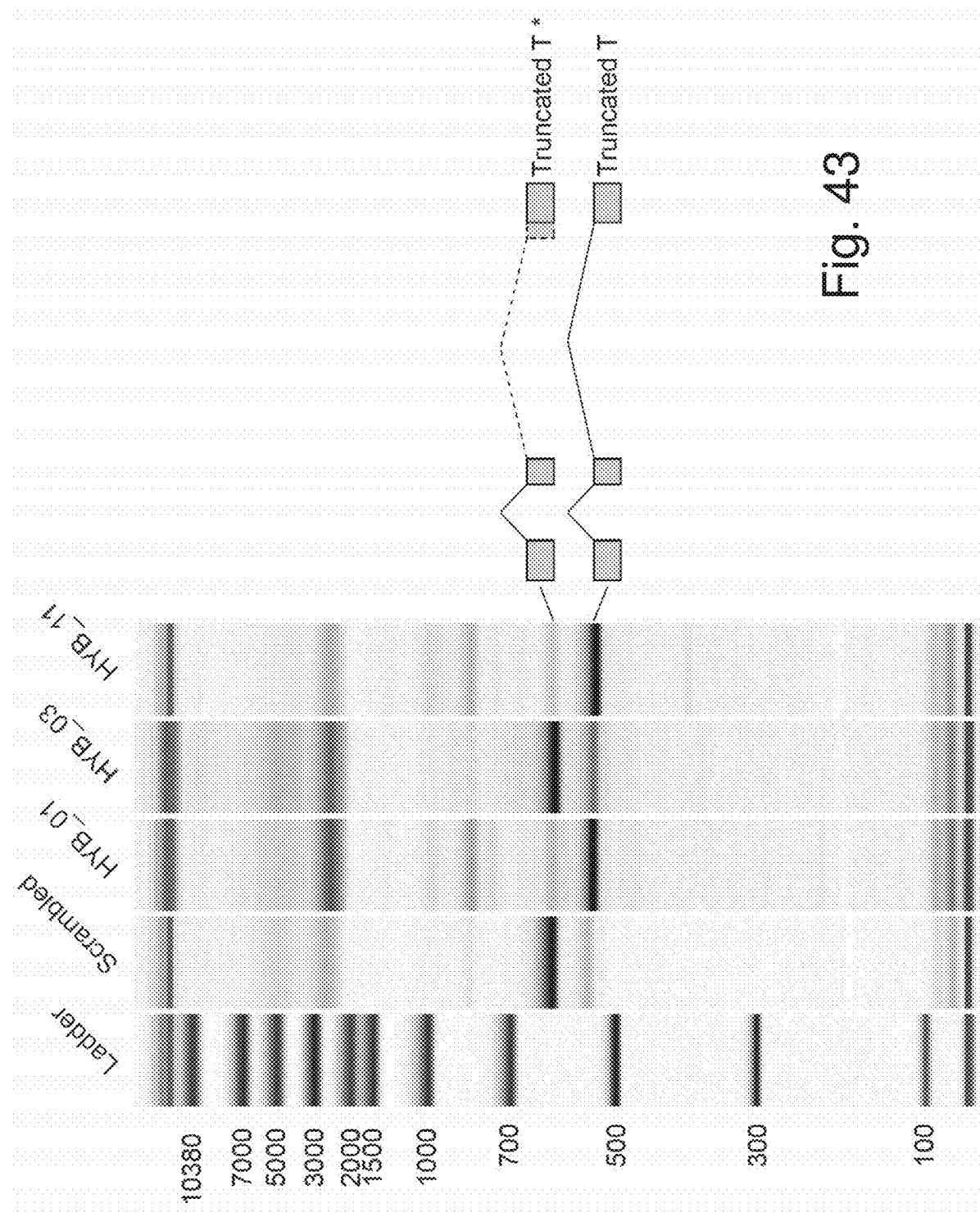
FIG. 43: Electrophoretic analysis of long-read high-fidelity Phusion polymerase generated TAg (pre-)mRNAs. Phusion polymerase was used to generate long-read high fidelity mRNAs from RNA harvested from HK2 cells treated with either scramble control AON (lane 1) or BKV-targeting AONs (namely HYB_01, HYB_03 or HYB_11; lanes 2-4, respectively) and assessed by capillary electrophoresis. Data are representative of a biological n=3.

Supporting evidence that our BKV-targeting AONs mediate changes in TAg splicing were obtained by performing long-range PCR using high-fidelity Phusion polymerase. As shown in FIG. 43, dramatic shifts in truncated T antigen acceptor site usage (splice event 1 in FIG. 35) were observed for HYB_01 and HYB_11 as compared to scramble control-treated cells, with a more subtle shift evident for HYB_03. These data confirm that AONs targeting the exon 1—intron junction profoundly impact splicing decisions within exon 2.

Figure 36:
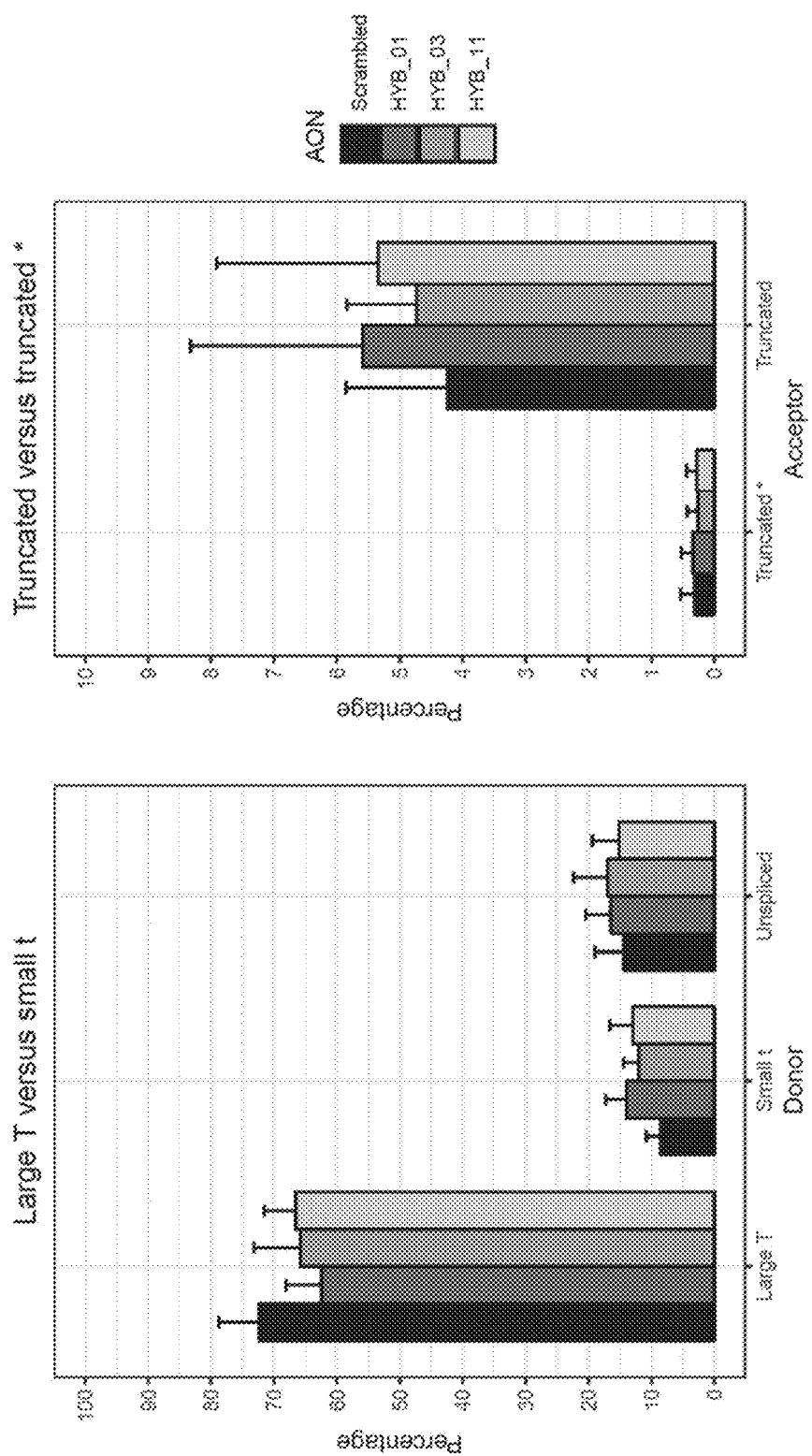
FIG. 36: Long-sequence read analysis of splicing modulation induced by BKV-targeting lead compound AONs. Long-sequence read analysis of RNA transcripts from HK2 cells pre-treated with scrambled AON or our lead compound AONs (HYB_01, HYB_03 or HYB_11). Left: Bar graphs depict the percentage of transcripts utilizing the Large T or small t donor site in combination with a fixed acceptor site (intron—exon 2) or unspliced transcript, indicative of splicing modulation by BKV-targeting AONs. Right: Bar graphs depict the percentage of transcripts utilizing the truncated T or Truncated T * acceptor site in combination with a fixed donor site, indicative of splicing modulation by BKV-targeting AONs.

To gain additional insight into the splice-mediating effects of our AONs on BKV TAg, we also employed PacBio sequencing to generate long-sequence reads of TAg, where primers binding to the 5'- and 3'-ends of TAg were used to amplify full-length TAg pre-mRNAs. These studies would yield precise insight into the exact usage of individual splice sites within TAg, as well as potential mutually exclusive or complex events as indicated in our RNA-seq data. RNA degradation was assessed on a bioanalyzer, and following target enrichment by PCR, the PCR products were size selected. The cDNA library was prepared, ends repaired, adapters ligated, DNA purified and SMRTbell DNA sequenced. Subsequently, the subreads were converted into circular consensus reads (insert sequence reads). As shown in FIG. 36, in keeping with our RNA-seq data, these studies indicate that AONs directed at the TAg exon 1—intron acceptor impacts usage or access to this splice site. Our BKV-targeting AONs, in particular HYB_01, reduces levels of TAg produced (left panel; left bars), leading to a shift towards increased levels of small t antigen and unspliced large T antigen (left panel; middle and right bars, respectively). Furthermore, the data provide further support for AON-mediated modulation of truncated T antigen splicing (right panel).

It is important to note that the herein displayed efficacy of our BKV-targeting AONs in modulating TAg splicing at the exon 1—intron junction could lead to the usage of (alternative) cryptic splice donor sites. The potential use of either an upstream (coding sequence portion of exon 1) or downstream cryptic splice site (intronic portion prior to exon 2) could lead to frameshifted mRNAs that generally lead to the introduction of premature termination codons. It is well established that these aberrant transcripts would rapidly be degraded within the cell by nonsense-mediated decay (Hug, N., et al., *Nucleic Acids Research*, 2016). Importantly, this rapid processing would likely preclude us from detecting the majority of these malformed transcripts.

Nevertheless, our quantitative and qualitative analyses of the remaining TAg transcripts clearly indicates that our BKV-targeting AONs elicit striking reductions in TAg mRNA levels and simultaneously impact the balance of mRNAs formed as a result of pre-mRNA splicing. These data implicate the dual modulation of TAg expression and splicing as a potent means of attenuating BKV particle production and infectibility.

In Vivo Uptake of BKV-Targeting AONs

Figure 44:
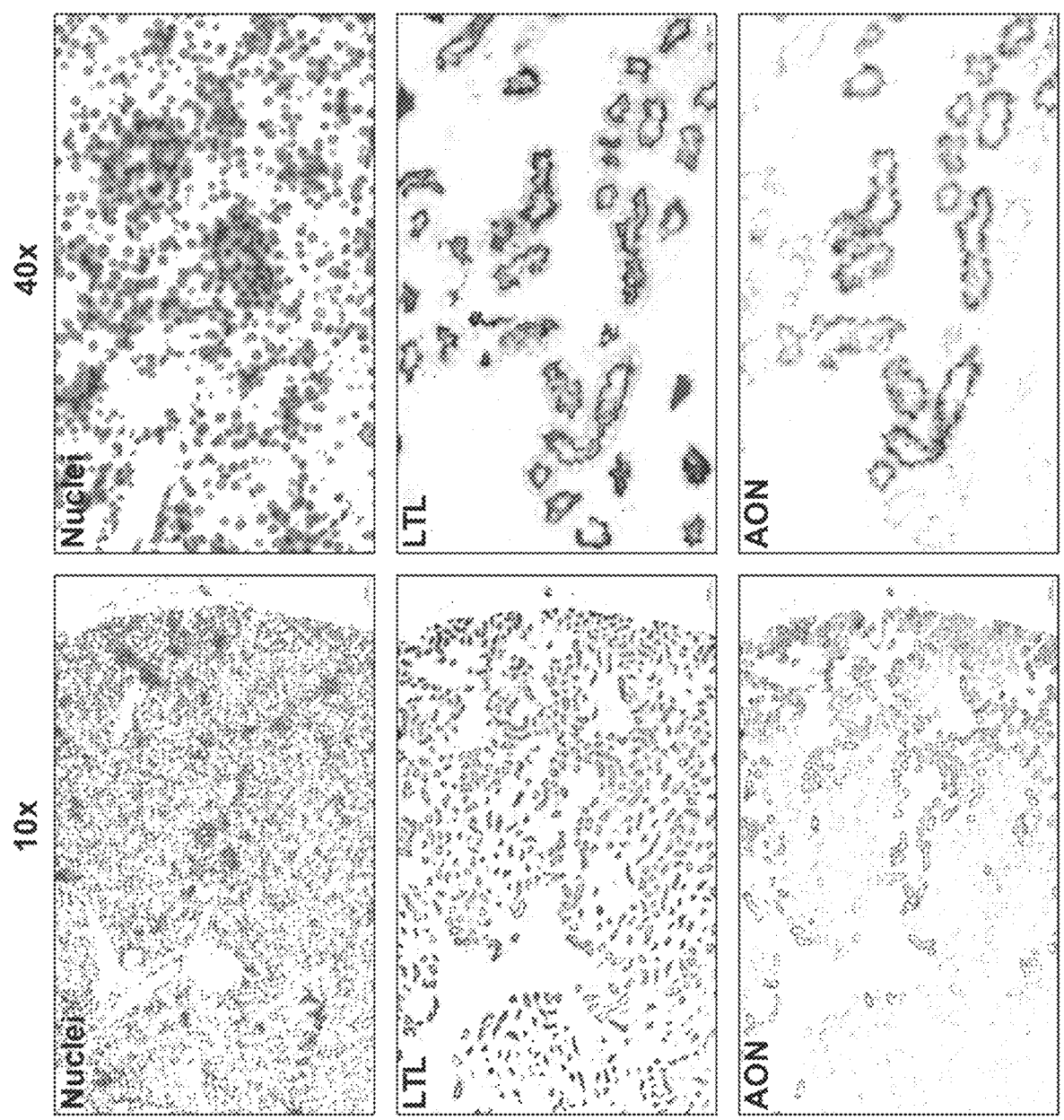
FIG. 44: Fluorescence microscopy of AON uptake in mouse kidneys 24 hours after intravenous administration. Color separated high-magnification images of mouse kidney sections 24 hours after intravenous administration of 40 mg/kg HYB_01 (2'MOE without 5' 6-FAM label) in C57BL/6J mice. Nuclei are stained with Hoechst, proximal tubule epithelial cell uptake is evident based on co-localization with lotus tetragonolobus lectin (LTL)-positive cells of the kidney (proximal tubuli). Left panels represent a 100× magnification (10× objective, scale bar=100 μm) whereas right panels are 400× magnified (40× objective, scale bar=20 μm).
Figure 45:
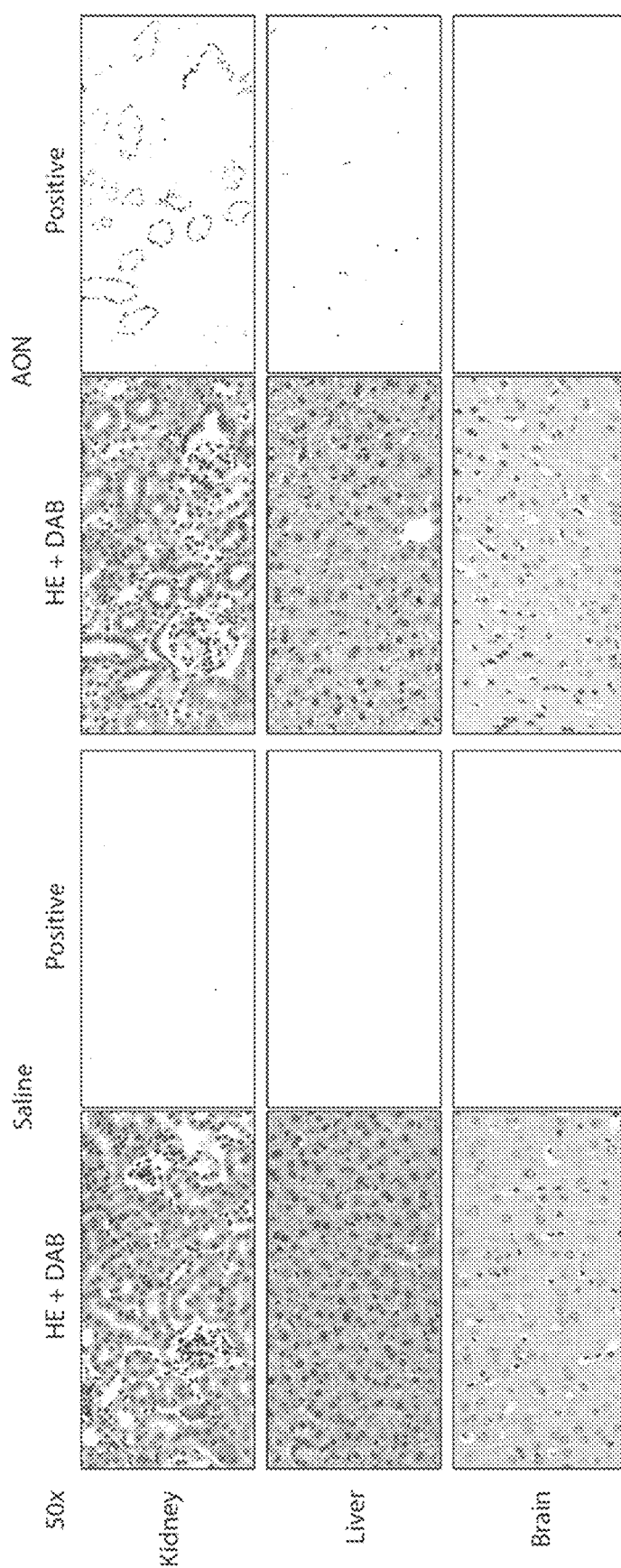
FIG. 45: Immunohistochemical staining of mouse tissues for BKV-targeting AON uptake. Organs were excised 24 h after intravenous administration of 40 mg/kg HYB_01 (2'MOE without 5' 6-FAM label) in C57BL/6J mice and AON uptake assessed immunohistochemically. Hematoxylin and eosin staining (H&E) preceded the specific detection of the AON backbone with anti-phosphorothioate antibody and diaminobenzidine (DAB) as peroxidase substrate to reveal the HRP-labelled secondary antibody. Positive signal for AON staining was visualized by color deconvolution and thresholding in ImageJ, indicating positive tubuli with high levels of AON uptake, with markedly reduced signal in liver and absence thereof in heart tissue.

Our data generated in vitro for BKV-targeting AONs have been chemically modified to contain a 2'-O methyl (2'-OMe) modification of the ribose sugar on each nucleotide within an antisense oligonucleotide. Importantly, the uptake of AONs in vivo has consistently been found to be markedly improved if the 2' hydroxy group is replaced with a 2'-methoxy (2'-MOE) group. Hence, we modified HYB_01, our lead compound to possess both the complete phosphorothioate backbone and 2'-MOE groups, and injected this AON intravenously via the tail vein into C57BL/6J mice. At 24 hours post-injection the mice were sacrificed and the kidney, liver, spleen, brain and muscle harvested and sectioned. As shown in the immunohistochemical staining in FIG. 44 and FIG. 45, HYB_01 displayed excellent uptake in the kidney cortex, and in particular in the proximal tubule epithelial cells of the kidney (as evidenced by uptake in lotus tetragonolobus lectin (LTL)-positive cells of the kidney). Moreover, HYB_01 was also detectable in Kupffer cells of the liver, and undetectable in the brain (see FIG. 45). Furthermore, the AONs were detectable in the white pulp of the spleen, minimally detectable in the heart and undetectable in muscle (data not shown).

TAg Splice-Targeting AONs for Other Polyomaviruses

Figure 38:
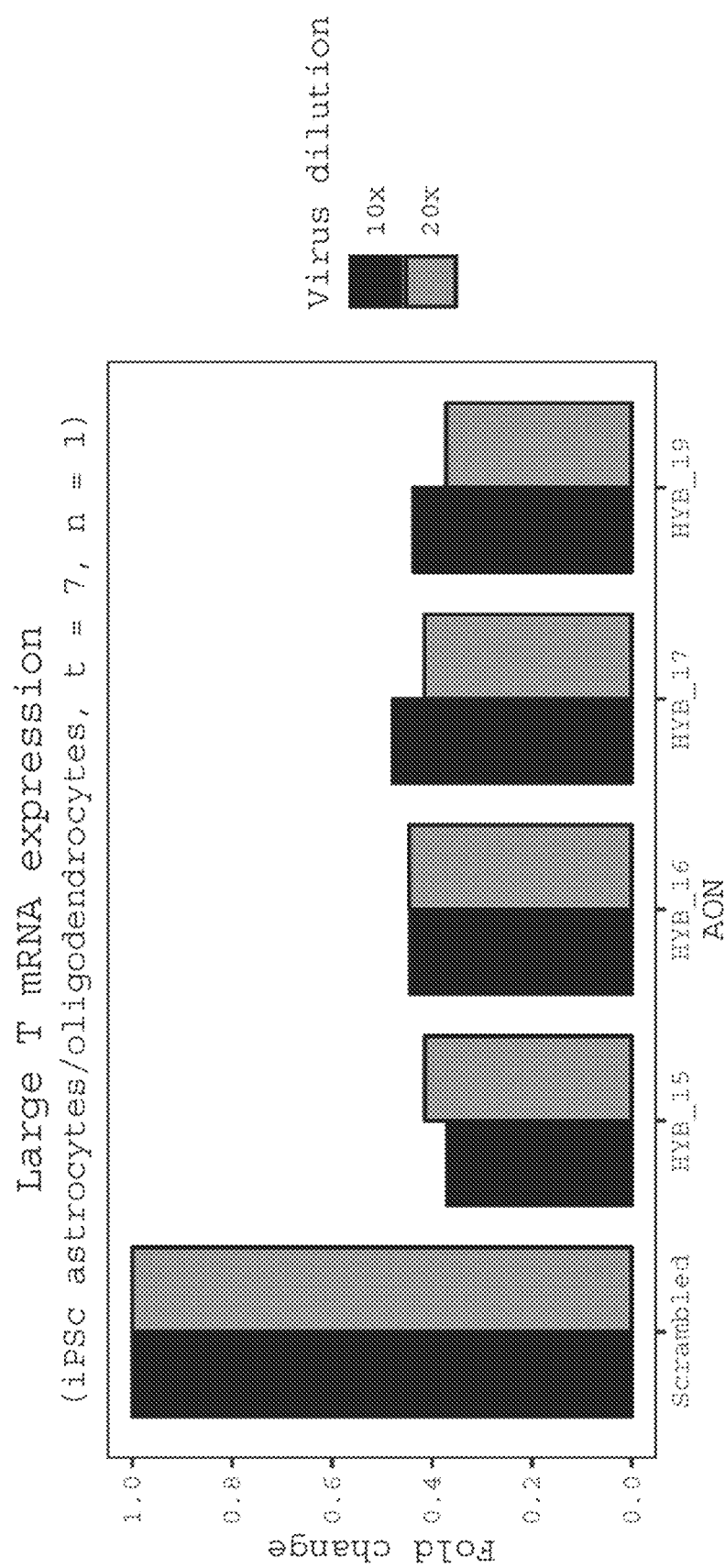
FIG. 38: TAg splice-modulating AONs reduce expression levels of TAg mRNAs in JCV-infected astrocytes derived human induced pluripotent stem cells. Reduction in TAg mRNA levels in scramble AON-treated hiPSC-derived astrocytes versus hiPSC-derived astrocytes treated with JCV-targeting AONs, after which cells were infected with JCV (n=1).
Figure 39:
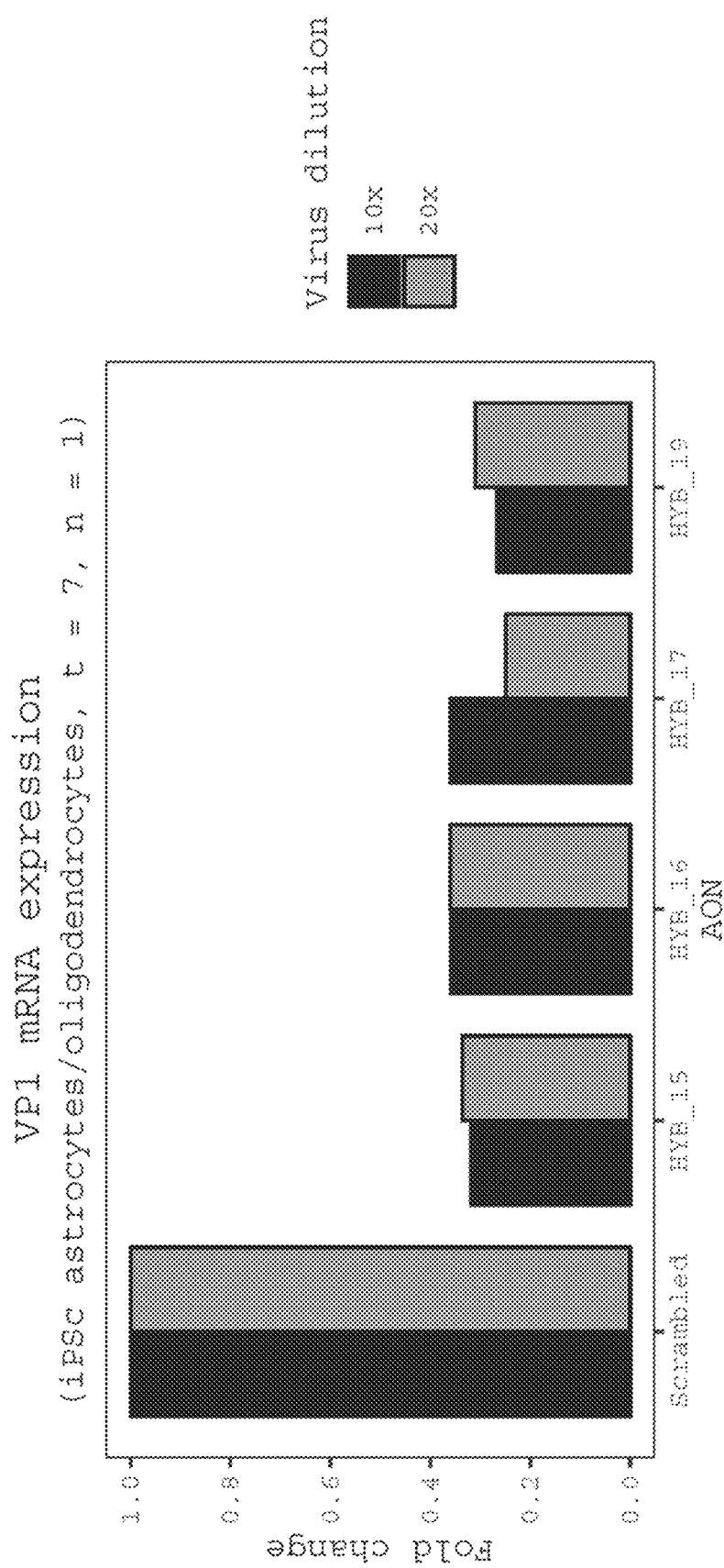
FIG. 39: TAg splice-modulating AONs reduce expression levels of VP1 mRNAs in JCV-infected astrocytes derived human induced pluripotent stem cells. Reduction in VP1 mRNA levels in scramble AON-treated hiPSC-derived astrocytes versus hiPSC-derived astrocytes treated with JCV-targeting AONs, after which cells were infected with JCV (n=1).
Figure 40:
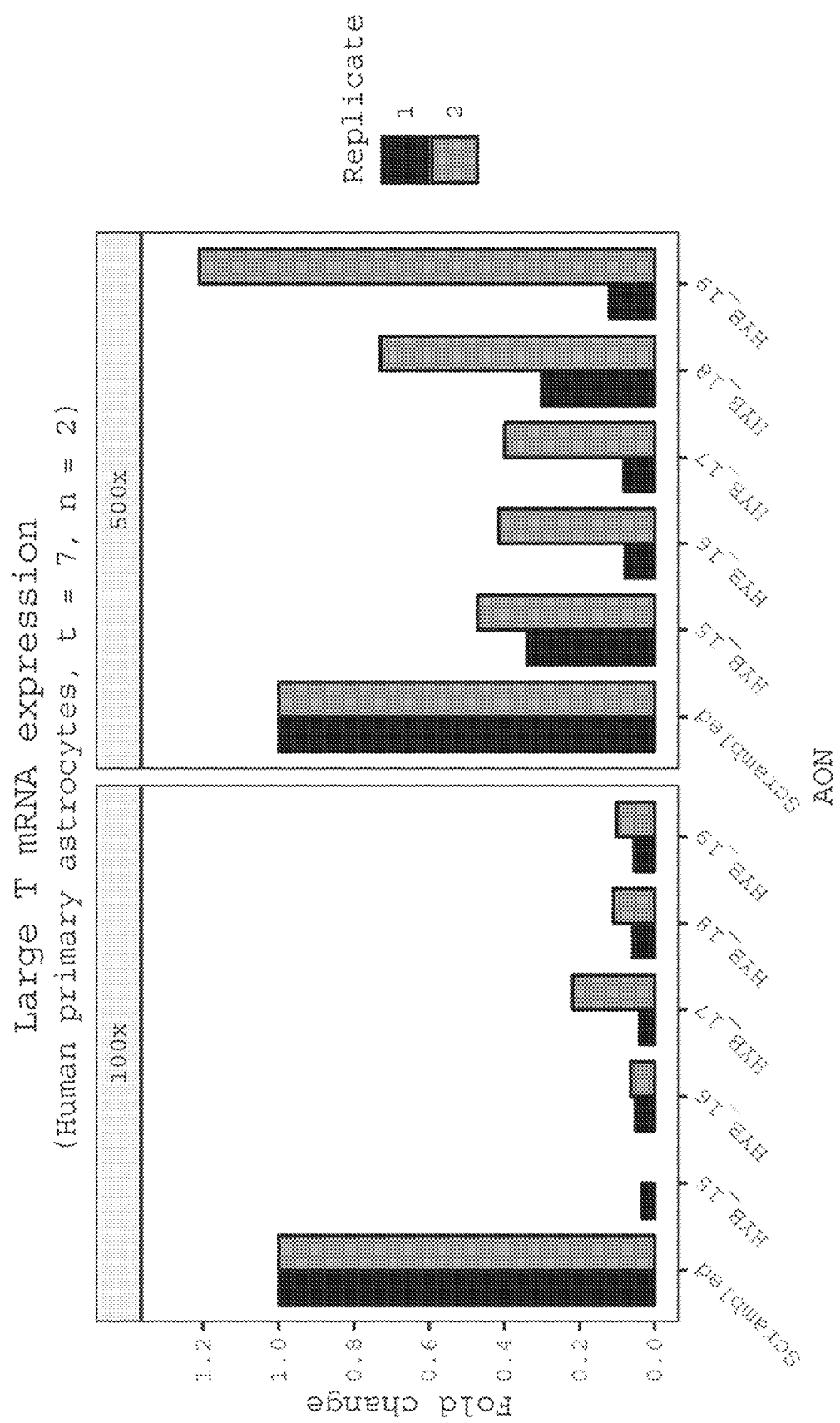
FIG. 40: TAg splice-modulating AONs reduce expression levels of TAg mRNAs in JCV-infected primary human astrocytes. Reduction in TAg mRNA levels in scramble AON-treated primary astrocytes versus primary astrocytes treated with JCV-targeting AONs, after which cells were infected with JCV (n=2 biological replicates).
Figure 41:
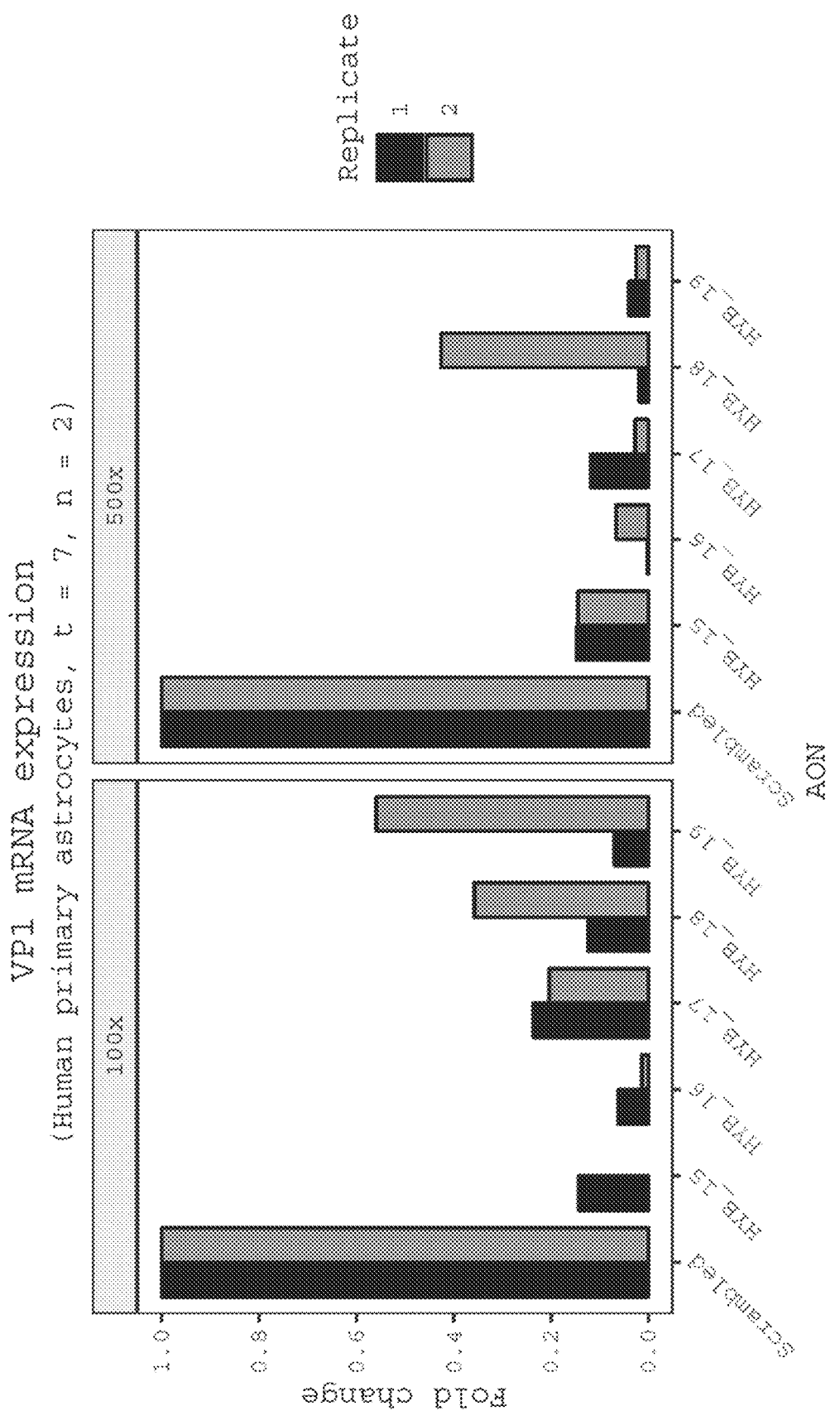
FIG. 41: TAg splice-modulating AONs reduce expression levels of VP1 mRNAs in JCV-infected primary human astrocytes. Reduction in VP1 mRNA levels in scramble AON-treated primary astrocytes versus those treated with JCV-targeting AONs, after which cells were infected with JCV (n=2 biological replicates).

Albeit that JC virus (JCV) is well established to infect the proximal tubule epithelial cells of human kidneys, our repeated attempts to achieve this were unsuccessful. Therefore, we elected to infect other human cells that are known to be susceptible to JC virus and play a role in the development of JCV-related pathophysiologies, namely astrocytes. For these studies, we pre-treated either human induced pluripotent stem cell-derived astrocytes or a human primary astrocytic cell line with one of our 5 JCV-targeting AONs (FIG. 37), namely HYB_15-19 (for 4 hours at a concentration of 50 nM per AON), and subsequently infected the cells with JCV overnight with a titer of $10^{4.5}$ $TCID_{50}/0.2$ mL (information provided by supplier based on infection of Cos-7 cells at 7 days post-infection). As shown in FIGS. 38 and 39, in keeping with our observation that targeting the exon 1—intron junction of BKV TAg diminished TAg and VP1 mRNA expression levels, HYB_15, HYB_16 and HYB_17 resulted in marked reductions in both JCV TAg and VP1 mRNA expression levels in iPS cell-derived astrocytes (n=1). Furthermore, in primary human astrocytes we also observed striking reductions in JCV TAg and VP1 mRNA expression levels at varying titers of JCV administration (FIGS. 40 and 41; n=2).

TABLE

| | Human genus | Virus name | NCBI ref seq | Clinical correlate (if any) |
|---|---|---|---|---|
| Polyomavirus | | | | |
| 1 | Beta | BK polyomavirus | NC_001538 | Py-assoc. nephropathy; haemorrhagic cystitis |
| 2 | Beta | JC polyomavirus | NC_001699 | Progressive multifocal leukoencephalopathy |
| 3 | Beta | KI polyomavirus | NC_009238 | — |
| 4 | Beta | WU polyomavirus | NC_009539 | — |
| 5 | Alpha | Merkel cell polyomavirus | NC_010277 | Merkel cell cancer |
| 6 | Delta | Human polyomavirus 6 | NC_014406 | HPyV6 assoc. pruritic and dyskeratotic dermatosis |
| 7 | Delta | Human polyomavirus 7 | NC_014407 | HPyV7-related epithelial hyperplasia |
| 8 | Alpha | Trichodysplasia spinulosa polyomavirus | NC_014361 | Trichodysplasia spinulosa |
| 9 | Alpha | Human polyomavirus 9 | NC_015150 | |
| 10 | Delta | MW polyomavirus | NC_018102 | |
| 11 | Delta | STL polyomavirus | NC_020106 | |
| 12 | Alpha | Human polyomavirus 12 | NC_020890 | |
| 13 | Alpha | New Jersey polyomavirus | NC_024118 | |

*source Wikipedia.

The invention claimed is:

1. A method of preparing a graft for transplantation, the method comprising providing donor cells with a single stranded RNA antisense oligonucleotide 20 nucleobases in length comprising a sequence that is a reverse complement of 20 nucleobases of a large T antigen pre-mRNA of a BK polyomavirus, wherein the antisense oligonucleotide can modulate splicing of said large T-antigen pre-mRNA in a cell, wherein the antisense oligonucleotide comprises at least 19 contiguous nucleobases of SEQ ID NO: 23 or SEQ ID NO: 24.

2. A method of treatment of a BK polyomavirus infection in a subject, the method comprising administering a single stranded RNA antisense oligonucleotide 20 nucleobases in length comprising a sequence that is a reverse complement of 20 nucleobases of a large T-antigen pre-mRNA of said BK polyomavirus to the subject, wherein the antisense oligonucleotide can modulate splicing of said large T-antigen pre-mRNA in a cell of the subject, wherein the antisense oligonucleotide comprises at least 19 contiguous nucleobases of SEQ ID NO: 23 or SEQ ID NO: 24.

3. The method of claim 2, wherein said subject is an immune-compromised individual.

4. The method of claim 2, wherein the subject is the recipient of a kidney or kidney cell transplant.

5. The method of claim 1, wherein said antisense oligonucleotide comprises a sequence of no more than 19 contiguous nucleobases of SEQ ID NO: 23 or SEQ ID NO: 24.

6. The method of claim 2, wherein said antisense oligonucleotide comprises a sequence of no more than 19 contiguous nucleobases of SEQ ID NO: 23 or SEQ ID NO: 24.

7. The method of claim 5, wherein the 19 contiguous nucleobases of SEQ ID NO: 23 are nucleobases 1 to 19 of SEQ ID NO: 23, and wherein the 19 contiguous nucleobases of SEQ ID NO: 24 are nucleobases 2 to 20 of SEQ ID NO: 24.

8. The method of claim 6, wherein the 19 contiguous nucleobases of SEQ ID NO: 23 are nucleobases 1 to 19 of SEQ ID NO: 23, and wherein the 19 contiguous nucleobases of SEQ ID NO: 24 are nucleobases 2 to 20 of SEQ ID NO: 24.

9. The method of claim 1, wherein said antisense oligonucleotide comprises a phosphorothioate backbone modification and/or a 2'-O-methyl (2'-O-Me) sugar modification.

10. The method of claim 2, wherein said antisense oligonucleotide comprises a phosphorothioate backbone modification and/or a 2'-O-methyl (2'-O-Me) sugar modification.

* * * * *

SEQUENCE LISTING

<160> NUMBER OF SEQ ID NOS: 90

<210> SEQ ID NO 1
<211> LENGTH: 20
<212> TYPE: RNA
<213> ORGANISM: Artificial Sequence
<220> FEATURE:
<223> OTHER INFORMATION: antisense oligonucleotide

<400> SEQUENCE: 1
accucugagc uacuccaggu						20

<210> SEQ ID NO 2
<211> LENGTH: 20
<212> TYPE: RNA
<213> ORGANISM: Artificial Sequence
<220> FEATURE:
<223> OTHER INFORMATION: antisense oligonucleotide

<400> SEQUENCE: 2
acaaaccucu gagcuacucc						20

<210> SEQ ID NO 3
<211> LENGTH: 20
<212> TYPE: RNA
<213> ORGANISM: Artificial Sequence
<220> FEATURE:
<223> OTHER INFORMATION: antisense oligonucleotide

<400> SEQUENCE: 3
cagcacaaac cucugagcua						20

<210> SEQ ID NO 4
<211> LENGTH: 20
<212> TYPE: RNA
<213> ORGANISM: Artificial Sequence
<220> FEATURE:
<223> OTHER INFORMATION: antisense oligonucleotide

<400> SEQUENCE: 4
uccauagguu ggcaccuaga						20

<210> SEQ ID NO 5
<211> LENGTH: 20
<212> TYPE: RNA
<213> ORGANISM: Artificial Sequence
<220> FEATURE:
<223> OTHER INFORMATION: antisense oligonucleotide

<400> SEQUENCE: 5
uguuccauag guuggcaccu						20

<210> SEQ ID NO 6
<211> LENGTH: 20
<212> TYPE: RNA
<213> ORGANISM: Artificial Sequence
<220> FEATURE:
<223> OTHER INFORMATION: antisense oligonucleotide

<400> SEQUENCE: 6
accucugaac uauuccaugu						20

<210> SEQ ID NO 7
<211> LENGTH: 20
<212> TYPE: RNA
<213> ORGANISM: Artificial Sequence

```
<220> FEATURE:
<223> OTHER INFORMATION: antisense oligonulceotide

<400> SEQUENCE: 7
accaaccucu gaacuauucc                                               20

<210> SEQ ID NO 8
<211> LENGTH: 20
<212> TYPE: RNA
<213> ORGANISM: Artificial Sequence
<220> FEATURE:
<223> OTHER INFORMATION: antisense oligonucleotide

<400> SEQUENCE: 8
cacaaccaac cucugaacua                                               20

<210> SEQ ID NO 9
<211> LENGTH: 20
<212> TYPE: RNA
<213> ORGANISM: Artificial Sequence
<220> FEATURE:
<223> OTHER INFORMATION: antisense oligonucleotide

<400> SEQUENCE: 9
uccauagguu ggcaccuaaa                                               20

<210> SEQ ID NO 10
<211> LENGTH: 20
<212> TYPE: RNA
<213> ORGANISM: Artificial Sequence
<220> FEATURE:
<223> OTHER INFORMATION: antisense oligonucleotide

<400> SEQUENCE: 10
uguuccauag guuggcaccu                                               20

<210> SEQ ID NO 11
<211> LENGTH: 20
<212> TYPE: RNA
<213> ORGANISM: Artificial Sequence
<220> FEATURE:
<223> OTHER INFORMATION: antisense oligonucleotide

<400> SEQUENCE: 11
guauaccuga gaagauugcc                                               20

<210> SEQ ID NO 12
<211> LENGTH: 20
<212> TYPE: RNA
<213> ORGANISM: Artificial Sequence
<220> FEATURE:
<223> OTHER INFORMATION: antisense oligonucleotide

<400> SEQUENCE: 12
ucuuugcagu auaccugaga                                               20

<210> SEQ ID NO 13
<211> LENGTH: 20
<212> TYPE: RNA
<213> ORGANISM: Artificial Sequence
<220> FEATURE:
<223> OTHER INFORMATION: antisense oligonucleotide

<400> SEQUENCE: 13
uguaccguau guagguaucu                                               20
```

```
<210> SEQ ID NO 14
<211> LENGTH: 20
<212> TYPE: RNA
<213> ORGANISM: Artificial Sequence
<220> FEATURE:
<223> OTHER INFORMATION: antisense oligonucleotide

<400> SEQUENCE: 14
ccguauguag guaucuauac                                               20

<210> SEQ ID NO 15
<211> LENGTH: 20
<212> TYPE: RNA
<213> ORGANISM: Artificial Sequence
<220> FEATURE:
<223> OTHER INFORMATION: antisense oligonucleotide

<400> SEQUENCE: 15
ucuaccugug aagagcucca                                               20

<210> SEQ ID NO 16
<211> LENGTH: 20
<212> TYPE: RNA
<213> ORGANISM: Artificial Sequence
<220> FEATURE:
<223> OTHER INFORMATION: antisense oligonucleotide

<400> SEQUENCE: 16
ugugcauucu accugugaag                                               20

<210> SEQ ID NO 17
<211> LENGTH: 20
<212> TYPE: RNA
<213> ORGANISM: Artificial Sequence
<220> FEATURE:
<223> OTHER INFORMATION: antisense oligonucleotide

<400> SEQUENCE: 17
ccucaucaaa cauagagaag                                               20

<210> SEQ ID NO 18
<211> LENGTH: 20
<212> TYPE: RNA
<213> ORGANISM: Artificial Sequence
<220> FEATURE:
<223> OTHER INFORMATION: antisense oligonucleotide

<400> SEQUENCE: 18
ggaaauuuug uacugaccuc                                               20

<210> SEQ ID NO 19
<211> LENGTH: 20
<212> TYPE: RNA
<213> ORGANISM: Artificial Sequence
<220> FEATURE:
<223> OTHER INFORMATION: control sequence

<400> SEQUENCE: 19
agguccacac ucaauccuca                                               20

<210> SEQ ID NO 20
<211> LENGTH: 20
<212> TYPE: RNA
<213> ORGANISM: Artificial Sequence
<220> FEATURE:
<223> OTHER INFORMATION: antisense oligonucleotide
```

```
<400> SEQUENCE: 20
aaaccucuga gcuacuccag                                                    20

<210> SEQ ID NO 21
<211> LENGTH: 20
<212> TYPE: RNA
<213> ORGANISM: Artificial Sequence
<220> FEATURE:
<223> OTHER INFORMATION: antisense oligonucleotide

<400> SEQUENCE: 21
gcacaaaccu cugagcuacu                                                    20

<210> SEQ ID NO 22
<211> LENGTH: 20
<212> TYPE: RNA
<213> ORGANISM: Artificial Sequence
<220> FEATURE:
<223> OTHER INFORMATION: antisense oligonucleotide

<400> SEQUENCE: 22
aucagcacaa accucugagc                                                    20

<210> SEQ ID NO 23
<211> LENGTH: 20
<212> TYPE: RNA
<213> ORGANISM: Artificial Sequence
<220> FEATURE:
<223> OTHER INFORMATION: antisense oligonucleotide

<400> SEQUENCE: 23
aaaucagcac aaaccucuga                                                    20

<210> SEQ ID NO 24
<211> LENGTH: 20
<212> TYPE: RNA
<213> ORGANISM: Artificial Sequence
<220> FEATURE:
<223> OTHER INFORMATION: antisense oligonucleotide

<400> SEQUENCE: 24
gaaaaucagc acaaaccucu                                                    20

<210> SEQ ID NO 25
<211> LENGTH: 20
<212> TYPE: RNA
<213> ORGANISM: Artificial Sequence
<220> FEATURE:
<223> OTHER INFORMATION: antisense oligonucleotide

<400> SEQUENCE: 25
aggaaaauca gcacaaaccu                                                    20

<210> SEQ ID NO 26
<211> LENGTH: 20
<212> TYPE: RNA
<213> ORGANISM: Artificial Sequence
<220> FEATURE:
<223> OTHER INFORMATION: antisense oligonucleotide

<400> SEQUENCE: 26
cauagguugg caccuauaaa                                                    20

<210> SEQ ID NO 27
```

```
<211> LENGTH: 20
<212> TYPE: RNA
<213> ORGANISM: Artificial Sequence
<220> FEATURE:
<223> OTHER INFORMATION: antisense oligonucleotide

<400> SEQUENCE: 27
uuccauaggu uggcaccuau                                                     20

<210> SEQ ID NO 28
<211> LENGTH: 20
<212> TYPE: RNA
<213> ORGANISM: Artificial Sequence
<220> FEATURE:
<223> OTHER INFORMATION: antisense oligonucleotide

<400> SEQUENCE: 28
ugagcuccau ggauucuucc                                                     20

<210> SEQ ID NO 29
<211> LENGTH: 15
<212> TYPE: DNA
<213> ORGANISM: Artificial Sequence
<220> FEATURE:
<223> OTHER INFORMATION: antisense oligonucleotide

<400> SEQUENCE: 29
cactcttctg ttcca                                                          15

<210> SEQ ID NO 30
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 30
cacaaacctc tgagct                                                         16

<210> SEQ ID NO 31
<211> LENGTH: 17
<212> TYPE: DNA
<213> ORGANISM: Artificial Sequence
<220> FEATURE:
<223> OTHER INFORMATION: antisense oligonucleotide

<400> SEQUENCE: 31
cacaaacctc tgagcta                                                        17

<210> SEQ ID NO 32
<211> LENGTH: 21
<212> TYPE: DNA
<213> ORGANISM: Artificial Sequence
<220> FEATURE:
<223> OTHER INFORMATION: antisense oligonucleotide

<400> SEQUENCE: 32
aaccucugaa cuauuccaug u                                                   21

<210> SEQ ID NO 33
<211> LENGTH: 21
<212> TYPE: DNA
<213> ORGANISM: Artificial Sequence
<220> FEATURE:
<223> OTHER INFORMATION: antisense oligonucleotide
```

```
<400> SEQUENCE: 33
accucugaac uauuccaugu a                                            21

<210> SEQ ID NO 34
<211> LENGTH: 27
<212> TYPE: DNA
<213> ORGANISM: Artificial Sequence
<220> FEATURE:
<223> OTHER INFORMATION: antisense oligonucleotide

<400> SEQUENCE: 34
ttcatctgtt ccataggttg gcaccta                                      27

<210> SEQ ID NO 35
<211> LENGTH: 27
<212> TYPE: DNA
<213> ORGANISM: Artificial Sequence
<220> FEATURE:
<223> OTHER INFORMATION: antisense oligonucleotide

<400> SEQUENCE: 35
ttccataggt tggcacctaa aaaaaaa                                      27

<210> SEQ ID NO 36
<211> LENGTH: 20
<212> TYPE: DNA
<213> ORGANISM: Artificial Sequence
<220> FEATURE:
<223> OTHER INFORMATION: scrambled antisense nucleotide with
      phosphothiorate backbone

<400> SEQUENCE: 36
gcaccucugc guccuagaat                                              20

<210> SEQ ID NO 37
<211> LENGTH: 20
<212> TYPE: DNA
<213> ORGANISM: Artificial Sequence
<220> FEATURE:
<223> OTHER INFORMATION: primer

<400> SEQUENCE: 37
gaaaaggaga gtgtccaggg                                              20

<210> SEQ ID NO 38
<211> LENGTH: 26
<212> TYPE: DNA
<213> ORGANISM: Artificial Sequence
<220> FEATURE:
<223> OTHER INFORMATION: primer

<400> SEQUENCE: 38
gaacttctac tcctcctttt attagt                                       26

<210> SEQ ID NO 39
<211> LENGTH: 20
<212> TYPE: DNA
<213> ORGANISM: Artificial Sequence
<220> FEATURE:
<223> OTHER INFORMATION: probe

<400> SEQUENCE: 39
ccaaaaagcc aaaggaaccc                                              20
```

<210> SEQ ID NO 40
<211> LENGTH: 22
<212> TYPE: DNA
<213> ORGANISM: Artificial Sequence
<220> FEATURE:
<223> OTHER INFORMATION: primer

<400> SEQUENCE: 40
acaactttgg tatcgtggaa gg                                              22

<210> SEQ ID NO 41
<211> LENGTH: 19
<212> TYPE: DNA
<213> ORGANISM: Artificial Sequence
<220> FEATURE:
<223> OTHER INFORMATION: primer

<400> SEQUENCE: 41
gccatcacgc cacagtttc                                                  19

<210> SEQ ID NO 42
<211> LENGTH: 23
<212> TYPE: DNA
<213> ORGANISM: Artificial Sequence
<220> FEATURE:
<223> OTHER INFORMATION: primer

<400> SEQUENCE: 42
gaggaggatg taaaggtagc tca                                             23

<210> SEQ ID NO 43
<211> LENGTH: 23
<212> TYPE: DNA
<213> ORGANISM: Artificial Sequence
<220> FEATURE:
<223> OTHER INFORMATION: primer

<400> SEQUENCE: 43
actggcaaac atatcttcat ggc                                             23

<210> SEQ ID NO 44
<211> LENGTH: 20
<212> TYPE: DNA
<213> ORGANISM: Artificial Sequence
<220> FEATURE:
<223> OTHER INFORMATION: primer

<400> SEQUENCE: 44
tgcagggtca caaaaagtgc                                                 20

<210> SEQ ID NO 45
<211> LENGTH: 20
<212> TYPE: DNA
<213> ORGANISM: Artificial Sequence
<220> FEATURE:
<223> OTHER INFORMATION: primer

<400> SEQUENCE: 45
agcactccct gcatttccaa                                                 20

<210> SEQ ID NO 46
<211> LENGTH: 23
<212> TYPE: DNA
<213> ORGANISM: Artificial Sequence
<220> FEATURE:
<223> OTHER INFORMATION: primer -continued

<400> SEQUENCE: 46
atggagctca tggacctttt agg                                           23

<210> SEQ ID NO 47
<211> LENGTH: 21
<212> TYPE: DNA
<213> ORGANISM: Artificial Sequence
<220> FEATURE:
<223> OTHER INFORMATION: primer

<400> SEQUENCE: 47
tgcaactctt gactatgggg g                                             21

<210> SEQ ID NO 48
<211> LENGTH: 21
<212> TYPE: DNA
<213> ORGANISM: Artificial Sequence
<220> FEATURE:
<223> OTHER INFORMATION: TAg FW primer

<400> SEQUENCE: 48
caccctgata aggtgggga c                                              21

<210> SEQ ID NO 49
<211> LENGTH: 22
<212> TYPE: DNA
<213> ORGANISM: Artificial Sequence
<220> FEATURE:
<223> OTHER INFORMATION: TAg RV primer

<400> SEQUENCE: 49
gcaaaacagg tcttcatccc ac                                            22

<210> SEQ ID NO 50
<211> LENGTH: 21
<212> TYPE: DNA
<213> ORGANISM: Artificial Sequence
<220> FEATURE:
<223> OTHER INFORMATION: VP1 FW primer

<400> SEQUENCE: 50
ccaaagaatg ccacagtgca a                                             21

<210> SEQ ID NO 51
<211> LENGTH: 21
<212> TYPE: DNA
<213> ORGANISM: Artificial Sequence
<220> FEATURE:
<223> OTHER INFORMATION: VP1 RV primer

<400> SEQUENCE: 51
gtgggatcag gaacccaaca t                                             21

<210> SEQ ID NO 52
<211> LENGTH: 35
<212> TYPE: DNA
<213> ORGANISM: Artificial Sequence
<220> FEATURE:
<223> OTHER INFORMATION: target sequence exon 1

<400> SEQUENCE: 52
gaacctggag ccagaggttg tgctgatttt cctct                              35

<210> SEQ ID NO 53
<211> LENGTH: 40

```
<212> TYPE: DNA
<213> ORGANISM: Artificial Sequence
<220> FEATURE:
<223> OTHER INFORMATION: target sequence exon 2

<400> SEQUENCE: 53
taattatttt tttttttmtag gtgccaacct atggaacaga                              40

<210> SEQ ID NO 54
<211> LENGTH: 40
<212> TYPE: DNA
<213> ORGANISM: Artificial Sequence
<220> FEATURE:
<223> OTHER INFORMATION: target sequence exon 1

<400> SEQUENCE: 54
gaacctggag tagctcagag gtttgtgctg attttcctct                              40

<210> SEQ ID NO 55
<211> LENGTH: 40
<212> TYPE: DNA
<213> ORGANISM: Artificial Sequence
<220> FEATURE:
<223> OTHER INFORMATION: target sequence exon 1

<400> SEQUENCE: 55
gtacatggaa tagttcagag gttggttgtg attttcctcc                              40

<210> SEQ ID NO 56
<211> LENGTH: 39
<212> TYPE: DNA
<213> ORGANISM: Artificial Sequence
<220> FEATURE:
<223> OTHER INFORMATION: target sequence intron 2

<400> SEQUENCE: 56
ctyaattytt tkttttttagg tgccaaccta tggaacaga                              39

<210> SEQ ID NO 57
<211> LENGTH: 40
<212> TYPE: DNA
<213> ORGANISM: Artificial Sequence
<220> FEATURE:
<223> OTHER INFORMATION: target sequence exon 1

<400> SEQUENCE: 57
atatatggca atcttctcag gtatactgca aagatttgtg                              40

<210> SEQ ID NO 58
<211> LENGTH: 40
<212> TYPE: DNA
<213> ORGANISM: Artificial Sequence
<220> FEATURE:
<223> OTHER INFORMATION: target sequence exon 2

<400> SEQUENCE: 58
tgtatatttt tgttgtatag atacctacat acggtacacc                              40

<210> SEQ ID NO 59
<211> LENGTH: 40
<212> TYPE: DNA
<213> ORGANISM: Artificial Sequence
<220> FEATURE:
<223> OTHER INFORMATION: target sequence exon 1
```

```
<400> SEQUENCE: 59
aagtgtggag ctcttcacag gtagaatgca cagaattgtg                           40

<210> SEQ ID NO 60
<211> LENGTH: 40
<212> TYPE: DNA
<213> ORGANISM: Artificial Sequence
<220> FEATURE:
<223> OTHER INFORMATION: target sequence exon 2

<400> SEQUENCE: 60 ataactttttt tttattatag atacccacat atggtacccc                          40

<210> SEQ ID NO 61
<211> LENGTH: 40
<212> TYPE: DNA
<213> ORGANISM: Artificial Sequence
<220> FEATURE:
<223> OTHER INFORMATION: target sequence exon 1

<400> SEQUENCE: 61
acttctctat gtttgatgag gtcagtacaa aatttccttg                           40

<210> SEQ ID NO 62
<211> LENGTH: 40
<212> TYPE: DNA
<213> ORGANISM: Artificial Sequence
<220> FEATURE:
<223> OTHER INFORMATION: target sequence exon 2

<400> SEQUENCE: 62
ttctgtactt tcccatctag gttgacgagg cccctatata                           40

<210> SEQ ID NO 63
<211> LENGTH: 40
<212> TYPE: DNA
<213> ORGANISM: Artificial Sequence
<220> FEATURE:
<223> OTHER INFORMATION: target sequence exon 1

<400> SEQUENCE: 63
cctggtgctt ttcctctgag gtcagtgatg attggggtat                           40

<210> SEQ ID NO 64
<211> LENGTH: 40
<212> TYPE: DNA
<213> ORGANISM: Artificial Sequence
<220> FEATURE:
<223> OTHER INFORMATION: target sequence exon 2

<400> SEQUENCE: 64
acttataatt tattttacag gtaaggccac ctccacaata                           40

<210> SEQ ID NO 65
<211> LENGTH: 40
<212> TYPE: DNA
<213> ORGANISM: Artificial Sequence
<220> FEATURE:
<223> OTHER INFORMATION: target sequence exon 1

<400> SEQUENCE: 65
ggcattacag ctctgatgag gtcagttttt gggatataga                           40

<210> SEQ ID NO 66
```

```
<211> LENGTH: 40
<212> TYPE: DNA
<213> ORGANISM: Artificial Sequence
<220> FEATURE:
<223> OTHER INFORMATION: target sequence exon 2

<400> SEQUENCE: 66
tactaattat cttttttag gtgagacctc cgcccccata                        40

<210> SEQ ID NO 67
<211> LENGTH: 40
<212> TYPE: DNA
<213> ORGANISM: Artificial Sequence
<220> FEATURE:
<223> OTHER INFORMATION: target sequence exon 1

<400> SEQUENCE: 67
caactagctt cagtagccag gtaggctcat ggtattggga                       40

<210> SEQ ID NO 68
<211> LENGTH: 40
<212> TYPE: DNA
<213> ORGANISM: Artificial Sequence
<220> FEATURE:
<223> OTHER INFORMATION: target sequence exon 2

<400> SEQUENCE: 68
aatttagttt ttcctttag catgatgttc caacccagga                        40

<210> SEQ ID NO 69
<211> LENGTH: 40
<212> TYPE: DNA
<213> ORGANISM: Artificial Sequence
<220> FEATURE:
<223> OTHER INFORMATION: target sequence exon 1

<400> SEQUENCE: 69
gtggatcctc ctcttctcag gtagcttggt acttttggga                       40

<210> SEQ ID NO 70
<211> LENGTH: 40
<212> TYPE: DNA
<213> ORGANISM: Artificial Sequence
<220> FEATURE:
<223> OTHER INFORMATION: target sequence exon 2

<400> SEQUENCE: 70
atgtaagtat tttttttag ggatactaca gtgattctcc                        40

<210> SEQ ID NO 71
<211> LENGTH: 40
<212> TYPE: DNA
<213> ORGANISM: Artificial Sequence
<220> FEATURE:
<223> OTHER INFORMATION: target sequence exon 1

<400> SEQUENCE: 71
aagtttattt tcctgcaaag gttggttact ttatagamga                       40

<210> SEQ ID NO 72
<211> LENGTH: 40
<212> TYPE: DNA
<213> ORGANISM: Artificial Sequence
<220> FEATURE:
<223> OTHER INFORMATION: target sequence exn 2
```

<400> SEQUENCE: 72
tkyttyytyt tttattttag ggwaayccca cttatggkac                      40

<210> SEQ ID NO 73
<211> LENGTH: 40
<212> TYPE: DNA
<213> ORGANISM: Artificial Sequence
<220> FEATURE:
<223> OTHER INFORMATION: target sequence exon 1

<400> SEQUENCE: 73
atgaaaatrt ktwtccgccg gtaagaatgt tgttgttaas                      40

<210> SEQ ID NO 74
<211> LENGTH: 40
<212> TYPE: DNA
<213> ORGANISM: Artificial Sequence
<220> FEATURE:
<223> OTHER INFORMATION: target sequence exon 2

<400> SEQUENCE: 74
tggtaagttt ttctttttag ggcggacaat atggtacycc                      40

<210> SEQ ID NO 75
<211> LENGTH: 40
<212> TYPE: DNA
<213> ORGANISM: Artificial Sequence
<220> FEATURE:
<223> OTHER INFORMATION: target sequence exon 1

<400> SEQUENCE: 75
gaatctacaa tctgagagag gtaaagcctt ccctacatcc                      40

<210> SEQ ID NO 76
<211> LENGTH: 40
<212> TYPE: DNA
<213> ORGANISM: Artificial Sequence
<220> FEATURE:
<223> OTHER INFORMATION: target sequence exon 2

<400> SEQUENCE: 76
taatttaata aaatttacag tacaatcctc ataggaatcc                      40

<210> SEQ ID NO 77
<211> LENGTH: 40
<212> TYPE: DNA
<213> ORGANISM: Artificial Sequence
<220> FEATURE:
<223> OTHER INFORMATION: target sequence exon 1

<400> SEQUENCE: 77
ttgaagtaag agactcagag gtatgtcaag tttcttttc                       40

<210> SEQ ID NO 78
<211> LENGTH: 40
<212> TYPE: DNA
<213> ORGANISM: Artificial Sequence
<220> FEATURE:
<223> OTHER INFORMATION: taregt sequence exon 2

<400> SEQUENCE: 78 ttaattttt tattttgcag gtcttttctg attcctatgg                       40

<210> SEQ ID NO 79

```
<211> LENGTH: 40
<212> TYPE: DNA
<213> ORGANISM: Artificial Sequence
<220> FEATURE:
<223> OTHER INFORMATION: consensus target sequence exon 1
<220> FEATURE:
<221> NAME/KEY: misc_feature
<222> LOCATION: (4)..(5)
<223> OTHER INFORMATION: n is a, c, g, or t
<220> FEATURE:
<221> NAME/KEY: misc_feature
<222> LOCATION: (11)..(11)
<223> OTHER INFORMATION: n is a, c, g, or t
<220> FEATURE:
<221> NAME/KEY: misc_feature
<222> LOCATION: (13)..(13)
<223> OTHER INFORMATION: n is a, c, g, or t
<220> FEATURE:
<221> NAME/KEY: misc_feature
<222> LOCATION: (27)..(29)
<223> OTHER INFORMATION: n is a, c, g, or t
<220> FEATURE:
<221> NAME/KEY: misc_feature
<222> LOCATION: (31)..(32)
<223> OTHER INFORMATION: n is a, c, g, or t
<220> FEATURE:
<221> NAME/KEY: misc_feature
<222> LOCATION: (37)..(37)
<223> OTHER INFORMATION: n is a, c, g, or t
<220> FEATURE:
<221> NAME/KEY: misc_feature
<222> LOCATION: (39)..(40)
<223> OTHER INFORMATION: n is a, c, g, or t

<400> SEQUENCE: 79
vhdnnwvbwd nhnydvwsag gthdrhnnnd nnkwwbndnn                       40

<210> SEQ ID NO 80
<211> LENGTH: 40
<212> TYPE: DNA
<213> ORGANISM: Artificial Sequence
<220> FEATURE:
<223> OTHER INFORMATION: target sequence exon 2 consensus
<220> FEATURE:
<221> NAME/KEY: misc_feature
<222> LOCATION: (2)..(3)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t
<220> FEATURE:
<221> NAME/KEY: misc_feature
<222> LOCATION: (27)..(27)
<223> OTHER INFORMATION: n is a, c, g, or t
<220> FEATURE:
<221> NAME/KEY: misc_feature
<222> LOCATION: (30)..(30)
<223> OTHER INFORMATION: n is a, c, g, or t
<220> FEATURE:
<221> NAME/KEY: misc_feature
<222> LOCATION: (33)..(33)
<223> OTHER INFORMATION: n is a, c, g, or t

<400> SEQUENCE: 80
wnnwwwdwtt twyytthyag rdnnvhnmhn mynvhhmdbm                       40

<210> SEQ ID NO 81
<211> LENGTH: 20
<212> TYPE: RNA
<213> ORGANISM: Artificial Sequence
<220

```
<400> SEQUENCE: 81
uccauagguu ggcaccuaua                                              20

<210> SEQ ID NO 82
<211> LENGTH: 38
<212> TYPE: DNA
<213> ORGANISM: Artificial Sequence
<220> FEATURE:
<223> OTHER INFORMATION: target sequence exon 2

<400> SEQUENCE: 82
taattatttk ttttmtaggt gccaacctat ggaacaga                          38

<210> SEQ ID NO 83
<211> LENGTH: 40
<212> TYPE: DNA
<213> ORGANISM: Artificial Sequence
<220> FEATURE:
<223> OTHER INFORMATION: target sequence exon 1

<400> SEQUENCE: 83
gaacctggaa tagctcagag gtttgtgctg attttcctct                        40

<210> SEQ ID NO 84
<211> LENGTH: 40
<212> TYPE: DNA
<213> ORGANISM: Artificial Sequence
<220> FEATURE:
<223> OTHER INFORMATION: target sequence exon 2

<400> SEQUENCE: 84
taattatttt tttkttatag gtgccaacct atggaacaga                        40

<210> SEQ ID NO 85
<211> LENGTH: 40
<212> TYPE: DNA
<213> ORGANISM: Artificial Sequence
<220> FEATURE:
<223> OTHER INFORMATION: target sequence exon 1

<400> SEQUENCE: 85
gaacctggaa tagctcagag gtttgtgctg attttcctct                        40

<210> SEQ ID NO 86
<211> LENGTH: 40
<212> TYPE: DNA
<213> ORGANISM: Artificial Sequence
<220> FEATURE:
<223> OTHER INFORMATION: target sequence exon 2

<400> SEQUENCE: 86
taattatttt tttttttatag gtgccaacct atggaacaga                       40

<210> SEQ ID NO 87
<211> LENGTH: 40
<212> TYPE: DNA
<213> ORGANISM: Artificial Sequence
<220> FEATURE:
<223> OTHER INFORMATION: target sequence exon 1

<400> SEQUENCE: 87
gaacctggag tagctcagag gtttgtgctg attttcctct                        40

<210> SEQ ID NO 88
```

```
<211> LENGTH: 40
<212> TYPE: DNA
<213> ORGANISM: Artificial Sequence
<220> FEATURE:
<223> OTHER INFORMATION: target sequence exon 2

<400> SEQUENCE: 88
taattatktt ttttttatag gtgccaacct atggaacaga                              40

<210> SEQ ID NO 89
<211> LENGTH: 40
<212> TYPE: DNA
<213> ORGANISM: Artificial Sequence
<220> FEATURE:
<223> OTHER INFORMATION: target sequence exon 1

<400> SEQUENCE: 89
gaacctggar tagctcagag gtttgtgctg attttcctct                             40

<210> SEQ ID NO 90
<211> LENGTH: 40
<212> TYPE: DNA
<213> ORGANISM: Artificial Sequence
<220> FEATURE:
<223> OTHER INFORMATION: target sequence exon 2

<400> SEQUENCE: 90
taattatktk ttttttmtag gtgccaacct atggaacaga                             40
```